US007560102B2

(12) United States Patent
Eisenbach-Schwartz et al.

(10) Patent No.: US 7,560,102 B2
(45) Date of Patent: Jul. 14, 2009

(54) METHOD FOR REDUCING NEURONAL DEGENERATION SO AS TO AMELIORATE THE EFFECTS OF INJURY OR DISEASE

(75) Inventors: Michal Eisenbach-Schwartz, Rehovot (IL); Ehud Hauben, Rehovot (IL); Irun R. Cohen, Rehovot (IL); Pierre Beserman, Moshav Sitriya (IL); Alon Monsonego, Rehovot (IL); Gila Moalem, Petah-Tiqva (IL)

(73) Assignee: Yeda Research and Development Co., Ltd, Rehovot (IL)

( * ) Notice: Subject to any disclaimer, the term of this patent is extended or adjusted under 35 U.S.C. 154(b) by 710 days.

(21) Appl. No.: 10/810,653

(22) Filed: Mar. 29, 2004

(65) Prior Publication Data

US 2004/0253218 A1    Dec. 16, 2004

Related U.S. Application Data

(63) Continuation of application No. 09/893,348, filed on Jun. 28, 2001, now abandoned, which is a continuation-in-part of application No. 09/314,161, filed on May 19, 1999, now abandoned, and a continuation-in-part of application No. 09/218,277, filed on Dec. 22, 1998, now abandoned, which is a continuation-in-part of application No. PCT/US98/14715, filed on Jul. 21, 1998.

(30) Foreign Application Priority Data

May 19, 1998   (IL)   .................................. IL 124550

(51) Int. Cl.
| | |
|---|---|
| A61K 38/04 | (2006.01) |
| A61K 38/17 | (2006.01) |
| C12N 5/00 | (2006.01) |
| C07K 14/435 | (2006.01) |
| C07K 7/00 | (2006.01) |

(52) U.S. Cl. ................ 424/93.1; 424/184.1; 424/185.1; 424/93.7; 514/2; 514/12; 530/300; 530/326; 530/350

(58) Field of Classification Search ....................... None
See application file for complete search history.

(56) References Cited

U.S. PATENT DOCUMENTS

| | | | |
|---|---|---|---|
| 5,114,721 A | 5/1992 | Cohen et al. | |
| 5,250,414 A | 10/1993 | Schwab et al. | |
| 5,633,426 A | 5/1997 | Namikawa et al. | |
| 5,684,133 A | 11/1997 | Schwab et al. | |
| 5,858,364 A | 1/1999 | Weiner et al. | |
| 6,319,892 B1 | 11/2001 | Gold et al. | |
| 2003/0108528 A1 | 6/2003 | Eisenbach-Schwartz | |

FOREIGN PATENT DOCUMENTS

| | | |
|---|---|---|
| WO | WO 91/01746 | 2/1991 |
| WO | WO 93/00427 A2 | 1/1993 |
| WO | WO 93/21222 | 10/1993 |
| WO | WO 95/22344 | 8/1995 |
| WO | WO 95/27500 | 10/1995 |
| WO | WO 96/12737 | 5/1996 |
| WO | WO 96/16085 A1 | 5/1996 |
| WO | WO 97/14427 | 4/1997 |
| WO | WO 97/35879 | 10/1997 |
| WO | WO 99/12966 | 3/1999 |
| WO | WO99/34827 A1 | 7/1999 |
| WO | WO 99/53945 | 10/1999 |
| WO | WO 00/31235 A1 | 6/2000 |
| WO | WO 00/31235 A2 | 6/2000 |
| WO | WO 00/31235 A3 | 6/2000 |
| WO | WO 00/60083 A1 | 10/2000 |
| WO | WO 01/36631 A1 | 5/2001 |

OTHER PUBLICATIONS

Wells. J.A. Additivity of mutational effects in proteins. Biochemistry 29 (37): 8509-8517, 1990.*
Ngo et al. Computational complexity, protein structure prediction, and the Levinthal paradox. The Protein Folding Problem and Tertiary Structure Prediction, pp. 492-495, 1994.*
Yu et al. Global analysis of the cortical neuron proteome. Molec Cellular Proteomics 3: 896-907, 2004.*
Fisher et al. Vaccination for neuroprotection in the mouse optic nerve: implications for optic neuropathies. J Neurosci 21(1): 136-142, 2001.*
Becker, et al., "Immunologic Tolerance to Myelin Basic Protein Decreases Stroke Size After Transient Focal Cerebral Ischemia", *Proc Natl Acad Sci USA* 94(20):10873-10878 (1997).
Ben-Nun, et al., "The Rapid Isolation of Clonable Antigen-specific T Lymphocyte Lines Capable of Mediating Autoimmune Encephalomyelitis," *Eur J Immunol.*, 11:195-199, (1981).
Berkow, et al (Eds), *The Merck Manual of Diagnosis and Therapy* 16th Ed., Merck Research Laboratories, Rahway, NJ, pp. 110, 111, 412, 413, 1452-1459, 1488-1490, 1510, 1511, and 1518-1523 (1992).
Bradbury, et al, "NT-3, but not BDNF, Prevents Atrophy and Death of Axotomized Spinal Cord Projection Neurons", *Eur J Neurosci*;10(10):3058-3068 (1998).
Brittis, et al., "Nogo Domains and a Nogo Receptor: Implications for Axon Regeneration", *Neuron*, 30(1):11-14 (2001).
Brod, et al, "Autologous T-T Cell Activation Mediated by Cell Adhesion Molecules", *FASEB J* 3(3):A514 (1989).
Brosamle, et al., "Regeneration of Lesioned Corticospinal Tract Fibers in the Adult Rat Induced by a Recombinant, Humanized IN-1 Antibody Fragment", *J. Neurosci*, 20(21):8061-8068, (2000).

(Continued)

*Primary Examiner*—Bridget E Bunner
(74) *Attorney, Agent, or Firm*—Browdy and Neimark P.L.L.C.

(57) ABSTRACT

Compositions and methods to promote nerve regeneration or to confer neuroprotection and prevent or inhibit neuronal degeneration within the nervous system, either the central nervous system or the peripheral nervous system, are provided. Treatment involves administering NS-specific activated T cells, or an NS-specific antigen or analog thereof, a peptide derived therefrom or an analog or derivative of said peptide, or a nucleotide sequence encoding such an antigen or peptide, or any combination thereof.

27 Claims, 30 Drawing Sheets

OTHER PUBLICATIONS

Burns, et al., "Isolation of Myelin Basic Protein-Reactive T-Cell Lines from Normal Human Blood", *Cellular Immunology*, 81:435-440 (1983).

Chen, et al., "Regulatory T Cell Clones Induced by Oral Tolerance: Suppression of Autoimmune Encephalomeylitis", *Science*, 265: 1237-1240 (1994).

Chen, et al, "Nogo-A is a Myelin-Associated Neurite Outgrowth Inhibitor and an Antigen for Monoclonal Antibody IN-1", *Nature* 403(6768):434-439 (2000).

Cohen, "The Cognitive Principle Challenges Clonal Selection", *Immunology Today*, 13(11)441-444, (1992).

Cohen, et al, "Autoimmune Maintenance and Neuroprotection of the Central Nervous System", *J. Neuroimmuno*: 100(1-2):111-114 (1999).

Enoch, et al, "Different Functional Changes Recorded In Open Angle Glaucoma and Anterior Ischemic Optic Neuropathy", *Doc Ophthalmol* 50(1):169-184 (1980).

Faden, "Experimental Neurobiology of Central Nervous System Trauma" *Critical Reviews in Neurobiology* 7(3/4):175-186 (1993).

Feigin, et al, "Recent advances in Huntington's disease: implication for experimental therapeutics", *Curr Opin Neurol* 15:483-48 (2002).

Fournier, et al, "Identification of a receptor mediating Nogo-66 inhibition of axonal regeneration", *Nature* 409(6818):341-346 (2001).

George, et al, "Axotomy-induced Axonal Degeneration is Mediated by Calcium Influx through Ion-Specific Channels", *J Neurosci* 15(10):6445-6452 (1995).

Grandpre, et al., "Identification of the Nogo Inhibitor of Axon Regeneration as a Reticulon Protein", *Nature* 403(6768):439-444 (2000).

Grandpre, et al., "Nogo-66 Receptor Antagonist Peptide Promotes Axonal Regeneration." *Nature* 417 (6888):547-551 (2002).

Halliday, et al, "Alzheimer's Disease and Inflammation: A Review of Cellular and Therapeutic Mechanisms", *Clin Exp Pharmacol Physiol* 27:1-8, 2000.

Hauben, et al, "Autoimmune T Cells As Potential Neuroprotective Therapy For Spinal Cord Injury", *Lancet* 355(9200):286-287 (2000).

Hauben, et al, "Passive or active immunization with myelin basic protein promotes recovery from spinal cord contusion", *J Neurosci.* 20(17):6421-6430 (2000).

Hauben, et al, "Vaccination with a Nogo-A-Derived Peptide after Incomplete Spinal-cord Injury Promotes Recovery Via a T-Cell-Mediated Neuroprotective Response: Comparison with other Myelin Antigens", *Proc Natl Acad Sci USA* 98(26): 15173-15178 (2001).

Hay RJ, "Human Cells and Cell Cultures: Availability, Authentication and Future Prospects", *Hum Cell* 9(3):143-152 (1996).

Hickey, et al., "T-Lymphocyte Entry into the Central Nervous System", *Journal of Neuroscience Research* 28:254-260 (1991).

Hirschberg, et al., "Accumulation of Passively Transferred Primed T cells Independently of their Antigen Specificity Following Central Nervous System Trauma", *Journal of Neuroimmunology* 89:88-96 (1998).

Hovda, et al., "Diffuse Prolonged Depression of Cerebral Oxidative Metabolism following Concussive Brain Injury in the Rat: A Cytochrome Oxidase Histochemistry Study", *Brain Research* 567:1-10 (1991).

Huber, et al, "Nogo-A, a potent inhibitor of neurite outgrowth and regeneration", *Biol Chem* 381(5-6):407-419 (2000).

Huber, et al, "Patterns of Nogo Mma and Protein Expression in the Developing And Adult Rat and after CNS Lesions", *J Neurosci* 22(9):3553-3567 (2002).

Jackowski A, "Neural Injury Repair: Hope for the Future as Barriers to Effective CNS Regeneration Become Clearer", *Br J Neurosurg* 9(3):303-317 (1995).

Janeway, Jr., "The immune System Evolved to Discriminate Infectious Nonself from Noninfectious Self", *Immunology Today* 13(1):11-16, (1992).

Kandel et al (Eds.), *Principles of Neural Science* Elsevier Science Publishing Co., Inc. (New York, NY), pp. 977-982.

Kerschensteiner et al., "Activated Human T Cells, B Cells, and Monocytes Produce Brain-derived Neurotropic Factor In Vitro and in Inflammatory Brain Lesions: A Neuroprotective Role of Inflammation", *J. Exp. Med.* 189(5):865-870, (1999).

Kramer et al., "Gene transfer through the blood-nerve barrier: NGF-engineered neuritogenic T Lymphocytes attenuate experimental autoimmune neuritis", *Nature Medicine*, 1(11):1162-1166 (1995).

Lazarov et al., "Transplantation of activated macrophages results in partial recovery of paraplegic rats", *Nature Medicine*, 4(7):814-821 (1998).

Li et al, "β-Endorphin omission analogs: dissociation of immunoreactivity from other biological activities", *Proc Natl Acad Sci USA* 77(6):3211-3214 (1980).

Liu et al, "Hydroxl Radicals Generated in Vivo Kill Neurons in the Rat Spinal Cord: Electrophysiological, Histological, and Neurochemical Results", *Journal of Neurochemistry*, 62(1):37-44 (1994).

Liuzzi, et al, "Peripheral Nerve Regeneration", *Neurosurg Clin N Am* 2(1):31-42 (1991).

Lohse, et al, "Control of Experimental Autoimmune Encephalomyelitis by T Cells Responding to Activated T Cells", *Science* 244:820-822 (1989).

Lohse, et al, "Inhibition of the Mixed Lymphocyte Reaction by T Cell Vaccination", *Eur J Immunol* 20:2521-2524 (1990).

Lohse, et al, "Induction of the Anti-Erogtypic Response", *International Immunology* 4(5):533-539 (1993).

Martin, et al, "Gine Specificity and HLS Restriction of Myelin Basic Protein Specific Cyctotoxic T Cell Lines from Multiple Sclerosis Patients and Healthy Individuals" *The Journal of Immunology*, 145(2):540-548 (1990).

Merkler, et al, "Locomotor Recovery in Spinal Cord-injured Rats Treated with an Antibody Neutralizing the Myelin-associated Neurite Growth Inhibitor Nogo-A," *J. Neurosci.* 21(10):3665-3673 (2001).

Moaelem et al, "Autoimmune T Cells Protect Neurons from Secondary Degeneration after Central Nervous System Axotomy", *Nature Medicine* 5(1):49-55 (1999).

Moalem et al, "Autoimmune T cells Retard the Loss of Function in Injured Rat Optic Nerves", *J Neuroimmunol* 106(1-2):189-197 (2000).

Mor et al, "Pathogenicity of T Cells Responsive to Diverse Cryptic Epitopes of Myelin Basic Protein in the Lewis Rat:," *The Journal of Immunology*, 155(7):3693-3699 (1995).

Morris et al, "The Consortium to Establish a Registry for Alzheimer's Disease (CERAD). Part I. Clinical and Neuropsychological Assessment of Alzheimer's Disease", *Neurology* 39(9):1159-1165 (1989).

Ota et al, "T-cell Recognition of an immunodominant Myelin Basic Protein Epitope in Multiple Sclerosis," *Nature*, 346:183-187 (1990).

Pan, et al, "Tumor Necrosis Factor-alpha: A Neuromodulator in the CNS", *Neurosci Biobehav Rev* 21(5):603-613 (1997).

Pette, et al., "Myelin in Autoreactivity in Multiple Sclerosis: Recognition of Myelin Basic Protein in the Context of HLA-DR2 Products by T Lymphocytes of Multiple-Sclerosis Patients and Healthy Donors", *Proc. Natl. Acac. Sci. USA* 87:7968-7972(1990).

Petrovich, et al, "Pentoxifylline Suppression of TNF-α Mediated Axonal Degeneration in the Rabbit Optic Nerve," *Neurol Res* 19(5):551-554 (1997).

Plata Salaman C, "Epidermal Growth Factor and the Nervous System",*Peptides* 12(3):653-663 (1991).

Popovich, et al, "Cellular Inflammatory Response After Spinal Cord Injury in Sprague-Dawley and Lewis Rats" *The Journal of Comparative Neurology*, 377:443-464, (1997).

Popovich, et al, "Concepts of Autoimmunity Following Spinal Cord Injury: Possible Roles for T Lymphocytes in the Traumatized Central Nervous System", *Journal of Neuroscience Research*, 45:349-363, (1996).

Poser CM, "The Role of Trauma in the Pathogenesis of Multiple Sclerosis: A Review," *Clin Neurol Neurosurg* 96(2):103-110 (1994).

Prinjha, et al, "Animal Studies Raise Hopes for Spinal Cord Repair,"*Nature* 403(6768):383-384 (2000).

Rapalino, et al, "Implantation of Stimulated Homologous Macrophages Results in Partial Recovery of Paraplegic Rats," *Nature Medicine*, 4(7):814-821 (1998).

Schluesener, et al, "Autoaggressive T Lymphocyte Line Recognizing the Encephalitogenic Region of Myelin Basic Protein: in Vitro Selection from Unprimed Rat T Lymphocyte Populations," *The Journal of Immunology*, 135(5):3128-3133 (1985).

Schwab, et al, "Degeneration and Regeneration of Axons in the Lesioned Spinal Cord," *Physiol Rev.*, 76(2):319-370, (1996).

Schwartz, J, "Synthesis and Trafficking of Neuronal Proteins," *Principles of Neural Science*, Connecticut Appleton and Lange, 1991, pp. 49-65; p. 264-265.

Skolnick, et al, "From Genes to Protein Structure and Function: Novel Applications of Computational Approaches in the Genomic Era", *Trends Biotechnol* 18(1):34-39 (2000).

Steece-Collier, et al, "Etiology of Parkinson's Disease: Genetics and Environment Revisited," *Proc Natl Acad Sci USA* 99(22):13972-13974 (2002).

Streilien, "Unraveling Immune Privilege", *Science* 270:1158-1159 (1995).

Streilien, "Immune Privilege as the Result of Local Tissue Barrier and Immunosuppressive Microenvironments." *Current Opinion in Immunology* 5:428-432 (1993).

Tanabe, et al, "Diversity and pattern in the developing spinal cord", *Science* 274(5290):1115-1123 (1996).

Wang, et al, "Pathogenesis of axonal degeneration: parallels between Wallerian degeneration and vincristine neuropathy", *J Neuropathol Exp Neurol* 59(7):599-606 (2000).

Wekerle, "Lymphocyte Traffic to the Brain," *The Blood Brain Barrier*, Pardridge, ed., 1:67-85 Raven Press Ltd. (1993).

Wickelgren, et al, "Neuroscience. Animal Studies Raise Hope for Spinal Cord Repair," *Science* 297(5579):178-181 (2002).

Woolf, et al, "Neuroscience. It Takes More than Two to Nogo," *Science* 297(5584):1132-1134, 2002.

Yoles, et al, "GM1 Reduces Injury-Induced Metabolic Deficits and Degeneration in the Rat Optic Nerve," *Investigation Ophthamology & Visual Science* 33(13):3586-3591 (1992).

Yoshino, et al, "Dynamic Changes in Local Cerebral Glucose Utilization Following Cerebral Concussion in Rats: Evidence of a Hyper- and Subsequent Hypometabolic State," *Brain Research* 561:1-10 (1991).

Yücel, et al, "Histomorphometric Analysis of Optic Nerve Changes in Experimental Glaucoma", *J Glaucoma* 8(1):38-45 (1999).

Yuen, et al, "immunoregulatory CD8$^+$ Cells Recognize Antigen-Activated CD4$^+$ Cells in Myasthenia Gravis Patients and in Healthy Controls", *J Immunol* 154(3):1508-1520 (1995).

Zivin, et al, "Stroke Therapy," *Scientific American* 265(1):36-43 (1991).

Karin, N et al., "Reversal of Experimental Autoimmune Encephalomyelitis by a Soluble Peptide Variant of a Myelin Basic Protein Epitope: T Cell Receptor Antagonism and Reduction of Interferon Gamma and Tumor Necrosis Factor Alpha Production", J. Exp. Med. 180:2227-2237 (1994).

Karin, N et al., "Short Peptide-Based Tolerogens without Self-Antigenic or Pathogenic Activity Reverse Autoimmune Disease," J. Immunol. 160:5188-5194 (1998).

Monsonego, A et al., "Beeficial Effect of Orally Administered Myelin Basic Protein in EAE-Susceptible Lewis Rats in a Model of Acute CNS Degeneration," J. Autoimmunity 21:131-138 (2003).

Schwartz, M et al "Protective Autoimmunity: Regulation and Prospects for Vaccination after Brain and Spinal Cord Injuries," Trends in Molecular Medicine 7:252-258 (2001).

Smilek, D et al, "A Single Amino Acid Change in a Myelin Basic Protein Peptide Confers the Capacity to Prevent Rather than Induce Experimental Autoimmune Encephalomyelitis," Proc. Natl. Acad. Sci. USA 88:9633-9637 (1991).

Vergelli, M. et al, "Differential Activation of Human Autoreactive T cell Clones by Altered Peptide Ligands Derived from Myelin Basic Protein Peptide (87-99)," Eur. J. Immunol. 26:2624-2634 (1996).

\* cited by examiner

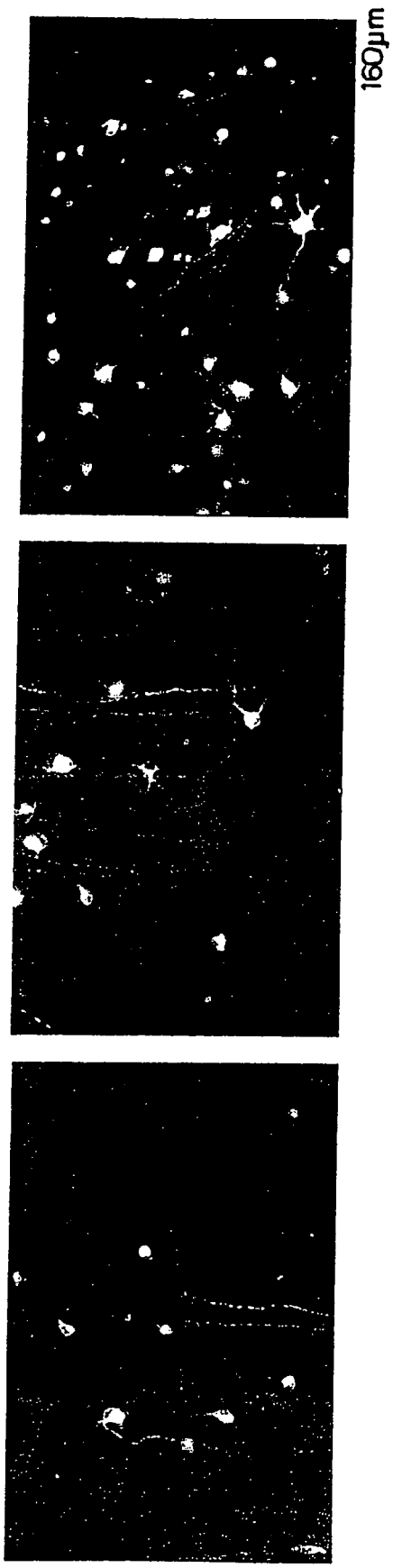

*FIG. 12A*      *FIG.12B*
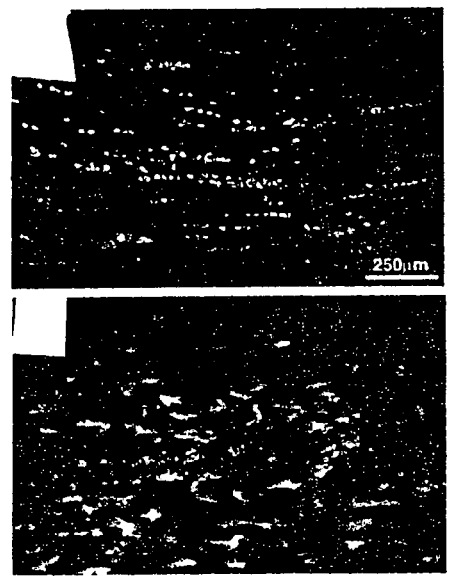 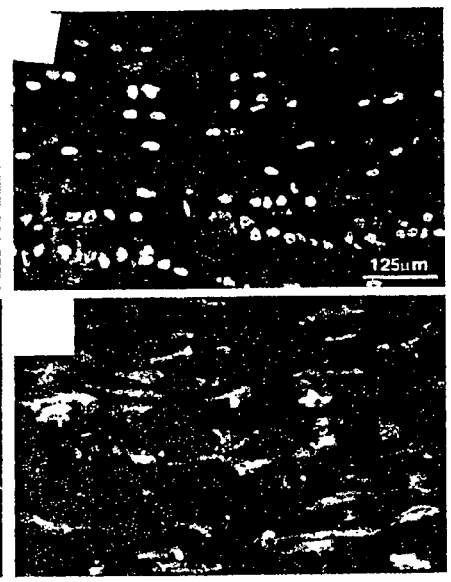
*FIG. 12C*      *FIG.12D*
*FIG. 12E*
*FIG. 12F*
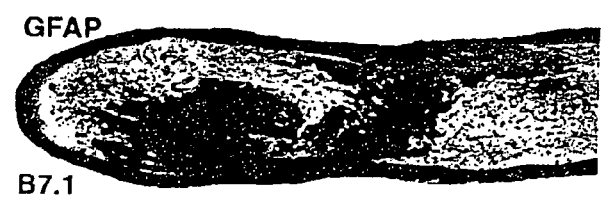

FIG. 13A
FIG. 13B
GFAP
ED-1
T-cells
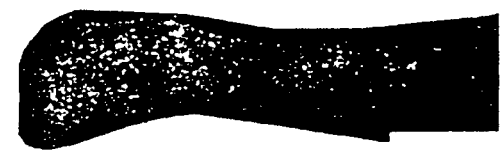
FIG. 13C
GFAP
B7.2

FIG. 15

```
  1   ccaagaagat cccacagcag cttccgaagg cctggatgtg atggcatcac agaagagacc
 61   ctcacagcga cacggatcca agtacttggc cacagcaagt accatggacc atgcccggca
121   tggcttcctc ccaaggcaca gagacacggg catccttgac tccatcgggc gcttctttag
181   cggtgacagg ggtgcgccca agcgggctc tggcaaggac tcacacacaa gaactaccca
241   ctacggctcc ctgccccaga agtcgcagag gacccaagat gaaacccag tagtccactt
301   cttcaagaac attgtgacac ctcgtacacc cctccatcc caaggaaagg ggagaggcct
361   gtccctcagc agatttagct ggggaggaag agacagccgc tctggatctc ccatggcaag
421   acgctgagag cctccctgct cagccttccc gaatcctgcc ctcggcttct taatataact
481   gccttaaacg tttaattcta cttgcaccaa atagctagtt agagcagacc ctctcttaat
541   cccgtggggc tgtgaacgcg gcgggccagc ccacggcacc ctgactggct aaaactgttt
601   gtccctttt at
```

FIG. 16

```
   1   gaaaacagtg cagccacctc cgagagcctg gatgtgatgg cgtcacagaa gagaccctcc
  61   cagaggcacg gatccaagta cctggccaca gcaagtacca tggaccatgc caggcatggc
 121   ttcctcccaa ggcacagaga cacgggcatc cttgactcca tcgggcgctt ctttggcggt
 181   gacaggggtg cgccaaagcg gggctctggc aaggactcac caccccggc aagaactgct
 241   cactatggct ccctgcccca gaagtcacac ggccggaccc aagatgaaaa ccccgtagtc
 301   cacttcttca gaacattgt gacgcctcgc acaccacccc cgtcgcaggg aaaggggaga
 361   ggactgtccc tgagcagatt tagctggggg ccgaaggcc agagaccagg atttggctac
 421   ggaggcagag cgtccgacta taaatcggct cacaagggat tcaagggagt cgatgcccag
 481   ggcacgcttt ccaaaatttt taagctggga ggaagagata gtcgctctgg atcacccatg
 541   gctagacgct gaaaacccac ctggttccgg aatcctgtcc tcagcttctt aatataactg
 601   ccttaaaact ttaatcccac ttgcccctgt tacctaatta gagcagatga cccctcccct
 661   aatgcctgcg gagttgtgca cgtagtaggg tcaggccacg gcagcctacc ggcaatttcc
 721   ggccaacagt taatgagaa catgaaaaca gaaaacggtt aaaactgtcc ctttctgtgt
 781   gaagatcacg ttccttcccc cgcaatgtgc cccagacgc acgtgggtct tcaggggcc
 841   aggtgcacag acgtccctcc acgttcaccc ctccacccct ggactttctt ttcgccgtgg
 901   ctcggcaccc ttgcgctttt gctggtcact gccatggagg cacacagctg cagagacaga
 961   gaggacgtgg gcggcagaga ggactgttga catccaagct tcctttgttt ttttttcctg
1021   tccttctctc acctcctaaa gtagacttca ttttttcctaa caggattaga cagtcaagga
1081   gtggcttact acatgtggga gcttttggt atgtgacatg cgggctgggc agctgttaga
1141   gtccaacgtg gggcagcaca gagaggggc caccttccca ggccgtggct gcccacacac
1201   cccaattagc tgaattcgcg tgtggcagag ggaggaaaag gaggcaaacg tgggctgggc
1261   aatggcctca cataggaaac agggtcttcc tggagatttg gtgatggaga tgtcaagcag
1321   gtggcctctg gacgtcaccg ttgccctgca tggtggcccc agagcagcct ctatgaacaa
1381   cctcgttttcc aaaccacagc ccacagccgg agagtccagg aagacttgcg cactcagagc
1441   agaagggtag gagtcctcta gacagcctcg cagccgcgcc agtcgcccat agacactggc
1501   tgtgaccggg cgtgctggca gcggcagtgc acagtggcca gcactaaccc tccctgagaa
1561   gataaccggc tcattcactt cctcccagaa gacgcgtggt agcgagtagg cacaggcgtg
1621   cacctgctcc cgaattactc accgagacac acgggctgag cagacggccc ctgtgatgga
1681   gacaaagagc tcttctgacc atatccttct taacacccgc tggcatctcc tttcgcgcct
1741   ccctccctaa cctactgacc caccttttga ttttagcgca cctgtgattg ataggccttc
1801   caaagagtcc cacgctggca tcaccctccc cgaggacgga gatgaggagt agtcagcgtg
1861   atgccaaaac gcgtcttctt aatccaattc taattctgaa tgtttcgtgt gggcttaata
1921   ccatgtctat taatatatag cctcgatgat gagagagtta caaagaacaa aactccagac
1981   acaaacctcc aaatttttca gcagaagcac tctgcgtcgc tgagctgagg tcggctctac
2041   gatccatacg tggccgcacc cacacagcac gtgctgtgac gatggctgaa cggaaagtgt
2101   acactgttcc tgaatattga aataaaacaa taaactttt
```

FIG. 17A

```
  1 taatatctag ggktttgact ctgacccgtg ttggggctct cacttcatgg cttctcacgc
 61 ttgtgctgca tatcccacac caattagacc caaggatcag ttggaagttt ccaggacatc
121 ttcattttat ttccaccctc aatccacatt tccagatgtc tctgcagcaa agcgaaattc
181 caggcaagcc ttagggaaaa aaggaaaaac aaagaaaatg aaacaattgg cagtgaaagg
241 cagaaagaga agatggagcc cttagagaag ggagtatccc tgagtaggtg gggaaaaggg
301 gaggagaagg ggaggaggag aggaggagga aagcaggcct gtccctttaa ggggggttggc
361 tgtcaatcag aaagcccttt tcattgcagg agaagaggac aaagatactc agagagaaaa
421 agtaaaagac cgaagaagga ggctggagag accaggatcc ttccagctga acaaagtcag
481 ccacaaagca gactagccag ccggctacaa ttggagtcag agtcccaaag acatgggtaa
541 gtttcaaaaa ctttagcatt gaagattcaa gaggacacag g
```

FIG. 17B

```
   1 ctgctttcag agcctgtgac ttcttgtgtg cctctcctgt ttctcagcaa catggcatag
  61 ggcctgggat accaggtctg gggatctcag ggactcttag cactttaaga cacatgtgtt
 121 cccaggccct ggtgtgttcc tctagtgcca gaaagatgtt tcatgctttg ctgactttgt
 181 ataaagtctg tttgtagctg ttttgacaga atctcagcgt ataactgagg gtggggacat
 241 tagccaagct gcattatagg aggacaaaac tgccatacaa agtgtccaaa atcattaagc
 301 ctgcatttt attattggga gtaatatcaa acctcctatt ttccaatttt catttcttgt
 361 cctgtgctag ctccatcctg tttggactgc tcctcccata tgtaaactaa gaagaatcaa
 421 gcattctttg caacaaatac acacgatgct caaaaatgtc caggagcatc caatttccaa
 481 agtttcctcc acctggaatg ctcttcatgc taaaatcctg tctgacaata ccagcatctc
 541 tggcctgcac tcatcccttc ctggaactcc aagtgcattt accctctgtt accacttact
 601 tggctgcctg aattgttagt tgaaaatatt aggtctactt agctaattct tcctcaggaa
 661 attaaagact cccatatggc agagtctgtg tctttctct cttcatatcc cgtataacac
 721 ccagcataat gctgggcata tagtgagtat tccataaata gttgatgaat gactaaaata
 781 agcaagcaaa caaacagact agaacaataa gaaagaaggg actggatttc ataatctctc
 841 tggcttgcta tttgaattgc tgaattatta ttatttatta aatatttttt aaattctggc
 901 aataaaaggt aaggatttat tttcttctt tcttttttt tttcttgaga cagagtctcg
 961 ctcttactgc ccaggctgga gtacaatggc gcaatcttgg ctcacggcaa cctccgcctc
1021 ctcctgggtt taacagattc tcctgtctca gcctcctgag tagctgggat tacaggcata
1081 cgcccatgcc cggctaattt ttgtattttt agtagagacg gggttttgcc atgttggcca
1141 ggctggtctt gaactcctga cctcatgtga tccacctgcc tcagcctccc aaagtgctgg
1201 gattacaggc atgcgccacc gtgcccggcc aaagatttat tttcaagaat gaaacaaagt
1261 aaggattctg ggtcaatctc acatgctgaa agccaaaacc tctagccgct cctgcttttt
1321 gacttcggag tgcccactat ctccgagcct gtgagcacag gcctggcag agggggtttga
1381 gtggcatgag ctacctactg gatgtgcctg actgtttccc cttcttcttc cccaggcttg
1441 ttagagtgct gtgcaagatg tctggtaggg gccccttttg cttccctggt ggccactgga
1501 ttgtgttct tggggtggc actgttctgt ggctgtggac atgaagccct cactggcaca
1561 gaaagctaa ttgagaccta tttctccaaa aactaccaag actatgagta tctcatcaat
1621 gtgtaagtac ctgccctccc acacagaccc atcttttttt tccctctctc catcctggag
1681 atagagaact cttcagtacc ttagtaacta gcagggact ggggtggagc cagaccggat
1741 tcccgagtct tccctctgtg ca
```

FIG. 17C

```
  1  ctagaaaatc cctagccttg ttaaggtgct cgctctggtg tatacctcac ttatgtcggg
 61  aaagaagcca ggtcttcaat taataagatt ccctggtctc gtttgtctac ctgttaatgc
121  aggatccatg ccttccagta tgtcatctat ggaactgcct cttcttctt cctttatggg
181  gccctcctgc tggctgaggg cttctacacc accggcgcag tcaggcagat ctttggcgac
241  tacaagacca ccatctgcgg caagggcctg agcgcaacgg taacagggg ccagaagggg
301  aggggttcca gaggccaaca tcaagctcat tctttggagc gggtgtgtca ttgtttggga
361  aaatggctag gacatcccga caaggtgatc atcctcagga ttttgtggca ataacaaggg
421  gtggggaaa attgggcgcg agtctgtggc ctcgtccca cccaaggctg ggtcctctct
481  aggggcctgg catttgagtg aggaagcgat ggctgcagcc gaacgagaag gtcaggaaga
541  acgtggtgcc cagctggctt agcctcacct ttcaaaggtt ccctaagcaa atttcttctc
601  aaaacagaaa gcatgagttt tgtgggatgc tttgtacaat cagaccattt ctaagccatc
661  tgttggtatc cctttgttcc cttcctagta ggtaccacaa gagtggatct aactggacaa
721  gagtctaaaa tgctgctcat gtgattgaga cttgggcacc tgagctraga gggaggatgg
781  ataataaaaa ttaaataata actccaaggt aaatttacaa tgttctgg
```

FIG. 17D

```
   1  gatcctcctc attcttcccc tacccattcc ccccaccctc cgttatactg gggccagtta
  61  tctagtagat actgccaatt acccttggca gaggtgccct gctcactaat tttatttggg
 121  ggagmgccct ggaacctggt tttaatgtct ggcacacgcc acttccagga tctcccagtt
 181  tgtgtttcta catctgcagg ctgatgctga tttctaacca acccatgtca atcattttag
 241  tttgtgggca tcacctatgc cctgaccgtt gtgtggctcc tggtgtttgc ctgctctgct
 301  gtgcctgtgt acatttactt caacacctgg accacctgcc agtctattgc cttccccagc
 361  aagacctctg ccagtatagg cagtctctgt gctgatgcca gaatgtatgg tgagttaggg
 421  tacggtgct ttggctctcc tacccactat ggaagcacta tatatttggt tatttttcta
 481  gtgtaaggag ggtggtgatt atgagaaaaa tataagatga tgaatgattg ggtcttagtt
 541  tattaatcct tccctactga aaccagagag gtttcttccc ccggaaggga acttggaagt
 601  ggtgggagtt ttcttggcca ttcacattgg cctactctag ttgactgctg ttcacaaccc
 661  caaagcagca catttcaata acaaacacaa ggttdsacca ctgttcaata ccaccttctc
 721  ttttttgtaa acctgtagaa aagaggatcc taattgttgg tagmatccaa mtttacagcc
 781  aggataatta gagatggaag aagggctctg ggggaaagtc tccatgtggc cccgtaactc
 841  cataaagctt accctgcttg cttttgtgt cttacttagg tgttctccca tggaatgctt
 901  tccctggcaa ggtttgtggc tccaaccttc tgtccatctg caaaacagct gaggtgagtg
 961  ggttatttgg gttattttac aagggagtag ctaataccat acaaattaca cccatggcct
1021  tcaattttaa ggactgaaag tttccctttg ctggattttg aattagccga ttgccttcta
1081  caacatgttg gctaagtgtg cctgagccaa tgagcataga aggtaaaaca cctctttct
```

FIG. 17E

```
  1  aattagcaca cagaaaggat atccaacaca tacaaagctg tnntcatgga ctacactgga
 61  gcatattact gctgttgcaa gaaacatttc ttcttcctct tttcattttc ctgcagttcc
121  aaatgacctt ccacctgttt attgctgcat ttgtggggc tgcagctaca ctggttccc
181  tggtgagttg actttgaatg atcttggcaa gtaaataggc ctgagatagt tgtgggtaca
241  gctattctga aaggcaagaa ggtagactgc ttccatcctt gaaatgctgg aggga
```

FIG. 17F

```
   1 aattctatat actatcacta tggctccact ttggatactc tccagtggat ttagttactc
  61 atatggaaat acctgggagg acctcctaac attattagaa ttgttatgat tataatacaa
 121 ygctatgtcc caggtcttgc tgatagtgct acagtgccct gtgaatgtag tgtgctcatt
 181 gtgcagatta aaaacctaag gcactgaagg gtgaagtgat ttatctgaag ttattttata
 241 aagcagtgat cagacaasct gagctcacag aactccctgg cccctactgc tgaggtttcc
 301 atacagagtc aagtaatttc tcaccttgta aaacgaattg attcattaac caggggagag
 361 ctctactgca tgatgtggct gtgtgtctac agcaagcacc ctatgactct aagtcactcg
 421 gacatattga tgtggcaaag cccaaatatt gttcacttcc ctgaggaaaa ctcagtgcta
 481 gatcaaacag aggtgtggaa taaatcttta tgatttgatt ctctgggcct gggccatgag
 541 acccatgatg cctcagagac atcggacttc cagtcaagtg tatatggaga aagccaagcc
 601 tgggatgtac tgcttttgc agagcatggg ttttccctt atttagttat gattttattt
 661 ctacccttcc tcattcccaa agggatttga ggagggagtg ctttctttc tactctcatt
 721 cacattctct cttctgttcc ctacagctca ccttcatgat tgctgccact tacaactttg
 781 ccgtccttaa actcatgggc cgaggcacca agttctgatc ccccgtagaa atccccctt
 841 ctctaatagc gaggctctaa ccacacagcc tacaatgctg cgtctcccat cttaactctt
 901 tgcctttgcc accaactggc cctcttctta cttgatgagt gtaacaagaa aggagagtct
 961 tgcagtgatt aaggtctctc tttggactct ccctcttat gtacctcttt tagtcatttt
1021 gcttcatagc tggttcctgc tagaaatggg aaatgcctaa taatatgact tcccaactgc
1081 aagtcacaaa ggaatggagg ctctaattga atttcaagc atctcctgag gatcagaaag
1141 taatttcttc tcaaagggta cttccactga tggaaacaaa gtggaaggaa agatgctcag
1201 gtacagagaa ggaatgtctt tggtcctctt gccatctata ggggccaaat atattctctt
1261 tggtgtacaa aatggaattc attctgcgtc tctctattac actgaagata aagaaaaaa
1321 gaatgtcaga aaaacaataa gagcgtttgc ccaaatctgc ctattgcagc tgggagaagg
1381 gggtcaaagc aaggatcttt cacccacaga aagagagcac tgacccgat ggcgatggac
1441 tactgaagcc ctaactcagc caaccttact tacagcataa gggagcgtag aatctgtgta
1501 gacgaagggg gcatctggcc ttactcctcg ttagggaaga gaaacagggt cttgtcagca
1561 tcttctcact cccttctcct tgataacagc taccatgaca accctgtggt ttccaaggag
1621 ctgagaatag aaggaaacta gcttacatga gaacagactg gcctgaggag cagcagttgc
1681 tggtggctaa tggtgtaacc tgagatggcc ctctggtaga cacaggatag ataactcttt
1741 ggatagcatg tcttttttc tgttaattag ttgtgtactc tggcctctgt catatcttca
1801 caatggtgct catttcatgg ggtattatcc attcagtcat cgtaggtgat ttgaaggtct
1861 tgatttgttt tagaatgatg cacatttcat gtattccagt ttgtttatta cttatttggg
1921 gttgcatcag aaatgtctgg agaataattc tttgattatg actgcttttt aaactaggaa
1981 aattggacat taagcatcac aaatgatatt aaaaattggc tagttgaatc tattgggatt
2041 ttctacaagt attctgcctt tgcagaaaca gatttggtga atttgaatct caatttgagt
2101 aatctgatcg ttctttctag ctaatgaaaa atgatttac ttagcaatgt tatcttggtg
2161 tgttaagagt taggtttaac ataaggtta ttttctcctg atatagatca cataacagaa
2221 tgcaccagtc atcagctatt cagttggtaa gcttccagtc atcagctatt cagttggtaa
2281 gcttcccagg aaaaaggaca ggcagaaaga gtttgagacc tgaatagctc ccagatttca
2341 gtcttttaat gttttgtta actttgggtt aaaaaaaaa aaagtctgat tggttttaat
2401 tgaaggaaag atttgtacta cagttctttt gttgtaaaga gttgtgttgt tcttttcccc
2461 caaagtggtt tcagcaatat ttaaggagat gtaagagctt tacaaaaaga cacttgatac
2521 ttgttttcaa accagtatac aagataagct tccaggctgc atagaaggag gagagggaaa
2581 atgttttgta agaaaccaat caagataaag gacagtgaag taatccgtac cttgtgtttt
2641 gttttgattt aataacataa caaataacca acccttccct gaaaacctca catgcataca
2701 tacacatata tacacacaca aagagagtta atcaactgaa agtgttcctt catttctgat
2761 atagaattgc aattttaaca cacataaagg ataaactttt agaaacttat cttacaaagt
2821 gtattttata aaattaaaga aaataaaatt aagaatgttc tcaatcaaac atcgtgtcct
2881 ttgagtgaat tgttctattt gacttcacaa tagaaactta ataatcgtac cttctcaaga
```

FIG. 18A

```
   1 atggaaatgt tctgtatttg tgttgtctga tgagataacc actaactgta gtgctattga
  61 gcatttgaaa catggctagt gtaatcaatg aaccaaattt ttaattttat ttaattgtaa
 121 ttaattttaa gtggccacat gcagggagtg actgctgcat tggacagcac ggctctaaat
 181 tgagcctttt ttccttattt ggtgaggcat acttgcctta agattgggaa gtctattttt
 241 ggaacctgct accaatgctg gtctcacact tgcaattctc agctgagcca agaggtgaga
 301 gaaaggtcat tttccattcc aagatctcac tctccctgt gacactgagg aaactggcaa
 361 gtgatgtgaa ggctggagag cgtgtcctgt atgctggctc tgtcccttct gcctgtgttg
 421 actgacatag ttagttgctg cccttgctgg tctcccttcc tccaaccttg cctctctgag
 481 cacacctgac attcatctca tgacttccct aaaaacattc tttgggaaca agaaactaac
 541 aaatcccaag tgacctatca catatacaaa catacagggc agagtttgga ttcgcggtag
 601 aagaagggga ggttagacat taagaagaat ggtctggtga tgacagttgt gagataatag
 661 aaacaggaaa aagaaatcta agttttcttt cttttttaa gaaccaataa taatttctct
 721 cttttgacta gtcagtaggg ctggggtgga ttggaggaag cttacatatt ccatgaacaa
 781 gcctcttcct aaggtcctgt aagtgatcct gccccactga ttagcccta gaagacctt
 841 caaaggttgg atctccagga gggagtgggg gaggaaagcc ctgtaccagg cagcctctgc
 901 tccattgctc tgggggggtg gggaagacaa accctggtca tcccctcagt ctgtagccct
 961 tttgtgtgag tgcctggcaa gggtgacgtg gggctgtttc tgcgggcaca gctgcagcaa
1021 ttaccggagt ggaggcaggg cccaggcagc actgccctcc aagatcttcc cttgggcttt
1081 tcagcagtaa ggggacatgc accccaaggg cctccacttg gcctgacctt gctgcggggg
1141 ctctctgtcc ccaggaacag tagagatggc aagcttatcg agaccctctc tgcccagctg
1201 cctctgctcc ttcctcctcc tcctcctcct ccaagtgtct tccagctatg caggtaagac
1261 atgttttttt tcctgccctg gggagaccct gaaaacagaa aggctagttt cctgggggtt
1321 agctccttca aacatcctca agttggtata ttatctttct aaaacataga cctactgaca
1381 tgcctccctt cctcagaaac cttccgtggg tggttcttac agccttcaag atggagtcca
1441 gactcttttt ttttttgggg acagagtctc cctctgttgc tcaggctgga gtgcagtggc
1501 atgatctcgg ctcactgcaa cctcagcctc cctggttcaa gcgattctcc tgacttggcc
1561 tcccaagtag cggagactac aggcgcctgc caccacaccc agctaaattt gttctttct
1621 ttctttttt tttttttgg gattttagga cagacggggt ttcacatgtt ggccaggatg
1681 gtctcgatct cttgacctgc tgatccgccc gcctcagctt cccaaagtac tgggattatg
1741 ggcgtgagcc actgcactag gcctaatttt tttatttta gtagagatgg ggtttcacca
1801 tgttggccag gctggtctgg aaccctgac ctcaagtggt ctgccctcct cagcctccca
1861 aagttctgag attacaggca tgagccattg cgtctgaccc agactcctta atgtgactaa
1921 ctccaggctt tccttggact acttcttact tgtctttcca gctttgtctt ttcacctctc
1981 caattgagat aaaataataa caacctcttg gagttctcat caggattaca tgaaatgaga
2041 tatgtaacat gcttagcagt gcctgtccat agtaaatctc aataaatgtt tgtggaatta
2101 taatatcttg tcatgtttga gactttgctc tgcataatca ggcaccagta ggttttttata
2161 aaggaacccg tctgtcacgt gcagaggaga aataaacaga aagtttccca tcctcaggga
2221 gccacctgac tgacagaggc acagtgcatc cactctccag gtctagggga gaaagcagcc
2281 ttatttctta gtagctcaga atctgacttg agaaacacat ccacatagaa aaaacaagg
2341 aacttttcg ggtcagggtc cgggacccac agtgaggtgg aagatacagg ggaaggaaga
2401 gggaaataga gccatcccca gggtggaaga tctcagaaga gaatttggga aacaaggtat
2461 gaacaaggac tgaatagtga gaagtgatgg agagacagct aaagtagatg gagtgtcaaa
2521 accaaaacct ctaagggtag aataggcagc aatttggcca gtcctaaca gggaggccca
2581 taggaggatt caacctcaag atgctgtgcc acattccaag agggaaccta aaggctgggc
2641 tgaagagtca gagatggcta cagctggcaa aaagatgggc agatgctgag aggagatgat
2701 tgctaaaatg ttctgtccag gacattcaca gtatctctat aaccagagtc ttttttgtcg
2761 ttgttgttct caagaaggaa acttgaggcc gggtgtggtg gtttatgccc ataatcccag
2821 cgctttgggg ccaaggcagg cggatcacct gaggtcagga gttcgagacc agcctggcca
2881 acagtgtgaa acctcatctt tactaaaaat acaaaaatta gctggatgcg gcggtaggtg
2941 cctgtaatgc cagctactcg ggaggctgag caggagaat cacttgaacc tgggaggcgg
3001 aggttgcagg gaggcggagg ttgcagtgag ccaagattgc accactgcac tccagcctgg
```

FIG. 18B

```
3061  gcgacagaga gtaagactgt ctcaaaaaat aaatgaataa ataaaaagga agaagaagaa
3121  gaagaacaat tgcaatcctc cctggctcta gaatgtcatt taaaagtcga gtgtcttctt
3181  ccttccctgt tttgaagcag cccttctcat gacaggcttg cttgccaagg ttccctctga
3241  ccttaaatct cttccttttg gtgtcttgga cagggcagtt cagagtgata ggaccaagac
3301  accctatccg ggctctggtc ggggatgaag tggaattgcc atgtcgcata tctcctggga
3361  agaacgctac aggcatgcag gtgcggtggt accgccccc cttctctagg gtggttcatc
3421  tctacagaaa tggcaaggac caagatggag accaggcacc tgaatatcgg ggccggacag
3481  agctgctgaa agatgctatt ggtgagggaa aggtgactct caggatccgg aatgtaaggt
3541  tctcagatga aggaggtttc acctgcttct tccgagatca ttcttaccaa gaggaggcag
3601  caatggaatt gaaagtagaa ggtgagtagt gccatataat attaggtatt aactgttggg
3661  tggccaagaa caattattct ctcaactgag atgagatccc tcaacccaaa catctcagtc
3721  ctgggaatga tttccataaa aatgtacaca tcaataaaca gaaactcatg cttagggatg
3781  tctgttgcat cattattcag agtagcaagg aaattgggat caaaatcaat gcctttgagt
3841  aggtaagtga cagaatgaac aatggtagcc atactgtgaa tattatgcag ggattaaaaa
3901  gattatttta gcactaggcc agatggtttg gggggctcct ctaaggtatt attgagtgat
3961  aagagcaagc tgctgtagga tacaaaaaca aaaacaaaac cctagggcat ggtggtttgc
4021  ctcgcagcta ctcaggaggc tgagacggga ggctggcttg agcccagggg tttgcagtta
4081  cagtgagcta tgattgcacc actgcactcc aacccgggtg acagagcaaa gaccttcacc
4141  cccactccct acccgtctct aaaaaaaaca aaaacaaaaa caaaaaaacc cttgggccca
4201  gcgccgtggc tcacgcctgt aatcccagca ctgtgggagg ccgaggtggg cagatcacaa
4261  ggtcaggaga tcgagaccat cctggctaaa acggtgaaac cccgtctcta ctaaaaatac
4321  aaaaaaaaaa aaaaaattta gccaggcatg gtagcaggcg cctgtagtcc cagctactcg
4381  ggaggctgag gcaggagaat ggcgtgaacc cggaagcgga ggttgcagtg agccaaaatc
4441  cttccactgc actccagcat gggggacaca gcgagactcc gtctcaaaaa aaaaaaaaaa
4501  accctgtatt tgtgagcgca cacacacaca cacacacaca cacacctgtg cttggtccta
4561  gtgaataagc aagtaaatca aatgtctaaa tataattata gaaaggagat gtcacctttt
4621  ggctgtacct ccactatttc attctgcaga attgcagaat ttcttttttt tttcctttct
4681  ttctttctct ttttttttttg acacagagtc tcgctctgta acccaggctg gagtgcaatg
4741  gcgccctccg cctcctgggt tcaagtgatt ctcctgcctc agcctcccga gtagctggga
4801  ttacaggtgc ccaccaccac acccagctaa ttttgtatt tttagtagag acagggtttc
4861  accaggttgt caaggttggt ctcaaactcc tgacctcagg tgatccactc gcctcagact
4921  cccaaagtgc tgggattaca ggcatgagcc atggtgcccg gcctcagaat tcatttttca
4981  acatgttttg catgatgggt gattttggag aatattttt gctctatcgc aggatgatta
5041  agatgtggac aaggtgaagc cgatggaggg ggagctttga aagttacttg ctatttaatt
5101  gaggaactaa actgctttga gagcctgggg gtcagatcct ctgccttttc ctcctccca
5161  cctgcagtgc aaacatcaga caattgatca ctattgtatc ttggaggtgg gagtgaccat
5221  tgcagtgctg ggaccagaag atggcattgt atgtggaaca acaaagcact atttctagag
5281  actgcctgca gggatatgga aatagcttta tgtgtctcag aatgttcttc atacagctgt
5341  ttttattggg gaaattctac ttgccgaaaa gtttgatagt gagaccctct ccagtttgca
5401  gattttctc cttcctgctc aacaacttcc tagctcagta actgcctctc ccaacaaact
5461  ccctcagttt caccacacca aaaaggaag acaagccggt tgcggtggct cacacctata
5521  atcccaaaac tttgggaggc cgaggcgggt ggatccacct gaggtcggga gttcgagact
5581  agcctgacca acatggagaa accctgtctc tactaaaaac acaaaattag cctggcgtgg
5641  tggcgcattc ctgtaatccc agctgggagg ctgaggcagg agaatcgctt gaacccgga
5701  ggcggaggtt gcagtgagcc aagatcgttc cattacactc cagtctgggc aagaaaagtg
5761  gaactccatc tccaaaaaaa aaaaaaaaaa aacaaggaag acaaaaagaa aagcagctaa
5821  agactttgcc tcaggggaga aagttctctt ttgggttgct atccacattc caacctcctg
5881  ttcccacctc ttcgtctgca tgcctaagaa actgttttac aagtaaataa gggacgcttt
5941  gtctaggctt tggagccagg aagttgagac aaatttagga atgagatgaa gtaatggtat
6001  tattgcaagt ctcaggtgta actacctctg ctctttctct gaagagtttc taatttctct
6061  tgtttactta tttttttctt gtcatttttg ggattttatt actagttgtc tctaatcctt
```

FIG. 18C

```
6121  tctttaaatt cttcattatg aaacataaaa acaaatgcca ggcgcggcag ctcacgcctg
6181  taatcccagc actttgggag gccgaagcgg gcagatcacc cgggtcagga gttcgagacc
6241  agcctgatca acatggagaa accccgtctc tactaaaaaa tacaaaatta gctaggcgtg
6301  gtggcacatg ccagtaatcc cagctacttg agagactgag gcaggagaat cgcttgaacc
6361  gggaggcaga ggttgcggtg agccaagatc gcgccattgc actccagcct gggcaacaag
6421  agcaaaactc tgtctcaaaa aaaaaaaacc acatacaaac cagagataat attataatga
6481  gcctccaagt gcctaccacc ttgctgcagc acttgtcaat ccagggacca cccacctcac
6541  cggctcccca ctcattacca ccctcccta ctcaattact gaggtaaatc ctaggcagca
6601  tgatcatttc ttttttttct ttttatttat tttgagacag gatctgtctc tgtcacccag
6661  gctggagtgt agtggcatat ctctgctcac tgcagcctct gcctcccggg cagaagccat
6721  cctcccacct cagcctacat agtagctggg accacaggca cacaccacca cacactgcta
6781  atgttttgta ttttttgtag agactgggtt ttaccatgtt gatcaggctg gtctcaaact
6841  cctaggctca agcaatcctc ccacctcggc ctcccaaagt gctagaatta caggcgcgag
6901  ccactgcacc cagcgaagaa cacttttttaa aaaataaata ggccgggcgc ggtggctcac
6961  acctgtaatc ccagtacttt gggagcccaa ggagggcgaa tcatgaggtc aagagattga
7021  gaccatccta agtaacatgg tgaaacccca tttctactac aaatacaaaa acaaaattag
7081  cctggcgtgg tggcaggcgc ctgtagtccc agctacttgg gagctgaggc aggagaatgg
7141  agtgaacccg ggaggcggag cttgcagtga gctgagatca tgccactgca ctccccctg
7201  gggcaacaga gtgagactcc aaaaaaaaa aaaaaagcc cccctccc acacacaata
7261  atataaataa ataaataacc acaatactat tatcacatct tacaaactca acaaaaattt
7321  cttaatatca tcaaatacc agtttgtgtt caaattttcc tgattgtttc ataaatatac
7381  tcttacagtt ggtttctttt agcgagattc aaatgagacc cacctgttga cctttgccct
7441  tagggtttcc cagggtctga atttgttga cgacattccc atgttgctat gtaatacggt
7501  cctccatgcc ctgtgttttt ctgtaaactg atagatgtgg aggtgcaatg acatttgtgt
7561  ttgatttact ttggcaaata tagttcatca gtgatactct atacttcttg ttgctttaca
7621  tccggaggct gataatgtct gctttctct cttttctaat tatttgtgaa aggaaaaatg
7681  tgggggggttg ggagaaaaaa acccttaagt acatactcgc taaatcacat tgctacaggt
7741  aacttccatt aagaacttga aagtaaaggt agctgcattt tcccctaggg aacacaatga
7801  tagacaggag ccttagtcta cagcttgaag gattgtaatt atacctaagc aaccctcctg
7861  gaccagttta atgttattag ctgtgatgta tccctacctt tgatgtcatt atccttactt
7921  agctcccta aagcagagat caagatgaaa agggcttcag ctgcagcatg gcacatggag
7981  attagagtgg ggcttttgga tgctgaggag cagacctaga atgggaaata gatgggagcc
8041  acagaagtga aggtcccct ccctcattgc tcaacctact ccacatctcc aggtctgcac
8101  atctgttcag ttactgaatc ctgtgtaagc taccttcttt ttctttttc tttatttat
8161  ttatttattt ttttttgag atggagtttt gctcttgtta cccaggctgg agtgcaatgg
8221  tgcaatctcg gctcactgca ccctccaact cccaggttca tgcaattctc ctccctcagc
8281  cttccaagta gctgggatta caggctgcac caccatgtct ggctaatttt tgaaaaatca
8341  gtagagagag ggtttcacca tgttggccaa gccggtctcg aactcctgac ctcaagtgat
8401  ccacccacct tggcctccca aaatgctggg attacaggtg tgagccacca tgcccgctgt
8461  aaactacctt cttaaaagct ctagaagagg gcttttaacc ttttgttgtg tgtcatgcac
8521  cttccgcaag ctgatgaagt tgatagaccc atctcagaat ttttttttt ttttgagac
8581  agtgtctcac tctgtcaccc aggattggtt gcagtggcac gatcatgggt cattgcagcc
8641  tccacctccc aggctcaagt gatcctcctg actcagcctc ttgaatagct gagaccacag
8701  gcttgtgtca ccatgcccag gtaattttta attttttttc gtagaggcag ggtctcacat
8761  tatgttgccc agtctggcct cgagaactcc tgggctcaag caatcttcct gccttgggct
8821  cccaaagtgg tgggattaca ggggagagcc accaccacta gccaggagga tgttttaaat
8881  acaccaaata aaacatttat acccaaatac agttatccaa atattaaatt aacaagagtt
8941  agggtgaccc tattaattag tgtaatttcc aaatagtaat gaacataagt gatagtttga
9001  gatttctgtg acttttctaa tgtgacgtga aaatatttgt gattttttctt tttctttttt
9061  tttttgaga tggagtttcg ctcttgttgc ccaggctgga gtgcaatggc aagatctcgg
9121  ctcacctcaa cctccgcctc ctgggttcaa gcgattctcc tgcctcagcc tcttgagtag
```

FIG. 18D

```
 9181  ctgggattac aggactgtgc caccacgtcc agctaatttt gtatttttag tagaaacagg
 9241  gtttctccat gttggtcagg ctggtcttga actcccaacc tcaggcgatc cgcccgcctc
 9301  ggcctcccaa agtgctggga ttacaggtgt gagccaccgc acctggccaa tatttgtgat
 9361  ttttattgac gacaaagtca aaggttctct tcatattatt gtggtgtatc gcctacaagc
 9421  ataattaaaa taaacactaa atttcagttt aaagtttact gaaaataaat atgtattttt
 9481  tattccctat ttaagctttg aatcccctga cttcctatac cattaccact gtcctagttc
 9541  aggttcatgt tgtttttttac tttaattgtt atcacagtct cttaacattt ctccctatgt
 9601  tctccagtcc tgtaggtgct aaatctgacg tggtcacttc tcagcttgga atccttcagt
 9661  gcaccaccac agccttgaac tacatatttg aaatacatat ttattttcag taaactttaa
 9721  actgaaattt agtgtttatt ttaattatgc ttgtaggcga tacaccacaa taatatgaag
 9781  agaacctttg actttgtcgt caataaaaag tcccttgagg ggacttcaga tgtaagtccc
 9841  ttagctgctc gttaaaactc ccccaggctg acccaataca caatcttgac tttaaaccac
 9901  ttgtcattct aaatcactag catttcctgg aaaaaaaagc cattttcct tcagggctaa
 9961  gctcagggac caattctgtg tcaccttctt tgaatcctga tgatattcac ttctttattt
10021  gacctgattt attgggcccc agacaccatg ctgagtgttg gggattcagc tctggacaat
10081  gtcaaatgtc agtcctgcct ttcagatcct ttctactggg tgagccctgg agtgctggtt
10141  ctcctcgcgg tgctgcctgt gctcctcctg cagatcactc ttggcctcgt cttcctctgc
10201  ctgcagtaca gactgagagg tacagggcag agggtgggtg gatcaggatc ctttctttaa
10261  atgagctggc ttcttggagc tacaccactt aacatgtatt tgtgagtgac ttctgggttc
10321  agaagttctt ctcactattg agtgataaag aaaaaaaata actccatgat gaaagagttt
10381  tacatcttac ggaatgcttt catatgaata atcggaccta gcatttccct atgagctaac
10441  tatgccatat agtaacccca ttttacagag gatacaactg aggccaggag tagttcagtg
10501  acttactcaa accgatataa cttataagtg gtagagctga ggcctctgta tcatacctag
10561  cagctccatg caacttggga gagtgtgagc ttcgaagtca gacaggtcta ggctattagg
10621  agttttgaat aaagatactg aagtgaaagt ctctaccaca cagtaggcgt tcgaaaattg
10681  tttcctcttt ctccattcaa cactgaggac tcaggttcag ctgctgatga agctcctctt
10741  ttttgcctag agctttcatt ctgagccttc tcctcctacc aagtgtctcc ccaatgccag
10801  agcaggaaga gtcttcactc ctcccaatgc cccacctccc atttgttact aagaggagag
10861  gagaaagtag caaggagggt atggggaatg ttctggggga atgggtgttg gtgcgatcaa
10921  caacaaagtc ctttctctca ccttgaattc atcccagatg cctgcttgtt tacttcttcc
10981  acacaaaaaa aggccttcag ccctcatggc tgagcagaaa gaatctgaat gttagagtca
11041  ggcagcctgg gtttgaattc catctcaggt actgaactct atagcaaaat tcttagattc
11101  tccaagcttc agttgccttg tctgtcaaat agagaaaaca tccttcgtcc taaattgtag
11161  ggaggattaa agtcatgcaa agtgcctact acaaatccag tcacaaagta gctagctact
11221  cactaaatgt tcagctcctc cctcctcatt cagatgggaa gtggctttag ataaacaaag
11281  tggcaacgca gtgggctgga gcagctctgt gaactgagaa tccaagaaaa ggggcgaaga
11341  gcagctggga tgtattggat gcttgtgctg cttggagca ttgctcacat tctttattcg
11401  ctattgtatc tagactatag ctagagaaag agccgcaacc attggcttta aatccagtgc
11461  tcttcctact ctcctgaggt tgtttccagg ctgcagagaa atagcctgca caaggggccc
11521  aggcgctggg tgtgggaggg tccccaccga gagccagaac atgcaggaac taaaatgttg
11581  ccttttttcta ttttaggaaa acttcgagca gagataggtg agttccagtc atcgtttctc
11641  ccaattcttg ccttttggtt ttttggcata acggaaatgg tcccattctt ggaccgtctc
11701  tccctctcaa taccctgttt tcccctcagt ttccttttct ctacagtggg tgtgtcgtgc
11761  ctagaacaag ttttaagtaa ttaaataaca aagactcagg ataaaggat cctttttgga
11821  gtgccctact aaatccatt ccatttgttt ctctttcaga gaatctccac cggactttg
11881  gtaagttccg gcatgtctag gccctcccag gtcaacttgg tatttcactc tagttccagt
11941  cacctggggg aacaaggacc cctggctcct ggttgagtcc cttcctctct tctctttttct
12001  ttctttaaat aagaagtcat ttgcatttag gattggtaaa atcataataa aaatactcat
12061  gtactgtttt tatgtgccag gcactattct aactacttta caaaaacgtt atcttattct
12121  gtttaactcc ttatgcacat gatctctctt tcaggaatg ccaaaacaga ggtaaataga
12181  tcgtttacac gtaaacctga tgtctggttg gggaggtgaa acaaacagaa acaagacaca
```

FIG. 18E

```
12241  actgtatcac ctgtacttat atttctgctt tacaaactca ggatgtttcc atgagtacag
12301  aacatgacta atcagagaag acctcataga ggaatagaaa agccaccaag ccccactagg
12361  aattgacccc tcaaggacat ggtttctagc cttttgttc actgcagatt gcccaatgcc
12421  taaagataat ggcaacagaa gagcacccaa atatttgtta gataaatgtt gcagacacta
12481  gaaggtgtca ttagggcaca gatggtacct tctctgagca aacttccttc acagctcctc
12541  ctcccgaggc tgtaggtgac tctactcttg tcacctggca cacagagttc tatcgtacga
12601  tttaggaaat tagaccagtg tgtggaccac acacacacac atctttacac acccaaagag
12661  gaggaatagt atctttgttt tggaggactt gactatgaaa ggtcttaact cctttttgta
12721  ccatgaatct ctctggcact ccagtgaagt ctaaaggacc cctttgcaga atgtttttaa
12781  atatacacat aaaatagaac acataggatt gcaaaaacaa tcattgtact aaaatacagt
12841  tatcaaccga taatcacatt tgtgatatag taacataaat gtttcttttt ttttttttg
12901  gaggcagagt ttggctcttg tcacccaggc tggagtgcaa tggcgcgatc taggctcact
12961  gaaacctctg cctcccgggt tcaagcgatt ctcagcctcc tgagtagctg ggattacagg
13021  tgccgccac cacacccagc taatttttgt atttttagta gagactaggt ttcaccaggt
13081  tggccaggct ggcctcgaac tcctgacctc aggtgatcca cctgccttgg cctcccaaag
13141  tgctgggatt acgggcatga gccaccgtgc ccggcctaaa atatttcttt agccaaagta
13201  atacattaag taatgtagca gcaagtctaa taacctgtaa tttcttcctt tcttttctttc
13261  tttcttttt tttgagatga agtttttttg agatggagtg caatggcaca atctcggctc
13321  actgcaacct ccacctcctg ggttcaagcg attctcctgc ctcagcctcc caagttgctg
13381  gaactacagg cgcatgccac catgcccagc taatttttgt atttttagta gagacggggt
13441  ttcaccatgt tggccaggct ggtcttgaac ccctgacctc aggtgatctg cctgccttgg
13501  cctccaaag tgctgggatt acaggcatga gccaccaggc ccagcccaat aacctttaat
13561  ttcaacatac taataaacat aaacagtatt tcaagatttc tgcaataact ctaatgggaa
13621  tgaaaacatc tgtggcttcc attggtaatt aagtcacagg tactgctcat attgtggtta
13681  gttgtaaaat gttttggttt gttttgtttt ttccaagact tgggggaatg ggtgttggtg
13741  ggatcaacaa gagtcttgct ctgtggccca ggctggagtg caggggcagg atcttggctc
13801  actgcaacct ccgcctccca ggttcaagcg attctcctgc ctcagcctcc tgagtagctg
13861  gcattacagg catgtgccac cacgcccagc taatttttac atttttagta gagatggggt
13921  ttcaccatgt tggcctggct ggtcttgaac tcttggcctc atgatccacc cgtctcggac
13981  tcccagagtg ttgggattac aggcatgagc caccacacct ggcagttgtt acatttttaa
14041  tgaaagaaaa tgttaaatcc agttattgaa aataaggagg cagtacttt ctcatccaag
14101  ttcatggact ttctgaattt tgtcccaga gtcctttggt gttctaggac cccaggttaa
14161  ggaacccaaa aagacaggtg ggtgggcat gagggggaac acatgttaat ccctgtttgt
14221  tctggtgaac aattcagatc cccactttct gagggtgccc tgctggaaga taaccctgtt
14281  tgtaattgtg ccggttcttg gaccttggt tgccttgatc atctgctaca actggctaca
14341  tcgaagacta gcaggtgcag tggctgggca gcaggcaaga ccaccaaata gtgggggacc
14401  aagtcagctc tgaatgggaa gccaaaagag aatagaacca ggactcaaga ttaggggagc
14461  tgggatttcc ttattcctct gtccccatgc caacccag gctcttctga gaactgtga
14521  agagaaccac ttactggatc tgtgggatcc cccagtggaa agggcagtgt gggtcactcc
14581  aaatgtccat agggaggatg tggggaaggt gctattcatc ttccactaat cacatatttg
14641  tttcttttg ttcagggc aattccttga agagctacgt aagttctctt ctctctgtta
14701  taagcagaga ataaaaagcc aggaaaggga gacagaagca acaagaggaa gaggcgggct
14761  attgagggat cacattccca gaggaaagga ggagctggag agcctgggtg gagggaagac
14821  tcctcctggg aggtagaggg caaagaagcc agctgttaga gacacattta caggtggcag
14881  agaagctgga ggcactccta tctgccacct gatccattcc tccttcactg cccctaagca
14941  ggaatccaac cctagctggt tcattgccc attccacagc aactgcccag tgcctcacct
15001  ctcagatcaa ccattgaggc aggaatggag acaagatgac cccaagggct ttcttctcc
15061  ctagttcaat ggttttatga tacaaactac tgacatacgt ttttcaagtt attttctcct
15121  tcttctagga aatcccttct gagtgatgtc acatcttggc aggggtggag gagagcctgg
15181  ttgcccaggg atttgtcctt ggggacatct catccatcaa gttgcacact cactggcatc
15241  tttgctatgg ggacattcca atttgcactt tcaggaacac tctgaattcc aagtagaatt
```

FIG. 18F

```
15301  gatttccctt cttctgtcat ctaccttttc tcttcatttt cccatttttta ttacccttct
15361  ttccatttct ctctccagtc ttccacctgg aagccctctc tggctaagga caggcaggtg
15421  cccctctctc catcagagga cacctgtact ggagagcaac acaggatggt ctctgccatg
15481  aactggaggc caggaatctc ctcactgaaa attacagtat ggtaactttg caaatggtgg
15541  ttgtttcttc caagactcca gccctgattg cgcaaaactg aaaggcatgt gaagggaagg
15601  aagaggaaga gtgcaaaaca ttgaagagag agctgagtga gctgaagagt gaggatatga
15661  gtagccccaa cccaaacctg gagatgggga gaaacctaca gaatactagc cagagctcct
15721  ccttgtcttg gcagcctact agggacctgg ggaagcaaaa acgaaagctg ggcaacatgc
15781  ctgctttaga atgttttcct tctacttaca catcttccac aggtctcaga atctttcctt
15841  cctctcatcc ttttctccta tctacatatc tatcagagta tccactgttt attcaacaac
15901  tactacttga tggtcagaca caaacaaaca agctaggtgc taattaataa agatacgagt
15961  tttggccggg tgcggtggct cacgcctgta atcccagcac tttgggaggc cgaggcgggc
16021  gaatcacgag gtcaggagtt caagaccagc ctggccaaca tggtgaaacc ccatctctac
16081  taaaaataca aacaattaac tgagcatagt ggtgggcacc tataatacca gctactccgg
16141  aggctgaggc aggagaatcg cttgaaccca ggaggcagag gttgcagtga gctgagatcg
16201  cgccactgca ctctagccgg agtgacagag taagactctg tctcaaaaat aaataaataa
16261  ataaataaat aaataaataa ataaataaaa aataataata caagttttca taagcacact
16321  tctaaccct tgtcttttat gtatttcctt ccttatccac gcacctgtct ccctctactc
16381  cagcctcatt accccagagg tcagtcctca ggaaaactaa acacaaagaa agagctcagt
16441  cagaaaggcc atttatttat gtttcaagat gctcactgcc tcctttgttt tgtctccttt
16501  gcaggccttc tctcttaggc ctcttctcct gggggtatgg atcctggggg gagattgatc
16561  acctccatgc ttccattcct ccccagccat agtggggaca tcatgagaga agccaagcca
16621  ctggcccagg atcacccggc atttatggtg gctgctctgg cacaggtcct tgcctttata
16681  gcccctccag tgatccataa ggccctcttt ctccccaaag gagaggtcac agatagggca
16741  aaggtagctc ttctgcttcc agtgggtctg ctggtgtctg accagcctgg aaaatgagct
16801  gaaagacttg ctgcaatgga agcagtagtt gggcggctct gtgaggtggc ccttctggtg
16861  tctggagaga taggatttct tgctaaaagt caaagaacaa tgggggcaac agaagacatt
16921  gagtcttgag ggcttcactg gatgagagtt ggatctggca tcctgacaga gggttccagt
16981  gatgggtgcc tgggtcctgg tcacaggtgc ttggttctta agtacagatg cctggttctg
17041  ggccatagga ccctcagttc taaatatggg ttcctgggac ctggccactg gtgcatggtt
17101  cacatccaaa agccctggga tggacctctg gcttctggcg atgggtgtct ggaattcagc
17161  ctgggtgcct ggaatcctca aagtacactc ctggtttcca tccactggct cctggttttg
17221  gtgtatcttc tggtggcgtt tgagctcaga ctggtcccgg aagctcttcc cacacacaga
17281  gcatgaatgg ggccggtaac ccagatggac gcggcggtga cgacttagtc cagaagcatc
17341  acagtaggtc ttgtcacaga gcgtgcaaca gaagggcctc tccccaagat gcatgcgtct
17401  gtgatagctg agggacttgg ggctccgaaa caacttccca cactgactgc agctgttagt
17461  cagcttggga ttgtgaacaa actggtggct atagaggtag gagcgcctgc tgaaacattt
17521  ggcacaggtg tagcaaaa
```

FIG. 19

```
  1    tttgtatgtc attgcaggat tcatgctttc cagtgtgtca tctatggaac tgcctctttc
 61    ttcttccttt atggggccct cctgctggct gagggcttct acaccaccgg cgctgtcagg
121    cagatctttg gcgactacaa gaccaccatc tgcggcaagg gcctgagcgc aacggtaaca
181    gggggccaga aggggagggg ttacagaggc caacatcaag ctcattcttt ggagcgggtg
241    tgtcattgtt tgggaaaatg gctaggacat cccgacaagg tgatcatcct caggattttg
301    tggcaataac aagggggtggg gggacaa
```

FIG. 21

```
  1    masqkrpsqr hgskylatas tmdharhgfl prhrdtgild sigrffggdr gapkrgsgkd
 61    shhpartahy gslpqkshgr tqdenpvvhf fknivtprtp ppsqgkgrgl slsrfswgae
121    gqrpgfgygg rasdyksahk gfkgvdaqgt lskifklggr dsrsgspmar r
```

FIG. 22

```
  1    mglleccarc lvgapfaslv atglcffgva lfcgcgheal tgtekliety fsknyqdyey
 61    linvihafqy viygtasfff lygalllaeg fyttgavrqi fgdyktticg kglsatvtgg
121    qkgrgsrgqh qahslervch clgkwlghpd kityaltvvw llvfacsavp vyiyfntwtt
181    cqsiafpskt sasigslcad armygvlpwn afpgkvcgsn llsicktaef qmtfhlfiaa
241    fvgaaatlvs lltfmiaaty nfavlklmgr gtkf
```

FIG. 23

```
  1    maslsrpslp sclcsfllll llqvsssyag qfrvigprhp iralvgdeve lpcrispgkn
 61    atgmevgwyr ppfsrvvhly rngkdqdgdq apeyrgrtel lkdaigegkv tlrirnvrfs
121    deggftcffr dhsyqeeaam elkvedpfyw vspgvlvlla vlpvlllqit lglvflclqy
181    rlrgklraei enlhrtfdph flrvpcwkit lfvivpvlgp lvaliicynw lhrrlagqfl
241    eelrnpf
```

FIG. 20

```
   1 ctgtatcagt gctcctcgtc gcctcactgt acttcacgga agagacttgg ttgactggcc
  61 acttggagcg gaatcaggag acattcccaa ctcagagaga ctgagcccta gctcgcccac
 121 ttgctggaca agatgatatt ccttaccacc ctgcctctgt tttggataat gatttcagct
 181 tctcgagggg ggcactgggg tgcctggatg ccctcgtcca tctcagcctt cgagggcacg
 241 tgtgtctcca tccctgccg tttcgacttc ccggatgagc tcagaccggc tgtggtacat
 301 ggcgtctggt atttcaacag tccctacccc aagaactacc cgccagtggt cttcaagtcc
 361 cgcacacaag tggtccacga gagcttccag ggccgtagcc gcctgttggg agacctgggc
 421 ctacgaaact gcaccctgct tctcagcacg ctgagccctg agctgggagg gaaatactat
 481 ttccgaggtg acctgggcgg ctacaaccag tacaccttct cggagcacag cgtcctggac
 541 atcatcaaca ccccaacat cgtggtgccc cagaagtgg tggcaggaac ggaagtagag
 601 gtcagctgca tggtgccgga caactgccca gagctgcgcc tgagctgag ctggctgggc
 661 cacgagggc taggggagcc cactgttctg ggtcggctgc gggaggatga aggcacctgg
 721 gtgcaggtgt cactgctaca cttcgtgcct actagagagg ccaacggcca ccgtctgggc
 781 tgtcaggctg ccttccccaa caccaccttg cagttcgagg gttacgccag tctggacgtc
 841 aagtaccccc cggtgattgt ggagatgaat tcctctgtgg aggccattga gggctcccac
 901 gtcagcctgc tctgtggggc tgacagcaac ccgccaccgc tgctgacttg gatgcgggat
 961 gggatggtgt tgagggaggc agttgctgag agcctgtacc tggatctgga ggaggtgacc
1021 ccagcagagg acggcatcta tgcttgcctg gcagagaatg cctatggcca ggacaaccgc
1081 acggtggagc tgagcgtcat gtatgcacct tggaagccca cagtgaatgg gacggtggtg
1141 gcggtagagg gggagacagt ctccatcctg tgttccacac agagcaaccc ggaccctatt
1201 ctcaccatct tcaaggagaa gcagatcctg gccacggtca tctatgagag tcagctgcag
1261 ctggaactcc ctgcagtgac gcccgaggac gatggggagt actggtgtgt agctgagaac
1321 cagtatggcc agagagccac cgccttcaac ctgtctgtgg agtttgctcc cataatcctt
1381 ctggaatcgc actgtgcagc ggccagagac accgtgcagt gcctgtgtgt ggtaaaatcc
1441 aacccggaac cctccgtggc ctttgagctg cctccccgca acgtgactgt gaacgagaca
1501 gagagggagt ttgtgtactc agagcgcagc ggcctcctgc tcaccagcat cctcacgctc
1561 cggggtcagg cccaagcccc accccgcgtc atttgtacct ccaggaacct ctacggcacc
1621 cagagcctcg agctgccttt ccaggagca caccgactga tgtgggccaa aatcggccct
1681 gtgggtgctg tggtcgcctt tgccatcctg attgccattg tctgctacat cacccagaca
1741 agaagaaaaa agaacgtcac agagagcccc agcttctcag cgggagacaa ccctcatgtc
1801 ctgtacagcc ccgaattccg aatctctgga gcacctgata agtatgagag tgagaagcgc
1861 ctggggtccg agaggaggct gctgggcctt agggggggaac ccccagaact ggacctcagt
1921 tattcccact cagacctggg gaaacgaccc accaaggaca gctacaccct gacagaggag
1981 ctggctgagt acgcagaaat ccgagtcaag tga
```

SPD females (n=5), 50mm T9 contusion, CFA 1mg/ml after the contusion, boost with IFA 7 days later.

t-test: *P< 0.05, **P<0.01
compared to Nogo+CFA

SEQUENCE LISTING

```
<160> NUMBER OF SEQ ID NOS: 29

<210> SEQ ID NO 1
<211> LENGTH: 612
<212> TYPE: DNA
<213> ORGANISM: Homo sapiens

<400> SEQUENCE: 1
ccaagaagat cccacagcag cttccgaagg cctggatgtg atggcatcac agaagagacc      60
ctcacagcga cacggatcca agtacttggc cacagcaagt accatggacc atgcccggca     120
tggcttcctc ccaaggcaca gagacacggg catccttgac tccatcgggc gcttctttag     180
cggtgacagg ggtgcgccca agcggggctc tggcaaggac tcacacacaa gaactaccca     240
ctacggctcc ctgccccaga agtcgcagag gacccaagat gaaaacccag tagtccactt     300
cttcaagaac attgtgacac ctcgtacacc ccctccatcc caaggaaagg ggagaggcct     360
gtccctcagc agatttagct ggggaggaag agacagccgc tctggatctc ccatggcaag     420
acgctgagag cctccctgct cagccttccc gaatcctgcc ctcggcttct taatataact     480
gccttaaacg tttaattcta cttgcaccaa atagctagtt agagcagacc ctctcttaat     540 cccgtgggc tgtgaacgcg gcgggccagc ccacggcacc ctgactggct aaaactgttt      600 gtccctttt at                                                          612

<210> SEQ ID NO 2
<211> LENGTH: 2139
<212> TYPE: DNA
<213> ORGANISM: Homo sapiens

<400> SEQUENCE: 2
gaaaacagtg cagccacctc cgagagcctg gatgtgatgg cgtcacagaa gagaccctcc      60
cagaggcacg gatccaagta cctggccaca gcaagtacca tggaccatgc caggcatggc     120
ttcctcccaa ggcacagaga cacgggcatc cttgactcca tcgggcgctt ctttggcggt     180 gacagggtg cgccaaagcg gggctctggc aaggactcac accaccggc aagaactgct      240 cactatggct ccctgcccca gaagtcacac ggccggaccc aagatgaaaa ccccgtagtc     300
cacttcttca agaacattgt gacgcctcgc acaccacccc gtcgcagggg aaggggagaga     360 ggactgtccc tgagcagatt tagctggggg gccgaaggcc agagaccagg atttggctac     420
ggaggcagag cgtccgacta taaatcggct cacaagggat tcaagggagt cgatgcccag     480
```

-continued

```
ggcacgcttt ccaaaatttt taagctggga ggaagagata gtcgctctgg atcacccatg      540
gctagacgct gaaaacccac ctggttccgg aatcctgtcc tcagcttctt aatataactg      600
ccttaaaact ttaatcccac ttgcccctgt tacctaatta gagcagatga cccctcccct      660
aatgcctgcg gagttgtgca cgtagtaggg tcaggccacg gcagcctacc ggcaatttcc      720
ggccaacagt taaatgagaa catgaaaaca gaaaacggtt aaaactgtcc ctttctgtgt      780
gaagatcacg ttccttcccc cgcaatgtgc ccccagacgc acgtgggtct tcaggggcc       840 aggtgcacag acgtccctcc acgttcaccc ctccacccctt ggactttctt ttcgccgtgg     900
ctcggcaccc ttgcgctttt gctggtcact gccatggagg cacacagctg cagagacaga     960
gaggacgtgg gcggcagaga ggactgttga catccaagct tcctttgttt ttttttcctg     1020
tccttctctc acctcctaaa gtagacttca ttttttcctaa caggattaga cagtcaagga    1080
gtggcttact acatgtggga gcttttggt atgtgacatg cgggctgggc agctgttaga      1140
gtccaacgtg gggcagcaca gagaggggc cacctcccca ggccgtggct gcccacacac      1200
cccaattagc tgaattcgcg tgtggcagag ggaggaaaag gaggcaaacg tgggctgggc     1260
aatggcctca cataggaaac agggtcttcc tggagatttg gtgatggaga tgtcaagcag     1320
gtggcctctg gacgtcaccg ttgccctgca tggtggcccc agagcagcct ctatgaacaa     1380
cctcgtttcc aaaccacagc ccacagccgg agagtccagg aagacttgcg cactcagagc     1440
agaagggtag gagtcctcta gacagcctcg cagccgcgcc agtcgcccat agacactggc     1500
tgtgaccggg cgtgctggca gcggcagtgc acagtggcca gcactaaccc tccctgagaa     1560
gataaccggc tcattcactt cctcccagaa gacgcgtggt agcgagtagg cacaggcgtg     1620
cacctgctcc cgaattactc accgagacac acgggctgag cagacggccc ctgtgatgga     1680
gacaaagagc tcttctgacc atatccttct taacacccgc tggcatctcc tttcgcgcct     1740
ccctccctaa cctactgacc cacctttttga ttttagcgca cctgtgattg ataggccttc    1800
caaagagtcc cacgctggca tcaccctccc cgaggacgga gatgaggagt agtcagcgtg     1860
atgccaaaac gcgtcttctt aatccaattc taattctgaa tgtttcgtgt gggcttaata     1920
ccatgtctat taatatatag cctcgatgat gagagagtta caaagaacaa aactccagac    1980
acaaacctcc aaattttttca gcagaagcac tctgcgtcgc tgagctgagg tcggctctgc    2040
gatccatacg tggccgcacc cacacagcac gtgctgtgac gatggctgaa cggaaagtgt    2100
acactgttcc tgaatattga aataaaacaa taaacttttt                          2139
```

<210> SEQ ID NO 3
<211> LENGTH: 581
<212> TYPE: DNA
<213> ORGANISM: Homo sapiens

<400> SEQUENCE: 3

```
taatatctag ggktttgact ctgacccgtg ttggggctct cacttcatgg cttctcacgc       60
ttgtgctgca tatcccacac caattagacc caaggatcag ttggaagttt ccaggacatc      120
ttcattttat ttccaccctc aatccacatt tccagatgtc tctgcagcaa agcgaaattc      180
caggcaagcc ttagggaaaa aaggaaaaac aaagaaaatg aaacaattgg cagtgaaagg      240
cagaaagaga agatggagcc cttagagaag ggagtatccc tgagtaggtg gggaaaaggg      300
gaggagaagg ggaggaggag aggaggagga agcaggcct gtcccttaa gggggttggc       360 tgtcaatcag aaagccctt tcattgcagg agaagaggac aaagatactc agagagaaaa      420
```

```
agtaaaagac cgaagaagga ggctggagag accaggatcc ttccagctga acaaagtcag    480
ccacaaagca gactagccag ccggctacaa ttggagtcag agtcccaaag acatgggtaa    540
gtttcaaaaa ctttagcatt gaagattcaa gaggacacag g                        581
```

<210> SEQ ID NO 4
<211> LENGTH: 1762
<212> TYPE: DNA
<213> ORGANISM: Homo sapiens

<400> SEQUENCE: 4

```
ctgctttcag agcctgtgac ttcttgtgtg cctctcctgt ttctcagcaa catggcatag     60
ggcctgggat accaggtctg gggatctcag ggactcttag cactttaaga cacatgtgtt   120 cccaggcect ggtgtgttcc tctagtgcca gaaagatgtt tcatgctttg ctgactttgt   180
ataaagtctg tttgtagctg ttttgacaga atctcagcgt ataactgagg gtggggacat   240
tagccaagct gcattatagg aggacaaaac tgccatacaa agtgtccaaa atcattaagc   300
ctgcattttt attattggga gtaatatcaa acctcctatt ttccaatttt catttcttgt   360
cctgtgctag ctccatcctg tttggactgc tcctcccata tgtaaactaa gaagaatcaa   420
gcattctttg caacaaatac acacgatgct caaaaatgtc caggagcatc caatttccaa   480
agtttcctcc acctggaatg ctcttcatgc taaaatcctg tctgacaata ccagcatctc   540
tggcctgcac tcatcccttc ctggaactcc aagtgcattt accctctgtt accacttact   600
tggctgcctg aattgttagt tgaaatatt aggtctactt agctaattct tcctcaggaa   660
attaaagact cccatatggc agagtctgtg tcttttctct cttcatatcc cgtataacac   720
ccagcataat gctgggcata tagtgagtat tccataaata gttgatgaat gactaaaata   780
agcaagcaaa caaacagact agaacaataa gaaagaaggg actggatttc ataatctctc   840
tggcttgcta tttgaattgc tgaattatta ttatttatta aatattttt aaattctggc   900 aataaaaggt aaggatttat tttctttctt tcttttttt tttcttgaga cagagtctcg   960
ctcttactgc ccaggctgga gtacaatggc gcaatcttgg ctcacggcaa cctccgcctc  1020
ctcctgggtt aacagattc tcctgtctca gcctcctgag tagctgggat tacaggcata  1080 cgccatgcc cggctaattt ttgtattttt agtagagacg gggttttgcc atgttggcca  1140
ggctggtctt gaactcctga cctcatgtga tccacctgcc tcagcctccc aaagtgctgg  1200
gattacaggc atgcgccacc gtgcccggcc aaagatttat tttcaagaat gaaacaaagt  1260
aaggattctg ggtcaatctc acatgctgaa agccaaaacc tctagccgct cctgcttttt  1320
gacttcggag tgcccactat ctccgagcct gtgagcacag ggcctggcag aggggtttga  1380
gtggcatgag ctacctactg gatgtgcctg actgtttccc cttcttcttc cccaggcttg  1440
ttagagtgct gtgcaagatg tctggtaggg gccccctttg cttccctggt ggccactgga  1500 ttgtgttct ttggggtggc actgttctgt ggctgtggac atgaagccct cactggcaca  1560
gaaaagctaa ttgagaccta tttctccaaa aactaccaag actatgagta tctcatcaat  1620
gtgtaagtac ctgccctccc acacagaccc atctttttt tccctctctc catcctggag  1680
atagagaact cttcagtacc ttagtaacta gcaggggact ggggtggagc cagaccggat  1740
tcccgagtct tccctctgtg ca                                            1762
```

<210> SEQ ID NO 5
<211> LENGTH: 828
<212> TYPE: DNA
<213> ORGANISM: Homo sapiens

<400> SEQUENCE: 5

```
ctagaaaatc cctagccttg ttaaggtgct cgctctggtg tatacctcac ttatgtcggg      60
aaagaagcca ggtcttcaat taataagatt ccctggtctc gtttgtctac ctgttaatgc     120
aggatccatg ccttccagta tgtcatctat ggaactgcct cttctcttc ctttatggg      180
gccctcctgc tggctgaggg cttctacacc accggcgcag tcaggcagat ctttggcgac     240
tacaagacca ccatctgcgg caagggcctg agcgcaacgg taacagggggg ccagaagggg     300
aggggttcca gaggccaaca tcaagctcat tctttggagc gggtgtgtca ttgtttggga     360
aaatggctag gacatcccga caaggtgatc atcctcagga ttttgtggca ataacaaggg     420
gtggggaaa attgggcgcg agtctgtggc ctcgtcccca cccaaggctg ggtcctctct     480
aggggcctgg catttgagtg aggaagcgat ggctgcagcc gaacgagaag gtcaggaaga    540
acgtggtgcc cagctggctt agcctcacct ttcaaaggtt ccctaagcaa atttcttctc    600
aaaacagaaa gcatgagttt tgtgggatgc tttgtacaat cagaccattt ctaagccatc    660
tgttggtatc cctttgttcc cttcctagta ggtaccacaa gagtggatct aactggacaa    720
gagtctaaaa tgctgctcat gtgattgaga cttgggcacc tgagctraga gggaggatgg   780
ataataaaaa ttaataata actccaaggt aaatttacaa tgttctgg                 828
```

<210> SEQ ID NO 6
<211> LENGTH: 1140
<212> TYPE: DNA
<213> ORGANISM: Homo sapiens

<400> SEQUENCE: 6

```
gatcctcctc attcttcccc tacccattcc ccccaccctc cgttatactg gggccagtta      60
tctagtagat actgccaatt acccttggca gaggtgccct gctcactaat tttatttggg    120
ggagmgccct ggaacctggt tttaatgtct ggcacacgcc acttccagga tctcccagtt    180
tgtgtttcta catctgcagg ctgatgctga tttctaacca acccatgtca atcattttag    240
tttgtgggca tcacctatgc cctgaccgtt gtgtggctcc tggtgtttgc ctgctctgct    300
gtgcctgtgt acatttactt caacacctgg accacctgcc agtctattgc cttccccagc    360
aagacctctg ccagtatagg cagtctctgt gctgatgcca gaatgtatgg tgagttaggg    420
tacgggtgct ttggctctcc tacccactat ggaagcacta tatatttggt tattttctta    480
gtgtaaggag ggtggtgatt atgagaaaaa tataagatga tgaatgattg ggtcttagtt    540
tattaatcct tccctactga aaccagagag gtttcttccc ccggaaggga acttggaagt   600
ggtgggagtt tccttggcca ttcacattgg cctactctag ttgactgctg ttcacaaccc   660
caaagcagca catttcaata acaaacacaa ggttdsacca ctgttcaata ccaccttctc    720
tttttttgtaa acctgtagaa aagaggatcc taattgttgg tagmatccaa mtttacagcc   780
aggataatta gagatggaag aagggctctg ggggaaagtc tccatgtggc cccgtaactc    840
cataaagctt accctgcttg cttttttgtgt cttacttagg tgttctccca tggaatgctt    900
tccctggcaa ggtttgtggc tccaaccttc tgtccatctg caaacagct gaggtgagtg    960
ggttatttgg gttatttttac aagggagtag ctaataccat acaaattaca cccatggcct  1020
tcaattttaa ggactgaaag tttcccttttg ctggattttg aattagccga ttgccttcta 1080
caacatgttg gctaagtgtg cctgagccaa tgagcataga aggtaaaaca cctcttttct  1140
```

<210> SEQ ID NO 7

```
<211> LENGTH: 295
<212> TYPE: DNA
<213> ORGANISM: Homo sapiens
<220> FEATURE:
<221> NAME/KEY: misc_feature
<222> LOCATION: (42)..(43)
<223> OTHER INFORMATION: n at positions 42 and 43 is unknown

<400> SEQUENCE: 7
aattagcaca cagaaaggat atccaacaca tacaaagctg tnntcatgga ctacactgga      60
gcatattact gctgttgcaa gaaacatttc ttcttcctct tttcatttc ctgcagttcc     120
aaatgacctt ccacctgttt attgctgcat ttgtgggggc tgcagctaca ctggtttccc    180
tggtgagttg actttgaatg atcttggcaa gtaaataggc ctgagatagt tgtgggtaca    240
gctattctga aaggcaagaa ggtagactgc ttccatcctt gaaatgctgg aggga         295

<210> SEQ ID NO 8
<211> LENGTH: 2940
<212> TYPE: DNA
<213> ORGANISM: Homo sapiens

<400> SEQUENCE: 8
aattctatat actatcacta tggctccact ttggatactc tccagtggat ttagttactc      60
atatggaaat acctgggagg acctcctaac attattagaa ttgttatgat tataatacaa     120
ygctatgtcc caggtcttgc tgatagtgct acagtgccct gtgaatgtag tgtgctcatt     180
gtgcagatta aaaacctaag gcactgaagg gtgaagtgat ttatctgaag ttattttata    240
aagcagtgat cagacaasct gagctcacag aactccctgg cccctactgc tgaggtttcc    300
atacagagtc aagtaatttc tcaccttgta aaacgaattg attcattaac caggggagag    360
ctctactgca tgatgtggct gtgtgtctac agcaagcacc ctatgactct aagtcactcg    420
gacatattga tgtggcaaag cccaaatatt gttcacttcc ctgaggaaaa ctcagtgcta    480
gatcaaacag aggtgtggaa taaatcttta tgatttgatt ctctgggcct gggccatgag    540
acccatgatg cctcagagac atcgacttc cagtcaagtg tatatggaga aagccaagcc    600
tgggatgtac tgcttttgc agagcatggg ttttcccctt atttagttat gatttattt      660
ctacccttcc tcattcccaa agggatttga ggagggagtg ctttctttt tactctcatt    720
cacattctct cttctgttcc ctacagctca ccttcatgat tgctgccact acaactttg    780
ccgtccttaa actcatgggc cgaggcacca agttctgatc ccccgtagaa atcccccttt    840
ctctaatagc gaggctctaa ccacacagcc tacaatgctg cgtctcccat cttaactctt   900
tgccttttgcc accaactggc cctcttctta cttgatgagt gtaacaagaa aggagagtct   960
tgcagtgatt aaggtctctc tttggactct cccctcttat gtacctcttt tagtcatttt  1020
gcttcatagc tggttcctgc tagaaatggg aaatgcctaa taatatgact tcccaactgc  1080
aagtcacaaa ggaatggagg ctctaattga attttcaagc atctcctgag gatcagaaag  1140
taatttcttc tcaaagggta cttccactga tggaaacaaa gtggaaggaa agatgctcag  1200
gtacagagaa ggaatgtctt tggtcctctt gccatctata ggggccaaat atattctctt   1260
tggtgtacaa aatggaattc attctgcgtc tctctattac actgaagata gaagaaaaaa   1320
gaatgtcaga aaaacaataa gagcgtttgc ccaaatctgc ctattgcagc tgggagaagg   1380
gggtcaaagc aaggatcttt cacccacaga aagagagcac tgaccccgat ggcgatggac   1440
tactgaagcc ctaactcagc caaccttact tacagcataa gggagcgtag aatctgtgta   1500
gacgaagggg gcatctggcc ttacacctcg ttagggaaga gaaacagggt cttgtcagca   1560
```

```
tcttctcact cccttctcct tgataacagc taccatgaca accctgtggt ttccaaggag    1620
ctgagaatag aaggaaacta gcttacatga gaacagactg gcctgaggag cagcagttgc    1680
tggtggctaa tggtgtaacc tgagatggcc ctctggtaga cacaggatag ataactcttt    1740
ggatagcatg tctttttttc tgttaattag ttgtgtactc tggcctctgt catatcttca    1800
caatggtgct catttcatgg ggtattatcc attcagtcat cgtaggtgat ttgaaggtct    1860
tgatttgttt tagaatgatg cacatttcat gtattccagt ttgtttatta cttatttggg    1920
gttgcatcag aaatgtctgg agaataattc tttgattatg actgtttttt aaactaggaa    1980
aattggacat taagcatcac aaatgatatt aaaaattggc tagttgaatc tattgggatt    2040
ttctacaagt attctgcctt tgcagaaaca gatttggtga atttgaatct caatttgagt    2100
aatctgatcg ttcttctag ctaatggaaa atgatttac ttagcaatgt tatcttggtg    2160
tgttaagagt taggtttaac ataaaggtta ttttctcctg atatagatca cataacagaa    2220
tgcaccagtc atcagctatt cagttggtaa gcttccagtc atcagctatt cagttggtaa    2280
gcttcccagg aaaaaggaca ggcagaaaga gtttgagacc tgaatagctc ccagatttca    2340
gtcttttaat gttttgtta actttgggtt aaaaaaaaa aaagtctgat tggttttaat    2400
tgaaggaaag atttgtacta cagttctttt gttgtaaaga gttgtgttgt tctttteece    2460 caaagtggtt tcagcaatat ttaaggagat gtaagagctt acaaaaaga cacttgatac    2520 ttgtttccaa accagtatac aagataagct tccaggctgc atagaaggag gagagggaaa    2580
atgttttgta agaaaccaat caagataaag gacagtgaag taatccgtac cttgtgtttt    2640 gttttgatt aataacataa caaataacca acccttccct gaaaacctca catgcataca    2700
tacacatata tacacacaca aagagagtta atcaactgaa agtgttcctt catttctgat    2760
atagaattgc aatttttaaca cacataaagg ataaacttttt agaaacttat cttacaaagt    2820
gtattttata aaattaaaga aaataaaatt aagaatgttc tcaatcaaac atcgtgtcct    2880
ttgagtgaat tgttctattt gacttcacaa tagaaactta ataatcgtac cttctcaaga    2940

<210> SEQ ID NO 9
<211> LENGTH: 17538
<212> TYPE: DNA
<213> ORGANISM: Homo sapiens

<400> SEQUENCE: 9
atggaaatgt tctgtatttg tgttgtctga tgagataacc actaactgta gtgctattga      60
gcatttgaaa catggctagt gtaatcaatg aaccaaattt ttaatttat ttaattgtaa     120 ttaattttaa gtggccacat gcagggagtg actgctgcat tggacagcac ggctctaaat     180
tgagcctttt ttccttattt ggtgaggcat acttgcctta agattgggaa gtctattttt     240
ggaacctgct accaatgctg gtctcacact tgcaattctc agctgagcca agaggtgaga     300
gaaaggtcat tttccattcc aagatctcac tctccctgt gacactgagg aaactggcaa     360
gtgatgtgaa ggctggagag cgtgtcctgt atgctggctc tgtcccttct gcctgtgttg     420
actgacatag ttagttgctg cccttgctgg tctcccttcc tccaaccttg cctctctgag     480
cacacctgac attcatctca tgacttccct aaaaacattc tttgggaaca agaaactaac     540
aaatcccaag tgacctatca catatacaaa catacagggc agagtttgga ttcgcggtag     600
aagaagggga ggttagacat taagaagaat ggtctggtga tgacagttgt gagataaatg     660
aaacaggaaa aagaaatcta agttttcttt cttttttttaa gaaccaataa taatttctct     720
```

```
cttttgacta gtcagtaggg ctggggtgga ttggaggaag cttacatatt ccatgaacaa    780
gcctcttcct aaggtcctgt aagtgatcct gccccactga ttagcccct a gaagacccctt   840 caaaggttgg atctccagga gggagtgggg gaggaaagcc ctgtaccagg cagcctctgc    900
tccattgctc tgggggggtg gggaagacaa accctggtca tcccctcagt ctgtagccct    960
tttgtgtgag tgcctggcaa gggtgacgtg gggctgtttc tgcgggcaca gctgcagcaa   1020
ttaccggagt ggaggcaggg cccaggcagc actgccctcc aagatcttcc cttgggcttt   1080
tcagcagtaa ggggacatgc accccaaggg cctccacttg gcctgacctt gctgcggggg   1140
ctctctgtcc ccaggaacag tagagatggc aagcttatcg agaccctctc tgcccagctg   1200
cctctgctcc ttcctcctcc tcctcctcct ccaagtgtct tccagctatg caggtaagac   1260
atgttttttt tcctgccctg gggagaccct gaaaacagaa aggctagttt cctgggggtt   1320
agctccttca acatcctca agttggtata ttatctttct aaaacataga cctactgaca   1380
tgcctccctt cctcagaaac cttccgtggg tggttcttac agccttcaag atggagtcca   1440
gactcttttt ttttttttggg acagagtctc cctctgttgc tcaggctgga gtgcagtggc   1500
atgatctcgg ctcactgcaa cctcagcctc cctggttcaa gcgattctcc tgacttggcc   1560
tcccaagtag cggagactac aggcgcctgc caccacaccc agctaaattt gttcttttct   1620
ttcttttttt ttttttttgg gatttttagga cagacggggt ttcacatgtt ggccaggatg   1680
gtctcgatct cttgacctgc tgatccgccc gcctcagctt cccaaagtac tgggattatg   1740
ggcgtgagcc actgcactag gcctaatttt tttattttta gtagagatgg ggtttcacca   1800
tgttggccag gctggtctgg aaccctgac ctcaagtggt ctgccctcct cagcctccca   1860
aagttctgag attacaggca tgagccattg cgtctgaccc agactcctta atgtgactaa   1920
ctccaggctt tccttggact acttcttact tgtctttcca gctttgtctt ttcacctctc   1980
caattgagat aaaataataa caacctcttg gagttctcat caggattaca tgaaatgaga   2040
tatgtaacat gcttagcagt gcctgtccat agtaaatctc aataaatgtt tgtggaatta   2100
taatatcttg tcatgtttga actttgctc tgcataatca ggcaccagta ggttttttata   2160 aaggaacccg tctgtcacgt gcagaggaga aataaacaga aagtttccca tcctcaggga   2220
gccacctgac tgacagaggc acagtgcatc cactctccag gtctagggga gaaagcagcc   2280
ttatttctta gtagctcaga atctgacttg agaaacacat ccacatagaa aaaacaagg    2340 aacttttcg ggtcagggtc cgggaccac agtgaggtgg aagatacagg ggaaggaaga    2400
gggaaataga gccatcccca gggtggaaga tctcagaaga gaatttggga aacaaggtat   2460
gaacaaggac tgaatagtga gaagtgatgg agagacagct aaagtagatg gagtgtcaaa   2520
accaaaacct ctaagggtag aataggcagc aatttggcca agtcctaaca gggagcccca   2580
taggaggatt caacctcaag atgctgtgcc acattccaag agggaaccta aaggctgggc   2640
tgaagagtca gagatggcta cagctggcaa aaagatgggc agatgctgag aggagatgat   2700
tgctaaaatg ttctgtccag gacattcaca gtatctctat aaccagagtc ttttttgtcg   2760
ttgttgttct caagaaggaa acttgaggcc gggtgtggtg gtttatgccc ataatcccag   2820
cgctttgggg ccaaggcagg cggatcacct gaggtcagga gttcgagacc agcctggcca   2880
acagtgtgaa acctcatctt tactaaaaat acaaaaatta gctggatgcg gcggtaggtg   2940
cctgtaatgc cagctactcg ggaggctgag gcaggagaat cacttgaacc tgggaggcgg   3000
aggttgcagg gaggcggagg ttgcagtgag ccaagattgc accactgcac tccagcctgg   3060
gcgacagaga gtaagactgt ctcaaaaaat aaatgaataa ataaaaagga agaagaagaa   3120
```

-continued

```
gaagaacaat tgcaatcctc cctggctcta gaatgtcatt taaaagtcga gtgtcttctt    3180
ccttccctgt tttgaagcag cccttctcat gacaggcttg cttgccaagg ttccctctga    3240
ccttaaatct cttccttttg gtgtcttgga cagggcagtt cagagtgata ggaccaagac    3300
accctatccg ggctctggtc ggggatgaag tggaattgcc atgtcgcata tctcctggga    3360
agaacgctac aggcatggag gtggggtggt accgccccccc cttctctagg gtggttcatc    3420
tctacagaaa tggcaaggac caagatggag accaggcacc tgaatatcgg ggccggacag    3480
agctgctgaa agatgctatt ggtgagggaa aggtgactct caggatccgg aatgtaaggt    3540
tctcagatga aggaggtttc acctgcttct tccgagatca ttcttaccaa gaggaggcag    3600
caatggaatt gaaagtagaa ggtgagtagt gccatataat attaggtatt aactgttggg    3660
tggccaagaa caattattct ctcaactgag atgagatccc tcaacccaaa catctcagtc    3720 ctggaatga tttccataaa aatgtacaca tcaataaaca gaaactcatg cttagggatg    3780
tctgttgcat cattattcag agtagcaagg aaattgggat caaaatcaat gcctttgagt    3840
aggtaagtga cagaatgaac aatggtagcc atactgtgaa tattatgcag ggattaaaaa    3900
gattatttta gcactaggcc agatggtttg gggggctcct ctaaggtatt attgagtgat    3960
aagagcaagc tgctgtagga tacaaaaaca aaaacaaaac cctagggcat ggtggtttgc    4020
ctcgcagcta ctcaggaggc tgagacggga ggctggcttg agcccagggg tttgcagtta    4080
cagtgagcta tgattgcacc actgcactcc aacccgggtg acagagcaaa gaccttcacc    4140
cccactccct acccgtctct aaaaaaaaca aaaacaaaaa caaaaaaacc cttgggccca    4200
gcgccgtggc tcacgcctgt aatcccagca ctgtgggagg ccgaggtggg cagatcacaa    4260
ggtcaggaga tcgagaccat cctggctaaa acggtgaaac cccgtctcta ctaaaaatac    4320
aaaaaaaaaa aaaaaattta gccaggcatg gtagcaggcg cctgtagtcc cagctactcg    4380
ggaggctgag gcaggagaat ggcgtgaacc cggaagcgga ggttgcagtg agccaaaatc    4440
cttccactgc actccagcat gggggacaca gcgagactcc gtctcaaaaa aaaaaaaaaa    4500
accctgtatt tgtgagcgca cacacacaca cacacacaca cacacctgtg cttggtccta    4560
gtgaataagc aagtaaatca aatgtctaaa tataattata gaaaggagat gtcacctttt    4620
ggctgtacct ccactatttc attctgcaga attgcagaat ttcttttttt tttccttttct    4680 ttcttttctt tttttttttg acacagagtc tcgctctgta acccaggctg gagtgcaatg    4740 gcgcccctccg cctcctgggt tcaagtgatt ctcctgcctc agcctcccga gtagctggga    4800
ttacaggtgc ccaccaccac acccagctaa ttttttgtatt tttagtagag acagggtttc    4860
accaggttgt caaggttggt ctcaaactcc tgacctcagg tgatccactc gcctcagact    4920
cccaaagtgc tgggattaca ggcatgagcc atggtgcccg gcctcagaat ttcatttca    4980 acatgttttg catgatgggt gattttggag aatattttt gctctatcgc aggatgatta    5040
agatgtggac aaggtgaagc cgatggaggg ggagctttga aagttacttg ctatttaatt    5100
gaggaactaa actgctttga gagcctgggg gtcagatcct ctgccttttc ctcctcccca    5160
cctgcagtgc aaacatcaga caattgatca ctattgtatc ttggaggtgg gagtgaccat    5220
tgcagtgctg ggaccagaag atggcattgt atgtggaaca acaaagcact atttctagag    5280
actgcctgca gggatatgga aatagcttta tgtgtctcag aatgttcttc atacagctgt    5340
ttttattggg gaaattctac ttgccgaaaa gtttgatagt gagaccctct ccagtttgca    5400 gattttctc cttcctgctc aacaacttcc tagctcagta actgcctctc ccaacaaact    5460
```

| | |
|---|---|
| ccctcagttt caccacacca aaaaaggaag acaagccggt tgcggtggct cacacctata | 5520 |
| atcccaaaac tttgggaggc cgaggcgggt ggatccacct gaggtcggga gttcgagact | 5580 |
| agcctgacca acatggagaa accctgtctc tactaaaaac acaaaattag cctggcgtgg | 5640 |
| tggcgcattc ctgtaatccc agctggggag ctgaggcagg agaatcgctt gaaccccgga | 5700 |
| ggcggaggtt gcagtgagcc aagatcgttc cattacactc cagtctgggc aagaaaagtg | 5760 |
| gaactccatc tccaaaaaaa aaaaaaaaaa aacaaggaag acaaaaagaa aagcagctaa | 5820 |
| agactttgcc tcaggggaga aagttctctt ttgggttgct atccacattc caacctcctg | 5880 |
| ttcccacctc ttcgtctgca tgcctaagaa actgttttac aagtaaataa gggacgcttt | 5940 |
| gtctaggctt tggagccagg aagttgagac aaatttagga atgagatgaa gtaatggtat | 6000 |
| tattgcaagt ctcaggtgta actacctctg ctctttctct gaagagtttc taatttctct | 6060 |
| tgtttactta ttttttttctt gtcattttttg ggattttatt actagttgtc tctaatcctt | 6120 |
| tctttaaatt cttcattatg aaacataaaa acaaatgcca ggcgcggcag ctcacgcctg | 6180 |
| taatcccagc actttgggag gccgaagcgg gcagatcacc cgggtcagga gttcgagacc | 6240 |
| agcctgatca acatggagaa accccgtctc tactaaaaaa tacaaaatta gctaggcgtg | 6300 |
| gtggcacatg ccagtaatcc cagctacttg agagactgag gcaggagaat cgcttgaacc | 6360 |
| gggaggcaga ggttgcggtg agccaagatc gcgccattgc actccagcct gggcaacaag | 6420 |
| agcaaaactc tgtctcaaaa aaaaaaaacc acatacaaac cagagataat attataatga | 6480 |
| gcctccaagt gcctaccacc ttgctgcagc acttgtcaat ccaggaccaa cccacctcac | 6540 |
| cggctcccca ctcattacca ccctccccta ctcaattact gaggtaaatc ctaggcagca | 6600 |
| tgatcatttc ttttttttct ttttatttat tttgagacag gatctgtctc tgtcacccag | 6660 |
| gctggagtgt agtggcatat ctctgctcac tgcagcctct gcctcccggg cagaagccat | 6720 |
| cctcccacct cagcctacat agtagctggg accacaggca cacaccacca cacactgcta | 6780 |
| atgttttgta ttttttgtag agactgggtt ttaccatgtt gatcaggctg gtctcaaact | 6840 |
| cctaggctca agcaatcctc ccacctcggc ctcccaaagt gctagaatta caggcgcgag | 6900 |
| ccactgcacc cagcgaagaa cacttttttaa aaaataaata ggccgggcgc ggtggctcac | 6960 |
| acctgtaatc ccagtacttt gggagcccaa ggagggcgaa tcatgaggtc aagagattga | 7020 |
| gaccatccta agtaacatgg tgaaacccca tttctactac aaatacaaaa acaaaattag | 7080 |
| cctggcgtgg tggcaggcgc ctgtagtccc agctacttgg gagctgaggc aggagaatgg | 7140 |
| agtgaacccg ggaggcggag cttgcagtga gctgagatca tgccactgca ctcccccctg | 7200 |
| ggcaacaga gtgagactcc caaaaaaaaa aaaaaagcc ccccctcccc acacacaata | 7260 |
| atataaataa ataaataacc acaatactat tatcacatct tacaaactca acaaaaattt | 7320 |
| cttaatatca tcaaataccc agtttgtgtt caaattttcc tgattgtttc ataaatatac | 7380 |
| tcttacagtt ggtttctttt agcgagattc aaatgagacc cacctgttga cctttgcccct | 7440 |
| tagggttttcc cagggtctga attttgttga cgacattccc atgttgctat gtaatacggt | 7500 |
| cctccatgcc ctgtgttttt ctgtaaactg atagatgtgg aggtgcaatg acatttgtgt | 7560 |
| ttgatttact ttggcaaata tagttcatca gtgatactct atacttcttg ttgctttaca | 7620 |
| tccggaggct gataatgtct gcttttctct cttttctaat tatttgtgaa aggaaaaatg | 7680 |
| tgggggggttg ggagaaaaaa acccttaagt acatactcgc taaatcacat tgctacaggt | 7740 |
| aacttccatt aagaacttga aagtaaaggt agctgcattt tccccctaggg aacacaatga | 7800 |
| tagacaggag ccttagtcta cagcttgaag gattgtaatt atacctaagc aaccctcctg | 7860 |

```
gaccagttta atgttattag ctgtgatgta tccctacctt tgatgtcatt atccttactt    7920
agctccctta aagcagagat caagatgaaa agggcttcag ctgcagcatg cacatggag     7980
attagagtgg ggcttttgga tgctgaggag cagacctaga atgggaaata gatgggagcc    8040
acagaagtga aggtccccct ccctcattgc tcaacctact ccacatctcc aggtctgcac    8100
atctgttcag ttactgaatc ctgtgtaagc taccttcttt ttcttttttc ttttatttat    8160
ttatttattt ttttttttgag atggagtttt gctcttgtta cccaggctgg agtgcaatgg   8220
tgcaatctcg gctcactgca ccctccaact cccaggttca tgcaattctc ctccctcagc    8280
cttccaagta gctgggatta caggctgcac caccatgtct ggctaatttt tgaaaaatca    8340
gtagagagag ggtttcacca tgttggccaa gccggtctcg aactcctgac ctcaagtgat    8400
ccacccacct tggcctccca aaatgctggg attacaggtg tgagccacca tgcccgctgt    8460
aaactacctt cttaaaagct ctagaagagg gcttttaacc ttttgttgtg tgtcatgcac    8520
cttccgcaag ctgatgaagt tgatagaccc atctcagaat tttttttttt ttttgagac    8580
agtgtctcac tctgtcaccc aggattggtt gcagtggcac gatcatgggt cattgcagcc   8640
tccacctccc aggctcaagt gatcctcctg actcagcctc ttgaatagct gagaccacag   8700
gcttgtgtca ccatgcccag gtaattttta atttttttttc gtagaggcag ggtctcacat  8760
tatgttgccc agtctggcct cgagaactcc tgggctcaag caatcttcct gccttgggct   8820
cccaaagtgg tgggattaca ggggagagcc accacaccta gccaggagga tgttttaaat   8880
acaccaaata aaacatttat acccaaatac agttatccaa atattaaatt aacaagagtt   8940
agggtgaccc tattaattag tgtaatttcc aaatagtaat gaacataagt gatagtttga   9000
gatttctgtg acttttctaa tgtgacgtga aaatatttgt gattttttctt tttctttttt  9060
tttttttgaga tggagttttcg ctcttgttgc ccaggctgga gtgcaatggc aagatctcgg  9120
ctcacctcaa cctccgcctc ctgggttcaa gcgattctcc tgcctcagcc tcttgagtag   9180
ctgggattac aggactgtgc caccacgtcc agctaatttt gtattttttag tagaaacagg  9240
gtttctccat gttggtcagg ctggtcttga actcccaacc tcaggcgatc cgcccgcctc   9300
ggcctcccaa agtgctggga ttacaggtgt gagccaccgc acctggccaa tatttgtgat   9360
ttttattgac gacaaagtca aaggttctct tcatattatt gtggtgtatc gcctacaagc   9420
ataattaaaa taaacactaa atttcagttt aaagtttact gaaaataaat atgtattttt   9480
tattccctat ttaagctttg aatcccctga cttcctatac cattaccact gtcctagttc   9540
aggttcatgt tgttttttac tttaattgtt atcacagtct cttaacattt ctccctatgt   9600
tctccagtcc tgtaggtgct aaatctgacg tggtcacttc tcagcttgga atccttcagt   9660
gcaccaccac agccttgaac tacatatttg aaatacatat ttattttcag taaactttaa   9720
actgaaattt agtgtttatt ttaattatgc ttgtaggcga tacaccacaa taatatgaag   9780
agaacctttg actttgtcgt caataaaaag tcccttgagg ggacttcaga tgtaagtccc   9840
ttagctgctc gttaaaactc ccccaggctg acccaataca caatcttgac tttaaaccac   9900
ttgtcattct aaatcactag catttcctgg aaaaaaaagc catttttcct tcagggctaa   9960
gctcagggac caattctgtg tcaccttctt tgaatcctga tgatattcac ttctttattt   10020
gacctgattt attgggcccc agacaccatg ctgagtgttg gggattcagc tctggacaat   10080
gtcaaatgtc agtcctgcct ttcagatcct ttctactggg tgagccctgg agtgctggtt   10140
ctcctcgcgg tgctgcctgt gctcctcctg cagatcactc ttggcctcgt cttcctctgc   10200
```

```
ctgcagtaca gactgagagg tacagggcag agggtgggtg gatcaggatc ctttctttaa    10260
atgagctggc ttcttggagc tacaccactt aacatgtatt tgtgagtgac ttctgggttc    10320
agaagttctt ctcactattg agtgataaag aaaaaaaata actccatgat gaaagagttt    10380
tacatcttac ggaatgcttt catatgaata atcggaccta gcatttccct atgagctaac    10440
tatgccatat agtaacccca ttttacagag gatacaactg aggccaggag tagttcagtg    10500
acttactcaa accgatataa cttataagtg gtagagctga ggcctctgta tcatacctag    10560
cagctccatg caacttggga gagtgtgagc ttcgaagtca gacaggtcta ggctattagg    10620
agttttgaat aaagatactg aagtgaaagt ctctaccaca cagtaggcgt tcgaaaattg    10680
tttcctcttt ctccattcaa cactgaggac tcaggttcag ctgctgatga agctcctctt    10740
ttttgcctag agctttcatt ctgagccttc tcctcctacc aagtgtctcc ccaatgccag    10800
agcaggaaga gtcttcactc ctcccaatgc cccacctccc atttgttact aagaggagag    10860
gagaaagtag caaggagggt atggggaatg ttctggggga atgggtgttg gtgcgatcaa    10920
caacaaagtc ctttctctca ccttgaattc atcccagatg cctgcttgtt tacttcttcc    10980
acacaaaaaa aggccttcag ccctcatggc tgagcagaaa gaatctgaat gttagagtca    11040
ggcagcctgg gtttgaattc catctcaggt actgaactct atagcaaaat tcttagattc    11100
tccaagcttc agttgccttg tctgtcaaat agagaaaaca tccttcgtcc taaattgtag    11160
ggaggattaa agtcatgcaa agtgcctact acaaatccag tcacaaagta gctagctact    11220
cactaaatgt tcagctcctc cctcctcatt cagatgggaa gtggctttag ataaacaaag    11280
tggcaacgca gtgggctgga gcagctctgt gaactgagaa tccaagaaaa ggggcgaaga    11340
gcagctggga tgtattggat gcttgtgctg gcttggagca ttgctcacat tctttattcg    11400
ctattgtatc tagactatag ctagagaaag agccgcaacc attggcttta aatccagtgc    11460
tcttcctact ctcctgaggt tgtttccagg ctgcagagaa atagcctgca caaggggccc    11520
aggcgctggg tgtgggaggg tccccaccga gagccagaac atgcaggaac taaaatgttg    11580
ccttttctta ttttaggaaa acttcgagca gagataggtg agttccagtc atcgtttctc    11640
ccaattcttg ccttttggtt ttttggcata acggaaatgg tcccattctt ggaccgtctc    11700
tccctctcaa taccctgttt tcccctcagt ttcccttttct ctacagtggg tgtgtcgtgc    11760
ctagaacaag ttttaagtaa ttaaataaca aagactcagg ataaaaggat ccttttggga    11820
gtgccctact aaatccatt ccatttgttt ctctttcaga gaatctccac cggacttttg    11880
gtaagttccg gcatgtctag gccctcccag gtcaacttgg tatttcactc tagttccagt    11940
cacctggggg aacaaggacc cctggctcct ggttgagtcc cttcctctct tctcttttct    12000
ttctttaaat aagaagtcat ttgcatttag gattggtaaa atcataataa aaatactcat    12060
gtactgtttt tatgtgccag gcactattct aactacttta caaaaacgtt atcttattct    12120
gtttaactcc ttatgcacat gatctctctt ttcaggaatg ccaaaacaga ggtaaataga    12180
tcgtttacac gtaaacctga tgtctggttg gggaggtgaa acaaacagaa acaagacaca    12240
actgtatcac ctgtacttat atttctgctt tacaaactca ggatgttttcc atgagtacag    12300 aacatgacta atcagagaag acctcataga ggaatagaaa agccaccaag ccccactagg    12360
aattgacccc tcaaggacat ggtttctagc cttttgttc actgcagatt gcccaatgcc    12420
taaagataat ggcaacagaa gagcacccaa atatttgtta gataaatgtt gcagacacta    12480
gaaggtgtca ttagggcaca gatggtacct tctctgagca aacttccttc acagctcctc    12540
ctcccgaggc tgtaggtgac tctactcttg tcacctggca cacagagttc tatcgtacga    12600
```

```
tttaggaaat tagaccagtg tgtggaccac acacacacac atctttacac acccaaagag    12660
gaggaatagt atctttgttt tggaggactt gactatgaaa ggtcttaact ccttttttgta   12720 ccatgaatct ctctggcact ccagtgaagt ctaaaggacc cctttgcaga atgtttttaa    12780
atatacacat aaaatagaac acataggatt gcaaaaacaa tcattgtact aaaatacagt    12840
tatcaaccga taatcacatt tgtgatatag taacataaat gtttcttttt ttttttttg     12900 gaggcagagt ttggctcttg tcacccaggc tggagtgcaa tggcgcgatc taggctcact    12960
gaaacctctg cctcccgggt tcaagcgatt ctcagcctcc tgagtagctg ggattacagg    13020
tgcccgccac cacacccagc taattttttgt attttttagta gagactaggt ttcaccaggt  13080
tggccaggct ggcctcgaac tcctgacctc aggtgatcca cctgccttgg cctcccaaag    13140
tgctgggatt acgggcatga gccaccgtgc ccggccataa atatttcttt agccaaagta    13200
atacattaag taatgtagca gcaagtctaa taacctgtaa tttctttctt tctttctttc    13260
ttttcttttt tttgagatga agttttttgtg agatggagtg caatggcaca atctcggctc   13320
actgcaacct ccacctcctg ggttcaagcg attctcctgc ctcagcctcc caagttgctg    13380
gaactacagg cgcatgccac catgcccagc taattttttgt attttttagta gagacggggt  13440 ttcaccatgt tggccaggct ggtcttgaac ccctgacctc aggtgatctg cctgccttgg    13500
ccttccaaag tgctgggatt acaggcatga gccaccaggc ccagcccaat aacctttaat    13560
ttcaacatac taataaacat aaacagtatt tcaagatttc tgcaataact ctaatgggaa    13620
tgaaaacatc tgtggcttcc attggtaatt aagtcacagg tactgctcat attgtggtta    13680
gttgtaaaat gttttggttt gttttgtttt ttccaagact tgggggaatg ggtgttggtg    13740
ggatcaacaa gagtcttgct ctgtggccca ggctggagtg caggggcagg atcttggctc    13800
actgcaacct ccgcctccca ggttcaagcg attctcctgc ctcagcctcc tgagtagctg    13860
gcattacagg catgtgccac cacgcccagc taattttttac attttttagta gagatggggt  13920 ttcaccatgt tggcctggct ggtcttgaac tcttggcctc atgatccacc cgtctcggac    13980
tcccagagtg ttgggattac aggcatgagc caccacacct ggcagttgtt acattttttaa  14040 tgaaagaaaa tgttaaatcc agttattgaa ataaggagg cagtactttt ctcatccaag     14100
ttcatggact ttctgaattt tgtccccaga gtcctttggt gttctaggac cccaggttaa    14160
ggaacccaaa aagacaggtg ggtgggcat gagggggaac acatgttaat ccctgtttgt    14220
tctggtgaac aattcagatc cccactttct gagggtgccc tgctggaaga taaccctgtt    14280
tgtaattgtg ccggttcttg gaccccttggt tgccttgatc atctgctaca actggctaca   14340
tcgaagacta gcaggtgcag tggctgggca gcaggcaaga ccaccaaaata gtgggggacc   14400 aagtcagctc tgaatgggaa gccaaaagag aatagaacca ggactcaaga ttaggggagc    14460
tgggatttcc ttattcctct gtccccatgc ccaacccccag gctcttctga aaactgtga    14520 agagaaccac ttactggatc tgtgggatcc cccagtggaa agggcagtgt gggtcactcc    14580
aaatgtccat agggaggatg tggggaaggt gctattcatc ttccactaat cacatatttg    14640 tttcttttg ttttcagggc aattccttga agagctacgt aagttctctt ctctctgtta     14700
taagcagaga ataaaaagcc aggaaaggga gacagaagca acaagaggaa gaggcgggct    14760
attgagggat cacattccca gaggaaagga ggagctggag agcctgggtg gagggaagac    14820
tcctcctggg aggtagaggg caaagaagcc agctgttaga gacacattta caggtggcag    14880
agaagctgga ggcactccta tctgccacct gatccattcc tccttcactg cccctaagca    14940
```

```
ggaatccaac cctagctggt ctcattgccc attccacagc aactgcccag tgcctcacct    15000
ctcagatcaa ccattgaggc aggaatggag acaagatgac cccaagggct tttcttctcc    15060
ctagttcaat ggttttatga tacaaactac tgacatacgt ttttcaagtt attttctcct    15120
tcttctagga aatcccttct gagtgatgtc acatcttggc aggggtggag agagcctgg     15180 ttgcccaggg atttgtcctt ggggacatct catccatcaa gttgcacact cactggcatc    15240
tttgctatgg ggacattcca atttgcactt tcaggaacac tctgaattcc aagtagaatt    15300
gatttccctt cttctgtcat ctacctttttc tcttcatttt cccatttttta ttacccttct   15360 ttccatttct ctctccagtc ttccacctgg aagccctctc tggctaagga caggcaggtg    15420
cccctctctc catcagagga cacctgtact ggagagcaac acaggatggt ctctgccatg    15480
aactggaggc aggaatctc ctcactgaaa attacagtat ggtaactttg caatggtgg       15540 ttgtttcttc caagactcca gccctgattg cgcaaaactg aaaggcatgt gaagggaagg    15600
aagaggaaga gtgcaaaaca ttgaagagag agctgagtga gctgaagagt gaggatatga    15660
gtagccccaa cccaaacctg gagatgggga gaaacctaca gaatactagc cagagctcct    15720
ccttgtcttg gcagcctact agggacctgg ggaagcaaaa acgaaagctg ggcaacatgc    15780
ctgctttaga atgttttcct tctacttaca catcttccac aggtctcaga atctttcctt    15840
cctctcatcc ttttctccta tctacatatc tatcagagta tccactgttt attcaacaac    15900
tactacttga tggtcagaca caaacaaaca agctaggtgc taattaataa agatacgagt    15960
tttggccggg tgcggtggct cacgcctgta atcccagcac tttgggaggc cgaggcgggc    16020
gaatcacgag gtcaggagtt caagaccagc ctggccaaca tggtgaaacc ccatctctac    16080
taaaaataca acaattaac tgagcatagt ggtgggcacc tataatacca gctactccgg      16140
aggctgaggc aggagaatcg cttgaaccca ggaggcagag gttgcagtga gctgagatcg    16200
cgccactgca ctctagccgg agtgacagag taagactctg tctcaaaaat aaataaataa    16260
ataaataaat aaataaataa ataaataaaa aataataata caagttttca taagcacact    16320
tctaacccct tgtctttat gtatttcctt ccttatccac gcacctgtct ccctctactc     16380
cagcctcatt accccagagg tcagtcctca ggaaaactaa acacaaagaa agagctcagt    16440
cagaaaggcc atttatttat gtttcaagat gctcactgcc tcctttgttt tgtctccttt    16500
gcaggccttc tctcttaggc ctcttctcct gggggtatgg atcctggggg gagattgatc    16560
acctccatgc ttccattcct ccccagccat agtgggaca tcatgagaga agccaagcca      16620
ctggcccagg atcacccggc atttatggtg gctgctctgg cacaggtcct tgcctttata    16680
gcccctccag tgatccataa ggccctcttt ctccccaaag gagaggtcac agatagggca    16740
aaggtagctc ttctgcttcc agtgggtctg ctggtgtctg accagcctgg aaaatgagct    16800
gaaagacttg ctgcaatgga agcagtagtt gggcggctct gtgaggtggc ccttctggtg    16860
tctggagaga taggatttct tgctaaaagt caaagaacaa tgggggcaac agaagacatt    16920
gagtcttgag ggcttcactg gatgagagtt ggatctggca tcctgacaga gggttccagt    16980
gatgggtgcc tggtcctgg tcacaggtgc ttggttctta agtacagatg cctggttctg     17040
ggccatagga ccctcagttc taaatatggg ttcctgggac ctggccactg gtgcatggtt    17100
cacatccaaa agcccctgga tggacctctg gcttctggcg atgggtgtct ggaattcagc    17160
ctgggtgcct ggaatcctca agtacactc ctggtttcca tccactggct cctggttttg     17220
gtgtatcttc tggtggcgtt tgagctcaga ctggtcccgg aagctcttcc cacacacaga    17280
gcatgaatgg ggccggtaac ccagatggac gcggcggtga cgacttagtc cagaagcatc    17340
```

```
acagtaggtc ttgtcacaga gcgtgcaaca gaagggcctc tccccaagat gcatgcgtct   17400
gtgatagctg agggacttgg ggctccgaaa caacttccca cactgactgc agctgttagt   17460
cagcttggga ttgtgaacaa actggtggct atagaggtag gagcgcctgc tgaaacattt   17520
ggcacaggtg tagcaaaa                                                  17538

<210> SEQ ID NO 10
<211> LENGTH: 327
<212> TYPE: DNA
<213> ORGANISM: Rattus norvegicus

<400> SEQUENCE: 10
tttgtatgtc attgcaggat tcatgctttc cagtgtgtca tctatggaac tgcctctttc     60
ttcttccttt atggggccct cctgctggct gagggcttct acaccaccgg cgctgtcagg    120
cagatctttg gcgactacaa gaccaccatc tgcggcaagg gcctgagcgc aacggtaaca    180
gggggccaga aggggagggg ttacagaggc caacatcaag ctcattcttt ggagcgggtg    240
tgtcattgtt tgggaaaatg gctaggacat cccgacaagg tgatcatcct caggattttg    300
tggcaataac aaggggtggg gggacaa                                         327

<210> SEQ ID NO 11
<211> LENGTH: 2013
<212> TYPE: DNA
<213> ORGANISM: Rattus norvegicus

<400> SEQUENCE: 11
ctgtatcagt gctcctcgtc gcctcactgt acttcacgga agagacttgg ttgactggcc     60
acttggagcg gaatcaggag acattcccaa ctcagagaga ctgagcccta gctcgcccac    120
ttgctggaca agatgatatt ccttaccacc ctgcctctgt tttggataat gatttcagct    180
tctcgagggg ggcactgggg tgcctggatg ccctcgtcca tctcagcctt cgagggcacg    240
tgtgtctcca tccctgccg tttcgacttc ccggatgagc tcagaccggc tgtggtacat    300
ggcgtctggt atttcaacag tccctacccc aagaactacc cgccagtggt cttcaagtcc    360
cgcacacaag tggtccacga gagcttccag ggccgtagcc gcctgttggg agacctgggc    420
ctacgaaact gcaccctgct tctcagcacg ctgagccctg agctgggagg gaaatactat    480
ttccgaggtg acctgggcgg ctacaaccag tacaccttct cggagcacag cgtcctggac    540
atcatcaaca cccccaacat cgtggtgccc ccagaagtgg tggcaggaac ggaagtagag    600
gtcagctgca tggtgccgga caactgccca gagctgcgcc ctgagctgag ctggctgggc    660
cacgaggggc tagggagcc cactgttctg ggtcggctgc gggaggatga aggcacctgg    720
gtgcaggtgt cactgctaca cttcgtgcct actagagagg ccaacggcca ccgtctgggc    780
tgtcaggctg ccttccccaa caccaccttg cagttcgagg gttacgccag tctggacgtc    840
aagtaccccc cggtgattgt ggagatgaat tcctctgtgg aggccattga gggctcccac    900
gtcagcctgc tctgtggggc tgacagcaac ccgccaccgc tgctgacttg gatgcgggat    960
gggatggtgt tgagggaggc agttgctgag agcctgtacc tggatctgga ggaggtgacc   1020
ccagcagagg acggcatcta tgcttgcctg cagagaatg cctatggcca ggacaaccgc   1080
acggtggagc tgagcgtcat gtatgcacct tggaagccca cagtgaatgg acggtggtg   1140 gcggtagagg gggagacagt ctccatcctg tgttccacac agagcaaccc ggaccctatt   1200
ctcaccatct tcaaggagaa gcagatcctg gccacggtca tctatgagag tcagctgcag   1260
```

-continued

```
ctggaactcc ctgcagtgac gcccgaggac gatggggagt actggtgtgt agctgagaac    1320
cagtatggcc agagagccac cgccttcaac ctgtctgtgg agtttgctcc cataatcctt    1380
ctggaatcgc actgtgcagc ggccagagac accgtgcagt gcctgtgtgt ggtaaaatcc    1440
aacccggaac cctccgtggc ctttgagctg ccttcccgca acgtgactgt gaacgagaca    1500
gagagggagt tgtgtactc agagcgcagc ggcctcctgc tcaccagcat cctcacgctc    1560
cggggtcagg cccaagcccc accccgcgtc atttgtacct ccaggaacct ctacggcacc    1620
cagagcctcg agctgccttt ccagggagca caccgactga tgtgggccaa atcggccct    1680 gtgggtgctg tggtcgcctt tgccatcctg attgccattg tctgctacat cacccagaca    1740
agaagaaaaa agaacgtcac agagagcccc agcttctcag cgggagacaa ccctcatgtc    1800
ctgtacagcc ccgaattccg aatctctgga gcacctgata agtatgagag tgagaagcgc    1860
ctggggtccg agaggaggct gctgggcctt aggggggaac ccccagaact ggacctcagt    1920
tattcccact cagacctggg gaaacgaccc accaaggaca gctacaccct gacagaggag    1980
ctggctgagt acgcagaaat ccgagtcaag tga                                 2013
```

<210> SEQ ID NO 12
<211> LENGTH: 171
<212> TYPE: PRT
<213> ORGANISM: Homo sapiens

<400> SEQUENCE: 12

```
Met Ala Ser Gln Lys Arg Pro Ser Gln Arg His Gly Ser Lys Tyr Leu
1               5                   10                  15

Ala Thr Ala Ser Thr Met Asp His Ala Arg His Gly Phe Leu Pro Arg
            20                  25                  30

His Arg Asp Thr Gly Ile Leu Asp Ser Ile Gly Arg Phe Phe Gly Gly
        35                  40                  45

Asp Arg Gly Ala Pro Lys Arg Gly Ser Gly Lys Asp Ser His His Pro
    50                  55                  60

Ala Arg Thr Ala His Tyr Gly Ser Leu Pro Gln Lys Ser His Gly Arg
65                  70                  75                  80

Thr Gln Asp Glu Asn Pro Val Val His Phe Phe Lys Asn Ile Val Thr
                85                  90                  95

Pro Arg Thr Pro Pro Ser Gln Gly Lys Gly Arg Gly Leu Ser Leu
            100                 105                 110

Ser Arg Phe Ser Trp Gly Ala Glu Gly Gln Arg Pro Gly Phe Gly Tyr
        115                 120                 125

Gly Gly Arg Ala Ser Asp Tyr Lys Ser Ala His Lys Gly Phe Lys Gly
    130                 135                 140

Val Asp Ala Gln Gly Thr Leu Ser Lys Ile Phe Lys Leu Gly Gly Arg
145                 150                 155                 160

Asp Ser Arg Ser Gly Ser Pro Met Ala Arg Arg
                165                 170
```

<210> SEQ ID NO 13
<211> LENGTH: 274
<212> TYPE: PRT
<213> ORGANISM: Homo sapiens

<400> SEQUENCE: 13

```
Met Gly Leu Leu Glu Cys Cys Ala Arg Cys Leu Val Gly Ala Pro Phe
1               5                   10                  15

Ala Ser Leu Val Ala Thr Gly Leu Cys Phe Phe Gly Val Ala Leu Phe
```

```
                         20                  25                  30
Cys Gly Cys Gly His Glu Ala Leu Thr Gly Thr Glu Lys Leu Ile Glu
            35                  40                  45

Thr Tyr Phe Ser Lys Asn Tyr Gln Asp Tyr Glu Tyr Leu Ile Asn Val
 50                  55                  60

Ile His Ala Phe Gln Tyr Val Ile Tyr Gly Thr Ala Ser Phe Phe Phe
 65                  70                  75                  80

Leu Tyr Gly Ala Leu Leu Ala Glu Gly Phe Tyr Thr Thr Gly Ala
                85                  90                  95

Val Arg Gln Ile Phe Gly Asp Tyr Lys Thr Thr Ile Cys Gly Lys Gly
                100                 105                 110

Leu Ser Ala Thr Val Thr Gly Gly Gln Lys Gly Arg Gly Ser Arg Gly
                115                 120                 125

Gln His Gln Ala His Ser Leu Glu Arg Val Cys His Cys Leu Gly Lys
                130                 135                 140

Trp Leu Gly His Pro Asp Lys Ile Thr Tyr Ala Leu Thr Val Val Trp
145                 150                 155                 160

Leu Leu Val Phe Ala Cys Ser Ala Val Pro Val Tyr Ile Tyr Phe Asn
                165                 170                 175

Thr Trp Thr Thr Cys Gln Ser Ile Ala Phe Pro Ser Lys Thr Ser Ala
                180                 185                 190

Ser Ile Gly Ser Leu Cys Ala Asp Ala Arg Met Tyr Gly Val Leu Pro
                195                 200                 205

Trp Asn Ala Phe Pro Gly Lys Val Cys Gly Ser Asn Leu Leu Ser Ile
                210                 215                 220

Cys Lys Thr Ala Glu Phe Gln Met Thr Phe His Leu Phe Ile Ala Ala
225                 230                 235                 240

Phe Val Gly Ala Ala Ala Thr Leu Val Ser Leu Leu Thr Phe Met Ile
                245                 250                 255

Ala Ala Thr Tyr Asn Phe Ala Val Leu Lys Leu Met Gly Arg Gly Thr
                260                 265                 270

Lys Phe

<210> SEQ ID NO 14
<211> LENGTH: 247
<212> TYPE: PRT
<213> ORGANISM: Homo sapiens

<400> SEQUENCE: 14

Met Ala Ser Leu Ser Arg Pro Ser Leu Pro Ser Cys Leu Cys Ser Phe
 1               5                  10                  15

Leu Leu Leu Leu Leu Gln Val Ser Ser Ser Tyr Ala Gly Gln Phe
                20                  25                  30

Arg Val Ile Gly Pro Arg His Pro Ile Arg Ala Leu Val Gly Asp Glu
                35                  40                  45

Val Glu Leu Pro Cys Arg Ile Ser Pro Gly Lys Asn Ala Thr Gly Met
 50                  55                  60

Glu Val Gly Trp Tyr Arg Pro Pro Phe Ser Arg Val Val His Leu Tyr
 65                  70                  75                  80

Arg Asn Gly Lys Asp Gln Asp Gly Asp Gln Ala Pro Glu Tyr Arg Gly
                85                  90                  95

Arg Thr Glu Leu Leu Lys Asp Ala Ile Gly Glu Gly Lys Val Thr Leu
                100                 105                 110

Arg Ile Arg Asn Val Arg Phe Ser Asp Glu Gly Gly Phe Thr Cys Phe
```

```
                115                 120                 125
Phe Arg Asp His Ser Tyr Gln Glu Glu Ala Ala Met Glu Leu Lys Val
        130                 135                 140

Glu Asp Pro Phe Tyr Trp Val Ser Pro Gly Val Leu Val Leu Leu Ala
145                 150                 155                 160

Val Leu Pro Val Leu Leu Leu Gln Ile Thr Leu Gly Leu Val Phe Leu
                165                 170                 175

Cys Leu Gln Tyr Arg Leu Arg Gly Lys Leu Arg Ala Glu Ile Glu Asn
                180                 185                 190

Leu His Arg Thr Phe Asp Pro His Phe Leu Arg Val Pro Cys Trp Lys
            195                 200                 205

Ile Thr Leu Phe Val Ile Val Pro Val Leu Gly Pro Leu Val Ala Leu
        210                 215                 220

Ile Ile Cys Tyr Asn Trp Leu His Arg Arg Leu Ala Gly Gln Phe Leu
225                 230                 235                 240

Glu Glu Leu Arg Asn Pro Phe
                245

<210> SEQ ID NO 15
<211> LENGTH: 18
<212> TYPE: PRT
<213> ORGANISM: Rattus norvegicus

<400> SEQUENCE: 15

Ala Pro Lys Arg Gly Ser Gly Lys Asp Ser His Thr Arg Thr His
1               5                   10                  15

Tyr Gly

<210> SEQ ID NO 16
<211> LENGTH: 23
<212> TYPE: PRT
<213> ORGANISM: Homo sapiens

<400> SEQUENCE: 16

Val Leu Gly Gly Gly Cys Ala Leu Leu Arg Cys Pro Ala Leu Asp Ser
1               5                   10                  15

Leu Thr Pro Ala Asn Glu Asp
            20

<210> SEQ ID NO 17
<211> LENGTH: 4684
<212> TYPE: DNA
<213> ORGANISM: Rattus norvegicus
<220> FEATURE:
<221> NAME/KEY: CDS
<222> LOCATION: (253)..(3744)
<223> OTHER INFORMATION:

<400> SEQUENCE: 17
attgctcgtc tgggcggcgg cggcggctgc agcctgggac agggcgggtg gcacatctcg      60
atcgcgaagg caggagaagc agtctcattg ttccggagc cgtcgcctct gcaggttctt     120
cggctcggct cggcacgact cggcctgcct ggccctgcc agtcttgccc aaccccaca     180 accgccgcg actctgagga gaagcggccc tgcggcggct gtagctgcag catcgtcggc     240
gacccgccag cc atg gaa gac ata gac cag tcg tcg ctg gtc tcc tcg tcc    291
             Met Glu Asp Ile Asp Gln Ser Ser Leu Val Ser Ser Ser
               1               5                  10 acg gac agc ccg ccc cgg cct ccg ccc gcc ttc aag tac cag ttc gtg    339
Thr Asp Ser Pro Pro Arg Pro Pro Pro Ala Phe Lys Tyr Gln Phe Val
```

|     |     |     |     |     |     |     |     |     |     |     |     |     |     |     |      |
|-----|-----|-----|-----|-----|-----|-----|-----|-----|-----|-----|-----|-----|-----|-----|------|
|     |     | 15  |     |     |     | 20  |     |     |     | 25  |     |     |     |     |      |
| acg | gag | ccc | gag | gac | gag | gag | gac | gag | gag | gag | gag | gag | gac | gag | 387  |
| Thr | Glu | Pro | Glu | Asp | Glu | Glu | Asp | Glu | Glu | Glu | Glu | Glu | Asp | Glu |      |
| 30  |     |     |     |     | 35  |     |     |     |     | 40  |     |     |     | 45  |      |
| gag | gac | gac | gag | gac | cta | gag | gaa | ctg | gag | gtg | ctg | gag | agg | aag | ccc | 435 |
| Glu | Asp | Asp | Glu | Asp | Leu | Glu | Glu | Leu | Glu | Val | Leu | Glu | Arg | Lys | Pro |     |
|     |     |     |     | 50  |     |     |     |     | 55  |     |     |     |     | 60  |     |
| gca | gcc | ggg | ctg | tcc | gca | gct | gcg | gtg | ccg | ccc | gcc | gcc | gcg | ccg | 483  |
| Ala | Ala | Gly | Leu | Ser | Ala | Ala | Ala | Val | Pro | Pro | Ala | Ala | Ala | Pro |      |
|     |     |     | 65  |     |     |     |     | 70  |     |     |     |     | 75  |     |      |
| ctg | ctg | gac | ttc | agc | agc | gac | tcg | gtg | ccc | ccc | gcg | ccc | cgc | ggg | ccg | 531 |
| Leu | Leu | Asp | Phe | Ser | Ser | Asp | Ser | Val | Pro | Pro | Ala | Pro | Arg | Gly | Pro |     |
|     |     | 80  |     |     |     |     | 85  |     |     |     |     | 90  |     |     |     |
| ctg | ccg | gcc | gcg | ccc | cct | gcc | gct | cct | gag | agg | cag | cca | tcc | tgg | gaa | 579 |
| Leu | Pro | Ala | Ala | Pro | Pro | Ala | Ala | Pro | Glu | Arg | Gln | Pro | Ser | Trp | Glu |     |
|     | 95  |     |     |     |     | 100 |     |     |     |     | 105 |     |     |     |     |
| cgc | agc | ccc | gcg | gcg | ccc | gcg | cca | tcc | ctg | ccg | ccc | gct | gcc | gca | gtc | 627 |
| Arg | Ser | Pro | Ala | Ala | Pro | Ala | Pro | Ser | Leu | Pro | Pro | Ala | Ala | Ala | Val |     |
| 110 |     |     |     |     | 115 |     |     |     |     | 120 |     |     |     |     | 125 |
| ctg | ccc | tcc | aag | ctc | cca | gag | gac | gac | gag | cct | ccg | gcg | agg | ccc | ccg | 675 |
| Leu | Pro | Ser | Lys | Leu | Pro | Glu | Asp | Asp | Glu | Pro | Pro | Ala | Arg | Pro | Pro |     |
|     |     |     | 130 |     |     |     |     | 135 |     |     |     |     | 140 |     |     |
| cct | ccg | ccg | cca | gcc | ggc | gcg | agc | ccc | ctg | gcg | gag | ccc | gcc | gcg | ccc | 723 |
| Pro | Pro | Pro | Pro | Ala | Gly | Ala | Ser | Pro | Leu | Ala | Glu | Pro | Ala | Ala | Pro |     |
|     |     | 145 |     |     |     |     | 150 |     |     |     |     | 155 |     |     |     |
| cct | tcc | acg | ccg | gcc | gcg | ccc | aag | cgc | agg | ggc | tcc | ggc | tca | gtg | gat | 771 |
| Pro | Ser | Thr | Pro | Ala | Ala | Pro | Lys | Arg | Arg | Gly | Ser | Gly | Ser | Val | Asp |     |
|     |     | 160 |     |     |     |     | 165 |     |     |     |     | 170 |     |     |     |
| gag | acc | ctt | ttt | gct | ctt | cct | gct | gca | tct | gag | cct | gtg | ata | ccc | tcc | 819 |
| Glu | Thr | Leu | Phe | Ala | Leu | Pro | Ala | Ala | Ser | Glu | Pro | Val | Ile | Pro | Ser |     |
|     | 175 |     |     |     |     | 180 |     |     |     |     | 185 |     |     |     |     |
| tct | gca | gaa | aaa | att | atg | gat | ttg | atg | gag | cag | cca | ggt | aac | act | gtt | 867 |
| Ser | Ala | Glu | Lys | Ile | Met | Asp | Leu | Met | Glu | Gln | Pro | Gly | Asn | Thr | Val |     |
| 190 |     |     |     |     | 195 |     |     |     |     | 200 |     |     |     |     | 205 |
| tcg | tct | ggt | caa | gag | gat | ttc | cca | tct | gtc | ctg | ctt | gaa | act | gct | gcc | 915 |
| Ser | Ser | Gly | Gln | Glu | Asp | Phe | Pro | Ser | Val | Leu | Leu | Glu | Thr | Ala | Ala |     |
|     |     |     | 210 |     |     |     |     | 215 |     |     |     |     | 220 |     |     |
| tct | ctt | cct | tct | cta | tct | cct | ctc | tca | act | gtt | tct | ttt | aaa | gaa | cat | 963 |
| Ser | Leu | Pro | Ser | Leu | Ser | Pro | Leu | Ser | Thr | Val | Ser | Phe | Lys | Glu | His |     |
|     |     | 225 |     |     |     |     | 230 |     |     |     |     | 235 |     |     |     |
| gga | tac | ctt | ggt | aac | tta | tca | gca | gtg | tca | tcc | tca | gaa | gga | aca | att | 1011 |
| Gly | Tyr | Leu | Gly | Asn | Leu | Ser | Ala | Val | Ser | Ser | Ser | Glu | Gly | Thr | Ile |      |
|     | 240 |     |     |     |     | 245 |     |     |     |     | 250 |     |     |     |     |
| gaa | gaa | act | tta | aat | gaa | gct | tct | aaa | gag | ttg | cca | gag | agg | gca | aca | 1059 |
| Glu | Glu | Thr | Leu | Asn | Glu | Ala | Ser | Lys | Glu | Leu | Pro | Glu | Arg | Ala | Thr |      |
| 255 |     |     |     |     | 260 |     |     |     |     | 265 |     |     |     |     |     |
| aat | cca | ttt | gta | aat | aga | gat | tta | gca | gaa | ttt | tca | gaa | tta | gaa | tat | 1107 |
| Asn | Pro | Phe | Val | Asn | Arg | Asp | Leu | Ala | Glu | Phe | Ser | Glu | Leu | Glu | Tyr |      |
| 270 |     |     |     |     | 275 |     |     |     |     | 280 |     |     |     |     | 285 |
| tca | gaa | atg | gga | tca | tct | ttt | aaa | ggc | tcc | cca | aaa | gga | gag | tca | gcc | 1155 |
| Ser | Glu | Met | Gly | Ser | Ser | Phe | Lys | Gly | Ser | Pro | Lys | Gly | Glu | Ser | Ala |      |
|     |     |     | 290 |     |     |     |     | 295 |     |     |     |     | 300 |     |     |
| ata | tta | gta | gaa | aac | act | aag | gaa | gaa | gta | att | gtg | agg | agt | aaa | gac | 1203 |
| Ile | Leu | Val | Glu | Asn | Thr | Lys | Glu | Glu | Val | Ile | Val | Arg | Ser | Lys | Asp |      |
|     |     | 305 |     |     |     |     | 310 |     |     |     |     | 315 |     |     |     |
| aaa | gag | gat | tta | gtt | tgt | agt | gca | gcc | ctt | cac | agt | cca | caa | gaa | tca | 1251 |
| Lys | Glu | Asp | Leu | Val | Cys | Ser | Ala | Ala | Leu | His | Ser | Pro | Gln | Glu | Ser |      |
|     | 320 |     |     |     |     | 325 |     |     |     |     | 330 |     |     |     |     |
| cct | gtg | ggt | aaa | gaa | gac | aga | gtt | gtg | tct | cca | gaa | aag | aca | atg | gac | 1299 |

```
Pro Val Gly Lys Glu Asp Arg Val Val Ser Pro Glu Lys Thr Met Asp
    335                 340                 345 att ttt aat gaa atg cag atg tca gta gta gca cct gtg agg gaa gag      1347
Ile Phe Asn Glu Met Gln Met Ser Val Val Ala Pro Val Arg Glu Glu
350                 355                 360                 365 tat gca gac ttt aag cca ttt gaa caa gca tgg gaa gtg aaa gat act      1395
Tyr Ala Asp Phe Lys Pro Phe Glu Gln Ala Trp Glu Val Lys Asp Thr
                370                 375                 380 tat gag gga agt agg gat gtg ctg gct gct aga gct aat gtg gaa agt      1443
Tyr Glu Gly Ser Arg Asp Val Leu Ala Ala Arg Ala Asn Val Glu Ser
            385                 390                 395 aaa gtg gac aga aaa tgc ttg gaa gat agc ctg gag caa aaa agt ctt      1491
Lys Val Asp Arg Lys Cys Leu Glu Asp Ser Leu Glu Gln Lys Ser Leu
        400                 405                 410 ggg aag gat agt gaa ggc aga aat gag gat gct tct ttc ccc agt acc      1539
Gly Lys Asp Ser Glu Gly Arg Asn Glu Asp Ala Ser Phe Pro Ser Thr
    415                 420                 425 cca gaa cct gtg aag gac agc tcc aga gca tat att acc tgt gct tcc      1587
Pro Glu Pro Val Lys Asp Ser Ser Arg Ala Tyr Ile Thr Cys Ala Ser
430                 435                 440                 445 ttt acc tca gca acc gaa agc acc aca gca aac act ttc cct ttg tta      1635
Phe Thr Ser Ala Thr Glu Ser Thr Thr Ala Asn Thr Phe Pro Leu Leu
                450                 455                 460 gaa gat cat act tca gaa aat aaa aca gat gaa aaa aaa ata gaa gaa      1683
Glu Asp His Thr Ser Glu Asn Lys Thr Asp Glu Lys Lys Ile Glu Glu
            465                 470                 475 agg aag gcc caa att ata aca gag aag act agc ccc aaa acg tca aat      1731
Arg Lys Ala Gln Ile Ile Thr Glu Lys Thr Ser Pro Lys Thr Ser Asn
        480                 485                 490 cct ttc ctt gta gca gta cag gat tct gag gca gat tat gtt aca aca      1779
Pro Phe Leu Val Ala Val Gln Asp Ser Glu Ala Asp Tyr Val Thr Thr
    495                 500                 505 gat acc tta tca aag gtg act gag gca gca gtg tca aac atg cct gaa      1827
Asp Thr Leu Ser Lys Val Thr Glu Ala Ala Val Ser Asn Met Pro Glu
510                 515                 520                 525 ggt ctg acg cca gat tta gtt cag gaa gca tgt gaa agt gaa ctg aat      1875
Gly Leu Thr Pro Asp Leu Val Gln Glu Ala Cys Glu Ser Glu Leu Asn
                530                 535                 540 gaa gcc aca ggt aca aag att gct tat gaa aca aaa gtg gac ttg gtc      1923
Glu Ala Thr Gly Thr Lys Ile Ala Tyr Glu Thr Lys Val Asp Leu Val
            545                 550                 555 caa aca tca gaa gct ata caa gaa tca ctt tac ccc aca gca cag ctt      1971
Gln Thr Ser Glu Ala Ile Gln Glu Ser Leu Tyr Pro Thr Ala Gln Leu
        560                 565                 570 tgc cca tca ttt gag gaa gct gaa gca act ccg tca cca gtt ttg cct      2019
Cys Pro Ser Phe Glu Glu Ala Glu Ala Thr Pro Ser Pro Val Leu Pro
    575                 580                 585 gat att gtt atg gaa gca cca tta aat tct ctc ctt cca agc gct ggt      2067
Asp Ile Val Met Glu Ala Pro Leu Asn Ser Leu Leu Pro Ser Ala Gly
590                 595                 600                 605 gct tct gta gtg cag ccc agt gta tcc cca ctg gaa gca cct cct cca      2115
Ala Ser Val Val Gln Pro Ser Val Ser Pro Leu Glu Ala Pro Pro Pro
                610                 615                 620 gtt agt tat gac agt ata aag ctt gag cct gaa aac ccc cca cca tat      2163
Val Ser Tyr Asp Ser Ile Lys Leu Glu Pro Glu Asn Pro Pro Pro Tyr
            625                 630                 635 gaa gaa gcc atg aat gta gca cta aaa gct ttg gga aca aag gaa gga      2211
Glu Glu Ala Met Asn Val Ala Leu Lys Ala Leu Gly Thr Lys Glu Gly
        640                 645                 650
```

```
ata aaa gag cct gaa agt ttt aat gca gct gtt cag gaa aca gaa gct    2259
Ile Lys Glu Pro Glu Ser Phe Asn Ala Ala Val Gln Glu Thr Glu Ala
655                 660                 665 cct tat ata tcc att gcg tgt gat tta att aaa gaa aca aag ctc tcc    2307
Pro Tyr Ile Ser Ile Ala Cys Asp Leu Ile Lys Glu Thr Lys Leu Ser
670                 675                 680                 685 act gag cca agt cca gat ttc tct aat tat tca gaa ata gca aaa ttc    2355
Thr Glu Pro Ser Pro Asp Phe Ser Asn Tyr Ser Glu Ile Ala Lys Phe
                690                 695                 700 gag aag tcg gtg ccc gaa cac gct gag cta gtg gag gat tcc tca cct    2403
Glu Lys Ser Val Pro Glu His Ala Glu Leu Val Glu Asp Ser Ser Pro
    705                 710                 715 gaa tct gaa cca gtt gac tta ttt agt gat gat tcg att cct gaa gtc    2451
Glu Ser Glu Pro Val Asp Leu Phe Ser Asp Asp Ser Ile Pro Glu Val
720                 725                 730 cca caa aca caa gag gag gct gtg atg ctc atg aag gag agt ctc act    2499
Pro Gln Thr Gln Glu Glu Ala Val Met Leu Met Lys Glu Ser Leu Thr
735                 740                 745 gaa gtg tct gag aca gta gcc cag cac aaa gag gag aga ctt agt gcc    2547
Glu Val Ser Glu Thr Val Ala Gln His Lys Glu Glu Arg Leu Ser Ala
750                 755                 760                 765 tca cct cag gag cta gga aag cca tat tta gag tct ttt cag ccc aat    2595
Ser Pro Gln Glu Leu Gly Lys Pro Tyr Leu Glu Ser Phe Gln Pro Asn
                770                 775                 780 tta cat agt aca aaa gat gct gca tct aat gac att cca aca ttg acc    2643
Leu His Ser Thr Lys Asp Ala Ala Ser Asn Asp Ile Pro Thr Leu Thr
    785                 790                 795 aaa aag gag aaa att tct ttg caa atg gaa gag ttt aat act gca att    2691
Lys Lys Glu Lys Ile Ser Leu Gln Met Glu Glu Phe Asn Thr Ala Ile
800                 805                 810 tat tca aat gat gac tta ctt tct tct aag gaa gac aaa ata aaa gaa    2739
Tyr Ser Asn Asp Asp Leu Leu Ser Ser Lys Glu Asp Lys Ile Lys Glu
815                 820                 825 agt gaa aca ttt tca gat tca tct ccg att gag ata ata gat gaa ttt    2787
Ser Glu Thr Phe Ser Asp Ser Ser Pro Ile Glu Ile Ile Asp Glu Phe
830                 835                 840                 845 ccc acg ttt gtc agt gct aaa gat gat tct cct aaa tta gcc aag gag    2835
Pro Thr Phe Val Ser Ala Lys Asp Asp Ser Pro Lys Leu Ala Lys Glu
                850                 855                 860 tac act gat cta gaa gta tcc gac aaa agt gaa att gct aat atc caa    2883
Tyr Thr Asp Leu Glu Val Ser Asp Lys Ser Glu Ile Ala Asn Ile Gln
    865                 870                 875 agc ggg gca gat tca ttg cct tgc tta gaa ttg ccc tgt gac ctt tct    2931
Ser Gly Ala Asp Ser Leu Pro Cys Leu Glu Leu Pro Cys Asp Leu Ser
880                 885                 890 ttc aag aat ata tat cct aaa gat gaa gta cat gtt tca gat gaa ttc    2979
Phe Lys Asn Ile Tyr Pro Lys Asp Glu Val His Val Ser Asp Glu Phe
895                 900                 905 tcc gaa aat agg tcc agt gta tct aag gca tcc ata tcg cct tca aat    3027
Ser Glu Asn Arg Ser Ser Val Ser Lys Ala Ser Ile Ser Pro Ser Asn
910                 915                 920                 925 gtc tct gct ttg gaa cct cag aca gaa atg ggc agc ata gtt aaa tcc    3075
Val Ser Ala Leu Glu Pro Gln Thr Glu Met Gly Ser Ile Val Lys Ser
                930                 935                 940 aaa tca ctt acg aaa gaa gca gag aaa aaa ctt cct tct gac aca gag    3123
Lys Ser Leu Thr Lys Glu Ala Glu Lys Lys Leu Pro Ser Asp Thr Glu
    945                 950                 955 aaa gag gac aga tcc ctg tca gct gta ttg tca gca gag ctg agt aaa    3171
Lys Glu Asp Arg Ser Leu Ser Ala Val Leu Ser Ala Glu Leu Ser Lys
960                 965                 970
```

```
act tca gtt gtt gac ctc ctc tac tgg aga gac att aag aag act gga      3219
Thr Ser Val Val Asp Leu Leu Tyr Trp Arg Asp Ile Lys Lys Thr Gly
    975                 980                 985 gtg gtg ttt ggt gcc agc tta ttc ctg ctg ctg  tct ctg aca gtg ttc     3267
Val Val Phe Gly Ala Ser Leu Phe Leu Leu Leu  Ser Leu Thr Val Phe
990                 995                 1000                 1005 agc att gtc agt gta  acg gcc tac att gcc  ttg gcc ctg ctc tcg        3312
Ser Ile Val Ser Val  Thr Ala Tyr Ile Ala  Leu Ala Leu Leu Ser
                1010                 1015                 1020 gtg act atc agc ttt  agg ata tat aag ggc  gtg atc cag gct atc        3357
Val Thr Ile Ser Phe  Arg Ile Tyr Lys Gly  Val Ile Gln Ala Ile
                1025                 1030                 1035 cag aaa tca gat gaa  ggc cac cca ttc agg  gca tat tta gaa tct        3402
Gln Lys Ser Asp Glu  Gly His Pro Phe Arg  Ala Tyr Leu Glu Ser
                1040                 1045                 1050 gaa gtt gct ata tca  gag gaa ttg gtt cag  aaa tac agt aat tct        3447
Glu Val Ala Ile Ser  Glu Glu Leu Val Gln  Lys Tyr Ser Asn Ser
                1055                 1060                 1065 gct ctt ggt cat gtg  aac agc aca ata aaa  gaa ctg agg cgg ctt        3492
Ala Leu Gly His Val  Asn Ser Thr Ile Lys  Glu Leu Arg Arg Leu
                1070                 1075                 1080 ttc tta gtt gat gat  tta gtt gat tcc ctg  aag ttt gca gtg ttg        3537
Phe Leu Val Asp Asp  Leu Val Asp Ser Leu  Lys Phe Ala Val Leu
                1085                 1090                 1095 atg tgg gtg ttt act  tat gtt ggt gcc ttg  ttc aat ggt ctg aca        3582
Met Trp Val Phe Thr  Tyr Val Gly Ala Leu  Phe Asn Gly Leu Thr
                1100                 1105                 1110 cta ctg att tta gct  ctg atc tca ctc ttc  agt att cct gtt att        3627
Leu Leu Ile Leu Ala  Leu Ile Ser Leu Phe  Ser Ile Pro Val Ile
                1115                 1120                 1125 tat gaa cgg cat cag  gtg cag ata gat cat  tat cta gga ctt gca        3672
Tyr Glu Arg His Gln  Val Gln Ile Asp His  Tyr Leu Gly Leu Ala
                1130                 1135                 1140 aac aag agt gtt aag  gat gcc atg gcc aaa  atc caa gca aaa atc        3717
Asn Lys Ser Val Lys  Asp Ala Met Ala Lys  Ile Gln Ala Lys Ile
                1145                 1150                 1155 cct gga ttg aag cgc  aaa gca gat tga aaaagccccca aacagaagtt          3764
Pro Gly Leu Lys Arg  Lys Ala Asp
                1160 catctttaaa ggggacactc acttgattac gggggtggga gggtcagggg tgagcccttg    3824 gtggccgtgc ggtttcagct ctttatttt agcagtgcac tgtttgagga aaaattacct    3884 gtcttgactt cctgtgttta tcatcttaag tattgtaagc tgctgtgtat ggatctcatt    3944 gtagtcacac ttgtcttccc caatgaggcg cctggtgaat aaaggactcg ggaaagctg    4004 tgcattgtat ctgctgcagg gtagtctagc tgtatgcaga gagttgtaaa gaaggcaaat    4064 ctggggggcag ggaaaaccct tttcacagtg tactgtgttt ggtcagtgta aaactgatgc    4124 agattttct gaaatgaaat gtttagatga gagcatacta ctaaagcaga gtggaaaact    4184 ctgtctttat ggtgtgttct aggtgtattg tgaattact gttatattgc caatataagt    4244 aaatatagac ctaatctata tatagtgttt cacaaagctt agatctttaa ccttgcagct    4304 gccccacagt gcttgacctc tgagtcattg gttatgcagt gtagtccaag cacataaact    4364 aggaagagaa atgtatttgt aggagtgcta cctaccacct gttttcaaga aaatatagaa    4424 ctccaacaaa aatatagaat gtcatttcaa agacttactg tatgtatagt taattttgtc    4484 acagactctg aaattctatg gactgaattt catgcttcca aatgtttgca gttatcaaac    4544
```

-continued

```
attgttatgc aagaaatcat aaaatgaaga cttataccat tgtggtttaa gccgtactga    4604
attatctgtg gaatgcattg tgaactgtaa aagcaaagta tcaataaagc ttatagatct    4664
taaaaaaaaa aaaaaaaaa                                                 4684
```

<210> SEQ ID NO 18
<211> LENGTH: 1163
<212> TYPE: PRT
<213> ORGANISM: Rattus norvegicus

<400> SEQUENCE: 18

```
Met Glu Asp Ile Asp Gln Ser Ser Leu Val Ser Ser Thr Asp Ser
1               5                   10                  15

Pro Pro Arg Pro Pro Ala Phe Lys Tyr Gln Phe Val Thr Glu Pro
                20                  25                  30

Glu Asp Glu Glu Asp Glu Glu Glu Glu Asp Glu Glu Glu Asp Asp
                35                  40                  45

Glu Asp Leu Glu Glu Leu Glu Val Leu Glu Arg Lys Pro Ala Ala Gly
        50                  55                  60

Leu Ser Ala Ala Val Pro Ala Ala Ala Pro Leu Leu Asp
65                  70                  75              80

Phe Ser Ser Asp Ser Val Pro Ala Pro Arg Gly Pro Leu Pro Ala
                85                  90                  95

Ala Pro Pro Ala Ala Pro Glu Arg Gln Pro Ser Trp Glu Arg Ser Pro
                100                 105                 110

Ala Ala Pro Ala Pro Ser Leu Pro Pro Ala Ala Val Leu Pro Ser
                115                 120                 125

Lys Leu Pro Glu Asp Asp Glu Pro Pro Ala Arg Pro Pro Pro Pro
130                 135                 140

Pro Ala Gly Ala Ser Pro Leu Ala Glu Pro Ala Ala Pro Pro Ser Thr
145                 150                 155             160

Pro Ala Ala Pro Lys Arg Arg Gly Ser Gly Ser Val Asp Glu Thr Leu
                165                 170                 175

Phe Ala Leu Pro Ala Ala Ser Glu Pro Val Ile Pro Ser Ser Ala Glu
                180                 185                 190

Lys Ile Met Asp Leu Met Glu Gln Pro Gly Asn Thr Val Ser Ser Gly
                195                 200                 205

Gln Glu Asp Phe Pro Ser Val Leu Leu Glu Thr Ala Ala Ser Leu Pro
210                 215                 220

Ser Leu Ser Pro Leu Ser Thr Val Ser Phe Lys Glu His Gly Tyr Leu
225                 230                 235             240

Gly Asn Leu Ser Ala Val Ser Ser Ser Glu Gly Thr Ile Glu Glu Thr
                245                 250                 255

Leu Asn Glu Ala Ser Lys Glu Leu Pro Glu Arg Ala Thr Asn Pro Phe
                260                 265                 270

Val Asn Arg Asp Leu Ala Glu Phe Ser Glu Leu Glu Tyr Ser Glu Met
                275                 280                 285

Gly Ser Ser Phe Lys Gly Ser Pro Lys Gly Glu Ser Ala Ile Leu Val
                290                 295                 300

Glu Asn Thr Lys Glu Glu Val Ile Val Arg Ser Lys Asp Lys Glu Asp
305                 310                 315             320

Leu Val Cys Ser Ala Ala Leu His Ser Pro Gln Glu Ser Pro Val Gly
                325                 330                 335

Lys Glu Asp Arg Val Val Ser Pro Glu Lys Thr Met Asp Ile Phe Asn
                340                 345                 350
```

-continued

```
Glu Met Gln Met Ser Val Val Ala Pro Val Arg Glu Glu Tyr Ala Asp
            355                 360                 365

Phe Lys Pro Phe Glu Gln Ala Trp Glu Val Lys Asp Thr Tyr Glu Gly
            370                 375                 380

Ser Arg Asp Val Leu Ala Ala Arg Ala Asn Val Glu Ser Lys Val Asp
385                 390                 395                 400

Arg Lys Cys Leu Glu Asp Ser Leu Glu Gln Lys Ser Leu Gly Lys Asp
                405                 410                 415

Ser Glu Gly Arg Asn Glu Asp Ala Ser Phe Pro Ser Thr Pro Glu Pro
            420                 425                 430

Val Lys Asp Ser Ser Arg Ala Tyr Ile Thr Cys Ala Ser Phe Thr Ser
            435                 440                 445

Ala Thr Glu Ser Thr Thr Ala Asn Thr Phe Pro Leu Leu Glu Asp His
            450                 455                 460

Thr Ser Glu Asn Lys Thr Asp Glu Lys Ile Glu Glu Arg Lys Ala
465                 470                 475                 480

Gln Ile Ile Thr Glu Lys Thr Ser Pro Lys Thr Ser Asn Pro Phe Leu
                485                 490                 495

Val Ala Val Gln Asp Ser Glu Ala Asp Tyr Val Thr Thr Asp Thr Leu
            500                 505                 510

Ser Lys Val Thr Glu Ala Ala Val Ser Asn Met Pro Glu Gly Leu Thr
            515                 520                 525

Pro Asp Leu Val Gln Glu Ala Cys Glu Ser Glu Leu Asn Glu Ala Thr
            530                 535                 540

Gly Thr Lys Ile Ala Tyr Glu Thr Lys Val Asp Leu Val Gln Thr Ser
545                 550                 555                 560

Glu Ala Ile Gln Glu Ser Leu Tyr Pro Thr Ala Gln Leu Cys Pro Ser
                565                 570                 575

Phe Glu Glu Ala Glu Ala Thr Pro Ser Pro Val Leu Pro Asp Ile Val
            580                 585                 590

Met Glu Ala Pro Leu Asn Ser Leu Leu Pro Ser Ala Gly Ala Ser Val
            595                 600                 605

Val Gln Pro Ser Val Ser Pro Leu Glu Ala Pro Pro Val Ser Tyr
            610                 615                 620

Asp Ser Ile Lys Leu Glu Pro Glu Asn Pro Pro Tyr Glu Glu Ala
625                 630                 635                 640

Met Asn Val Ala Leu Lys Ala Leu Gly Thr Lys Glu Gly Ile Lys Glu
                645                 650                 655

Pro Glu Ser Phe Asn Ala Ala Val Gln Glu Thr Glu Ala Pro Tyr Ile
            660                 665                 670

Ser Ile Ala Cys Asp Leu Ile Lys Glu Thr Lys Leu Ser Thr Glu Pro
            675                 680                 685

Ser Pro Asp Phe Ser Asn Tyr Ser Glu Ile Ala Lys Phe Glu Lys Ser
            690                 695                 700

Val Pro Glu His Ala Glu Leu Val Glu Asp Ser Ser Pro Glu Ser Glu
705                 710                 715                 720

Pro Val Asp Leu Phe Ser Asp Asp Ser Ile Pro Glu Val Pro Gln Thr
                725                 730                 735

Gln Glu Glu Ala Val Met Leu Met Lys Glu Ser Leu Thr Glu Val Ser
            740                 745                 750

Glu Thr Val Ala Gln His Lys Glu Glu Arg Leu Ser Ala Ser Pro Gln
            755                 760                 765
```

-continued

```
Glu Leu Gly Lys Pro Tyr Leu Glu Ser Phe Gln Pro Asn Leu His Ser
770                 775                 780

Thr Lys Asp Ala Ala Ser Asn Asp Ile Pro Thr Leu Thr Lys Lys Glu
785                 790                 795                 800

Lys Ile Ser Leu Gln Met Glu Glu Phe Asn Thr Ala Ile Tyr Ser Asn
                805                 810                 815

Asp Asp Leu Leu Ser Ser Lys Gly Asp Lys Ile Lys Glu Ser Glu Thr
                820                 825                 830

Phe Ser Asp Ser Ser Pro Ile Glu Ile Ile Asp Glu Phe Pro Thr Phe
                835                 840                 845

Val Ser Ala Lys Asp Asp Ser Pro Lys Leu Ala Lys Glu Tyr Thr Asp
850                 855                 860

Leu Glu Val Ser Asp Lys Ser Glu Ile Ala Asn Ile Gln Ser Gly Ala
865                 870                 875                 880

Asp Ser Leu Pro Cys Leu Glu Leu Pro Cys Asp Leu Ser Phe Lys Asn
                885                 890                 895

Ile Tyr Pro Lys Asp Glu Val His Val Ser Asp Glu Phe Ser Glu Asn
                900                 905                 910

Arg Ser Ser Val Ser Lys Ala Ser Ile Ser Pro Ser Asn Val Ser Ala
                915                 920                 925

Leu Glu Pro Gln Thr Glu Met Gly Ser Ile Val Lys Ser Lys Ser Leu
930                 935                 940

Thr Lys Glu Ala Glu Lys Lys Leu Pro Ser Asp Thr Glu Lys Glu Asp
945                 950                 955                 960

Arg Ser Leu Ser Ala Val Leu Ser Ala Glu Leu Ser Lys Thr Ser Val
                965                 970                 975

Val Asp Leu Leu Tyr Trp Arg Asp Ile Lys Lys Thr Gly Val Val Phe
                980                 985                 990

Gly Ala Ser Leu Phe Leu Leu Leu Ser Leu Thr Val Phe Ser Ile Val
                995                 1000                1005

Ser Val Thr Ala Tyr Ile Ala Leu Ala Leu Leu Ser Val Thr Ile
        1010                1015                1020

Ser Phe Arg Ile Tyr Lys Gly Val Ile Gln Ala Ile Gln Lys Ser
        1025                1030                1035

Asp Glu Gly His Pro Phe Arg Ala Tyr Leu Glu Ser Glu Val Ala
        1040                1045                1050

Ile Ser Glu Glu Leu Val Gln Lys Tyr Ser Asn Ser Ala Leu Gly
        1055                1060                1065

His Val Asn Ser Thr Ile Lys Glu Leu Arg Arg Leu Phe Leu Val
        1070                1075                1080

Asp Asp Leu Val Asp Ser Leu Lys Phe Ala Val Leu Met Trp Val
        1085                1090                1095

Phe Thr Tyr Val Gly Ala Leu Phe Asn Gly Leu Thr Leu Leu Ile
        1100                1105                1110

Leu Ala Leu Ile Ser Leu Phe Ser Ile Pro Val Ile Tyr Glu Arg
        1115                1120                1125

His Gln Val Gln Ile Asp His Tyr Leu Gly Leu Ala Asn Lys Ser
        1130                1135                1140

Val Lys Asp Ala Met Ala Lys Ile Gln Ala Lys Ile Pro Gly Leu
        1145                1150                1155

Lys Arg Lys Ala Asp
1160
```

<210> SEQ ID NO 19
<211> LENGTH: 18
<212> TYPE: PRT
<213> ORGANISM: Rattus norvegicus

<400> SEQUENCE: 19

```
Ser Tyr Asp Ser Ile Lys Leu Glu Pro Glu Asn Pro Pro Tyr Glu
1               5                   10                  15

Glu Ala
```

<210> SEQ ID NO 20
<211> LENGTH: 360
<212> TYPE: PRT
<213> ORGANISM: Rattus norvegicus

<400> SEQUENCE: 20

```
Met Glu Asp Ile Asp Gln Ser Ser Leu Val Ser Ser Thr Asp Ser
1               5                   10                  15

Pro Pro Arg Pro Pro Ala Phe Lys Tyr Gln Phe Val Thr Glu Pro
                20                  25                  30

Glu Asp Glu Glu Asp Glu Glu Glu Glu Asp Glu Glu Glu Asp Asp
            35                  40                  45

Glu Asp Leu Glu Glu Leu Glu Val Leu Glu Arg Lys Pro Ala Ala Gly
        50                  55                  60

Leu Ser Ala Ala Ala Val Pro Pro Ala Ala Ala Pro Leu Leu Asp
65                  70                  75                  80

Phe Ser Asp Ser Val Pro Ala Pro Arg Gly Pro Leu Pro Ala
                85                  90                  95

Ala Pro Pro Ala Ala Pro Glu Arg Gln Pro Ser Trp Glu Arg Ser Pro
                100                 105                 110

Ala Ala Pro Ala Pro Ser Leu Pro Pro Ala Ala Val Leu Pro Ser
            115                 120                 125

Lys Leu Pro Glu Asp Asp Glu Pro Pro Ala Arg Pro Pro Pro Pro
130                 135                 140

Pro Ala Gly Ala Ser Pro Leu Ala Glu Pro Ala Ala Pro Pro Ser Thr
145                 150                 155                 160

Pro Ala Ala Pro Lys Arg Arg Gly Ser Gly Ser Val Val Asp Leu
                165                 170                 175

Leu Tyr Trp Arg Asp Ile Lys Lys Thr Gly Val Val Phe Gly Ala Ser
                180                 185                 190

Leu Phe Leu Leu Leu Ser Leu Thr Val Phe Ser Ile Val Ser Val Thr
            195                 200                 205

Ala Tyr Ile Ala Leu Ala Leu Leu Ser Val Thr Ile Ser Phe Arg Ile
210                 215                 220

Tyr Lys Gly Val Ile Gln Ala Ile Gln Lys Ser Asp Glu Gly His Pro
225                 230                 235                 240

Phe Arg Ala Tyr Leu Glu Ser Glu Val Ala Ile Ser Glu Glu Leu Val
                245                 250                 255

Gln Lys Tyr Ser Asn Ser Ala Leu Gly His Val Asn Ser Thr Ile Lys
            260                 265                 270

Glu Leu Arg Arg Leu Phe Leu Val Asp Asp Leu Val Asp Ser Leu Lys
        275                 280                 285

Phe Ala Val Leu Met Trp Val Phe Thr Tyr Val Gly Ala Leu Phe Asn
    290                 295                 300

Gly Leu Thr Leu Leu Ile Leu Ala Leu Ile Ser Leu Phe Ser Ile Pro
305                 310                 315                 320
```

Val Ile Tyr Glu Arg His Gln Val Gln Ile Asp His Tyr Leu Gly Leu
              325                 330                 335

Ala Asn Lys Ser Val Lys Asp Ala Met Ala Lys Ile Gln Ala Lys Ile
              340                 345                 350

Pro Gly Leu Lys Arg Lys Ala Asp
              355                 360

<210> SEQ ID NO 21
<211> LENGTH: 199
<212> TYPE: PRT
<213> ORGANISM: Rattus norvegicus

<400> SEQUENCE: 21

Met Asp Gly Gln Lys Lys His Trp Lys Asp Lys Val Val Asp Leu Leu
1               5                   10                  15

Tyr Trp Arg Asp Ile Lys Lys Thr Gly Val Val Phe Gly Ala Ser Leu
              20                  25                  30

Phe Leu Leu Leu Ser Leu Thr Val Phe Ser Ile Val Ser Val Thr Ala
              35                  40                  45

Tyr Ile Ala Leu Ala Leu Leu Ser Val Thr Ile Ser Phe Arg Ile Tyr
        50                  55                  60

Lys Gly Val Ile Gln Ala Ile Gln Lys Ser Asp Glu Gly His Pro Phe
65                  70                  75                  80

Arg Ala Tyr Leu Glu Ser Glu Val Ala Ile Ser Glu Glu Leu Val Gln
              85                  90                  95

Lys Tyr Ser Asn Ser Ala Leu Gly His Val Asn Ser Thr Ile Lys Glu
              100                 105                 110

Leu Arg Arg Leu Phe Leu Val Asp Asp Leu Val Asp Ser Leu Lys Phe
        115                 120                 125

Ala Val Leu Met Trp Val Phe Thr Tyr Val Gly Ala Leu Phe Asn Gly
    130                 135                 140

Leu Thr Leu Leu Ile Leu Ala Leu Ile Ser Leu Phe Ser Ile Pro Val
145                 150                 155                 160

Ile Tyr Glu Arg His Gln Val Gln Ile Asp His Tyr Leu Gly Leu Ala
              165                 170                 175

Asn Lys Ser Val Lys Asp Ala Met Ala Lys Ile Gln Ala Lys Ile Pro
              180                 185                 190

Gly Leu Lys Arg Lys Ala Asp
        195

<210> SEQ ID NO 22
<211> LENGTH: 3579
<212> TYPE: DNA
<213> ORGANISM: Homo sapiens
<220> FEATURE:
<221> NAME/KEY: CDS
<222> LOCATION: (1)..(3579)
<223> OTHER INFORMATION:

<400> SEQUENCE: 22

| | | |
|---|---|---|
| atg gaa gac ctg gac cag tct cct ctg gtc tcg tcc tcg gac agc cca<br>Met Glu Asp Leu Asp Gln Ser Pro Leu Val Ser Ser Ser Asp Ser Pro<br>1               5                   10              15 | | 48 |
| ccc cgg ccg cag ccc gcg ttc aag tac cag ttc gtg agg gag ccc gag<br>Pro Arg Pro Gln Pro Ala Phe Lys Tyr Gln Phe Val Arg Glu Pro Glu<br>               20                   25                   30 | | 96 |
| gac gag gag gaa gaa gag gag gag gaa gag gag gac gag gac gaa gac<br>Asp Glu Glu Glu Glu Glu Glu Glu Glu Glu Asp Glu Asp Glu Asp | | 144 |

-continued

```
              35                  40                  45
ctg gag gag ctg gag gtg ctg gag agg aag ccc gcc gcc ggg ctg tcc        192
Leu Glu Glu Leu Glu Val Leu Glu Arg Lys Pro Ala Ala Gly Leu Ser
 50                  55                  60 gcg gcc cca gtg ccc acc gcc cct gcc gcc ggc gcg ccc ctg atg gac        240
Ala Ala Pro Val Pro Thr Ala Pro Ala Ala Gly Ala Pro Leu Met Asp
 65                  70                  75                  80 ttc gga aat gac ttc gtg ccg ccg gcg ccc cgg gga ccc ctg ccg gcc        288
Phe Gly Asn Asp Phe Val Pro Pro Ala Pro Arg Gly Pro Leu Pro Ala
                     85                  90                  95 gct ccc ccc gtc gcc ccg gag cgg cag ccg tct tgg gac ccg agc ccg        336
Ala Pro Pro Val Ala Pro Glu Arg Gln Pro Ser Trp Asp Pro Ser Pro
100                 105                 110 gtg tcg tcg acc gtg ccc gcg cca tcc ccg ctg tct gct gcc gca gtc        384
Val Ser Ser Thr Val Pro Ala Pro Ser Pro Leu Ser Ala Ala Ala Val
            115                 120                 125 tcg ccc tcc aag ctc cct gag gac gac gag cct ccg gcc cgg cct ccc        432
Ser Pro Ser Lys Leu Pro Glu Asp Asp Glu Pro Pro Ala Arg Pro Pro
130                 135                 140 cct cct ccc ccg gcc agc gtg agc ccc cag gca gag ccc gtg tgg acc        480
Pro Pro Pro Pro Ala Ser Val Ser Pro Gln Ala Glu Pro Val Trp Thr
145                 150                 155                 160 ccg cca gcc ccg gct ccc gcc gcg ccc ccc tcc acc ccg gcc gcg ccc        528
Pro Pro Ala Pro Ala Pro Ala Ala Pro Pro Ser Thr Pro Ala Ala Pro
                    165                 170                 175 aag cgc agg ggc tcc tcg ggc tca gtg gat gag acc ctt ttt gct ctt        576
Lys Arg Arg Gly Ser Ser Gly Ser Val Asp Glu Thr Leu Phe Ala Leu
                180                 185                 190 cct gct gca tct gag cct gtg ata cgc tcc tct gca gaa aat atg gac        624
Pro Ala Ala Ser Glu Pro Val Ile Arg Ser Ser Ala Glu Asn Met Asp
            195                 200                 205 ttg aag gag cag cca ggt aac act att tcg gct ggt caa gag gat ttc        672
Leu Lys Glu Gln Pro Gly Asn Thr Ile Ser Ala Gly Gln Glu Asp Phe
210                 215                 220 cca tct gtc ctg ctt gaa act gct gct tct ctt cct tct ctg tct cct        720
Pro Ser Val Leu Leu Glu Thr Ala Ala Ser Leu Pro Ser Leu Ser Pro
225                 230                 235                 240 ctc tca gcc gct tct ttc aaa gaa cat gaa tac ctt ggt aat ttg tca        768
Leu Ser Ala Ala Ser Phe Lys Glu His Glu Tyr Leu Gly Asn Leu Ser
                    245                 250                 255 aca gta tta ccc act gaa gga aca ctt caa gaa aat gtc agt gaa gct        816
Thr Val Leu Pro Thr Glu Gly Thr Leu Gln Glu Asn Val Ser Glu Ala
                260                 265                 270 tct aaa gag gtc tca gag aag gca aaa act cta ctc ata gat aga gat        864
Ser Lys Glu Val Ser Glu Lys Ala Lys Thr Leu Leu Ile Asp Arg Asp
            275                 280                 285 tta aca gag ttt tca gaa tta gaa tac tca gaa atg gga tca tcg ttc        912
Leu Thr Glu Phe Ser Glu Leu Glu Tyr Ser Glu Met Gly Ser Ser Phe
290                 295                 300 agt gtc tct cca aaa gca gaa tct gcc gta ata gta gca aat cct agg        960
Ser Val Ser Pro Lys Ala Glu Ser Ala Val Ile Val Ala Asn Pro Arg
305                 310                 315                 320 gaa gaa ata atc gtg aaa aat aaa gat gaa gaa gag aag tta gtt agt       1008
Glu Glu Ile Ile Val Lys Asn Lys Asp Glu Glu Glu Lys Leu Val Ser
                    325                 330                 335 aat aac atc ctt cat aat caa caa gag tta cct aca gct ctt act aaa       1056
Asn Asn Ile Leu His Asn Gln Gln Glu Leu Pro Thr Ala Leu Thr Lys
                340                 345                 350 ttg gtt aaa gag gat gaa gtt gtg tct tca gaa aaa gca aaa gac agt       1104
```

```
                -continued

Leu Val Lys Glu Asp Glu Val Val Ser Ser Glu Lys Ala Lys Asp Ser
        355                 360                 365 ttt aat gaa aag aga gtt gca gtg gaa gct cct atg agg gag gaa tat      1152
Phe Asn Glu Lys Arg Val Ala Val Glu Ala Pro Met Arg Glu Glu Tyr
        370                 375                 380 gca gac ttc aaa cca ttt gag cga gta tgg gaa gtg aaa gat agt aag      1200
Ala Asp Phe Lys Pro Phe Glu Arg Val Trp Glu Val Lys Asp Ser Lys
385                 390                 395                 400 gaa gat agt gat atg ttg gct gct gga ggt aaa atc gag agc aac ttg      1248
Glu Asp Ser Asp Met Leu Ala Ala Gly Gly Lys Ile Glu Ser Asn Leu
                405                 410                 415 gaa agt aaa gtg gat aaa aaa tgt ttt gca gat agc ctt gag caa act      1296
Glu Ser Lys Val Asp Lys Lys Cys Phe Ala Asp Ser Leu Glu Gln Thr
            420                 425                 430 aat cac gaa aaa gat agt gag agt agt aat gat gat act tct ttc ccc      1344
Asn His Glu Lys Asp Ser Glu Ser Ser Asn Asp Asp Thr Ser Phe Pro
        435                 440                 445 agt acg cca gaa ggt ata aag gat cgt cca gga gca tat atc aca tgt      1392
Ser Thr Pro Glu Gly Ile Lys Asp Arg Pro Gly Ala Tyr Ile Thr Cys
    450                 455                 460 gct ccc ttt aac cca gca gca act gag agc att gca aca aac att ttt      1440
Ala Pro Phe Asn Pro Ala Ala Thr Glu Ser Ile Ala Thr Asn Ile Phe
465                 470                 475                 480 cct ttg tta gga gat cct act tca gaa aat aag acc gat gaa aaa aaa      1488
Pro Leu Leu Gly Asp Pro Thr Ser Glu Asn Lys Thr Asp Glu Lys Lys
                485                 490                 495 ata gaa gaa aag aag gcc caa ata gta aca gag aag aat act agc acc      1536
Ile Glu Glu Lys Lys Ala Gln Ile Val Thr Glu Lys Asn Thr Ser Thr
            500                 505                 510 aaa aca tca aac cct ttt ctt gta gca gca cag gat tct gag aca gat      1584
Lys Thr Ser Asn Pro Phe Leu Val Ala Ala Gln Asp Ser Glu Thr Asp
        515                 520                 525 tat gtc aca aca gat aat tta aca aag gtg act gag gaa gtc gtg gca      1632
Tyr Val Thr Thr Asp Asn Leu Thr Lys Val Thr Glu Glu Val Val Ala
    530                 535                 540 aac atg cct gaa ggc ctg act cca gat tta gta cag gaa gca tgt gaa      1680
Asn Met Pro Glu Gly Leu Thr Pro Asp Leu Val Gln Glu Ala Cys Glu
545                 550                 555                 560 agt gaa ttg aat gaa gtt act ggt aca aag att gct tat gaa aca aaa      1728
Ser Glu Leu Asn Glu Val Thr Gly Thr Lys Ile Ala Tyr Glu Thr Lys
                565                 570                 575 atg gac ttg gtt caa aca tca gaa gtt atg caa gag tca ctc tat cct      1776
Met Asp Leu Val Gln Thr Ser Glu Val Met Gln Glu Ser Leu Tyr Pro
            580                 585                 590 gca gca cag ctt tgc cca tca ttt gaa gag tca gaa gct act cct tca      1824
Ala Ala Gln Leu Cys Pro Ser Phe Glu Glu Ser Glu Ala Thr Pro Ser
        595                 600                 605 cca gtt ttg cct gac att gtt atg gaa gca cca ttg aat tct gca gtt      1872
Pro Val Leu Pro Asp Ile Val Met Glu Ala Pro Leu Asn Ser Ala Val
    610                 615                 620 cct agt gct ggt gct tcc gtg ata cag ccc agc tca tca cca tta gaa      1920
Pro Ser Ala Gly Ala Ser Val Ile Gln Pro Ser Ser Ser Pro Leu Glu
625                 630                 635                 640 gct tct tca gtt aat tat gaa agc ata aaa cat gag cct gaa aac ccc      1968
Ala Ser Ser Val Asn Tyr Glu Ser Ile Lys His Glu Pro Glu Asn Pro
                645                 650                 655 cca cca tat gaa gag gcc atg agt gta tca cta aaa aaa gta tca gga      2016
Pro Pro Tyr Glu Glu Ala Met Ser Val Ser Leu Lys Lys Val Ser Gly
            660                 665                 670
```

```
ata aag gaa gaa att aaa gag cct gaa aat att aat gca gct ctt caa      2064
Ile Lys Glu Glu Ile Lys Glu Pro Glu Asn Ile Asn Ala Ala Leu Gln
            675                 680                 685 gaa aca gaa gct cct tat ata tct att gca tgt gat tta att aaa gaa      2112
Glu Thr Glu Ala Pro Tyr Ile Ser Ile Ala Cys Asp Leu Ile Lys Glu
    690                 695                 700 aca aag ctt tct gct gaa cca gct ccg gat ttc tct gat tat tca gaa      2160
Thr Lys Leu Ser Ala Glu Pro Ala Pro Asp Phe Ser Asp Tyr Ser Glu
705                 710                 715                 720 atg gca aaa gtt gaa cag cca gtg cct gat cat tct gag cta gtt gaa      2208
Met Ala Lys Val Glu Gln Pro Val Pro Asp His Ser Glu Leu Val Glu
                725                 730                 735 gat tcc tca cct gat tct gaa cca gtt gac tta ttt agt gat gat tca      2256
Asp Ser Ser Pro Asp Ser Glu Pro Val Asp Leu Phe Ser Asp Asp Ser
            740                 745                 750 ata cct gac gtt cca caa aaa caa gat gaa act gtg atg ctt gtg aaa      2304
Ile Pro Asp Val Pro Gln Lys Gln Asp Glu Thr Val Met Leu Val Lys
    755                 760                 765 gaa agt ctc act gag act tca ttt gag tca atg ata gaa tat gaa aat      2352
Glu Ser Leu Thr Glu Thr Ser Phe Glu Ser Met Ile Glu Tyr Glu Asn
770                 775                 780 aag gaa aaa ctc agt gct ttg cca cct gag gga gga aag cca tat ttg      2400
Lys Glu Lys Leu Ser Ala Leu Pro Pro Glu Gly Gly Lys Pro Tyr Leu
785                 790                 795                 800 gaa tct ttt aag ctc agt tta gat aac aca aaa gat acc ctg tta cct      2448
Glu Ser Phe Lys Leu Ser Leu Asp Asn Thr Lys Asp Thr Leu Leu Pro
            805                 810                 815 gat gaa gtt tca aca ttg agc aaa aag gag aaa att cct ttg cag atg      2496
Asp Glu Val Ser Thr Leu Ser Lys Lys Glu Lys Ile Pro Leu Gln Met
    820                 825                 830 gag gag ctc agt act gca gtt tat tca aat gat gac tta ttt att tct      2544
Glu Glu Leu Ser Thr Ala Val Tyr Ser Asn Asp Asp Leu Phe Ile Ser
835                 840                 845 aag gaa gca cag ata aga gaa act gaa acg ttt tca gat tca tct cca      2592
Lys Glu Ala Gln Ile Arg Glu Thr Glu Thr Phe Ser Asp Ser Ser Pro
850                 855                 860 att gaa att ata gat gag ttc cct aca ttg atc agt tct aaa act gat      2640
Ile Glu Ile Ile Asp Glu Phe Pro Thr Leu Ile Ser Ser Lys Thr Asp
865                 870                 875                 880 tca ttt tct aaa tta gcc agg gaa tat act gac cta gaa gta tcc cac      2688
Ser Phe Ser Lys Leu Ala Arg Glu Tyr Thr Asp Leu Glu Val Ser His
            885                 890                 895 aaa agt gaa att gct aat gcc ccg gat gga gct ggg tca ttg cct tgc      2736
Lys Ser Glu Ile Ala Asn Ala Pro Asp Gly Ala Gly Ser Leu Pro Cys
    900                 905                 910 aca gaa ttg ccc cat gac ctt tct ttg aag aac ata caa ccc aaa gtt      2784
Thr Glu Leu Pro His Asp Leu Ser Leu Lys Asn Ile Gln Pro Lys Val
                915                 920                 925 gaa gag aaa atc agt ttc tca gat gac ttt tct aaa aat ggg tct gct      2832
Glu Glu Lys Ile Ser Phe Ser Asp Asp Phe Ser Lys Asn Gly Ser Ala
            930                 935                 940 aca tca aag gtg ctc tta ttg cct cca gat gtt tct gct ttg gcc act      2880
Thr Ser Lys Val Leu Leu Leu Pro Pro Asp Val Ser Ala Leu Ala Thr
945                 950                 955                 960 caa gca gag ata gag agc ata gtt aaa ccc aaa gtt ctt gtg aaa gaa      2928
Gln Ala Glu Ile Glu Ser Ile Val Lys Pro Lys Val Leu Val Lys Glu
                965                 970                 975 gct gag aaa aaa ctt cct tcc gat aca gaa aaa gag gac aga tca cca      2976
Ala Glu Lys Lys Leu Pro Ser Asp Thr Glu Lys Glu Asp Arg Ser Pro
            980                 985                 990
```

| | | | | | | | | | | | | | | |
|---|---|---|---|---|---|---|---|---|---|---|---|---|---|---|
| tct | gct | ata | ttt | tca | gca | gag | ctg | agt | aaa | act | tca | gtt | gtt | gac ctc | 3024 |
| Ser | Ala | Ile | Phe | Ser | Ala | Glu | Leu | Ser | Lys | Thr | Ser | Val | Val | Asp Leu | |
| | 995 | | | | | 1000 | | | | | 1005 | | | | |

```
tct gct ata ttt tca gca gag ctg agt aaa act tca gtt gtt gac ctc   3024
Ser Ala Ile Phe Ser Ala Glu Leu Ser Lys Thr Ser Val Val Asp Leu
        995                 1000                1005 ctg tac tgg aga gac att aag aag act gga gtg gtg ttt ggt gcc       3069
Leu Tyr Trp Arg Asp Ile Lys Lys Thr Gly Val Val Phe Gly Ala
    1010                1015                1020 agc cta ttc ctg ctg ctt tca ttg aca gta ttc agc att gtg agc       3114
Ser Leu Phe Leu Leu Leu Ser Leu Thr Val Phe Ser Ile Val Ser
    1025                1030                1035 gta aca gcc tac att gcc ttg gcc ctg ctc tct gtg acc atc agc       3159
Val Thr Ala Tyr Ile Ala Leu Ala Leu Leu Ser Val Thr Ile Ser
    1040                1045                1050 ttt agg ata tac aag ggt gtg atc caa gct atc cag aaa tca gat       3204
Phe Arg Ile Tyr Lys Gly Val Ile Gln Ala Ile Gln Lys Ser Asp
    1055                1060                1065 gaa ggc cac cca ttc agg gca tat ctg gaa tct gaa gtt gct ata       3249
Glu Gly His Pro Phe Arg Ala Tyr Leu Glu Ser Glu Val Ala Ile
    1070                1075                1080 tct gag gag ttg gtt cag aag tac agt aat tct gct ctt ggt cat       3294
Ser Glu Glu Leu Val Gln Lys Tyr Ser Asn Ser Ala Leu Gly His
    1085                1090                1095 gtg aac tgc acg ata aag gaa ctc agg cgc ctc ttc tta gtt gat       3339
Val Asn Cys Thr Ile Lys Glu Leu Arg Arg Leu Phe Leu Val Asp
    1100                1105                1110 gat tta gtt gat tct ctg aag ttt gca gtg ttg atg tgg gta ttt       3384
Asp Leu Val Asp Ser Leu Lys Phe Ala Val Leu Met Trp Val Phe
    1115                1120                1125 acc tat gtt ggt gcc ttg ttt aat ggt ctg aca cta ctg att ttg       3429
Thr Tyr Val Gly Ala Leu Phe Asn Gly Leu Thr Leu Leu Ile Leu
    1130                1135                1140 gct ctc att tca ctc ttc agt gtt cct gtt att tat gaa cgg cat       3474
Ala Leu Ile Ser Leu Phe Ser Val Pro Val Ile Tyr Glu Arg His
    1145                1150                1155 cag gcg cag ata gat cat tat cta gga ctt gca aat aag aat gtt       3519
Gln Ala Gln Ile Asp His Tyr Leu Gly Leu Ala Asn Lys Asn Val
    1160                1165                1170 aaa gat gct atg gct aaa atc caa gca aaa atc cct gga ttg aag       3564
Lys Asp Ala Met Ala Lys Ile Gln Ala Lys Ile Pro Gly Leu Lys
    1175                1180                1185 cgc aaa gct gaa tga                                                3579
Arg Lys Ala Glu
    1190

<210> SEQ ID NO 23
<211> LENGTH: 1192
<212> TYPE: PRT
<213> ORGANISM: Homo sapiens

<400> SEQUENCE: 23

Met Glu Asp Leu Asp Gln Ser Pro Leu Val Ser Ser Asp Ser Pro
1               5                   10                  15

Pro Arg Pro Gln Pro Ala Phe Lys Tyr Gln Phe Val Arg Glu Pro Glu
                20                  25                  30

Asp Glu Glu Glu Glu Glu Glu Glu Glu Glu Asp Glu Asp Glu Asp
            35                  40                  45

Leu Glu Glu Leu Glu Val Leu Glu Arg Lys Pro Ala Ala Gly Leu Ser
        50                  55                  60

Ala Ala Pro Val Pro Thr Ala Pro Ala Ala Gly Ala Pro Leu Met Asp
65                  70                  75                  80
```

-continued

```
Phe Gly Asn Asp Phe Val Pro Ala Pro Arg Gly Pro Leu Pro Ala
                85                  90                  95
Ala Pro Pro Val Ala Pro Glu Arg Gln Pro Ser Trp Asp Pro Ser Pro
            100                 105                 110
Val Ser Ser Thr Val Pro Ala Pro Ser Pro Leu Ser Ala Ala Ala Val
            115                 120                 125
Ser Pro Ser Lys Leu Pro Glu Asp Asp Glu Pro Pro Ala Arg Pro Pro
130                 135                 140
Pro Pro Pro Pro Ala Ser Val Ser Pro Gln Ala Glu Pro Val Trp Thr
145                 150                 155                 160
Pro Pro Ala Pro Ala Pro Ala Ala Pro Ser Thr Pro Ala Ala Pro
            165                 170                 175
Lys Arg Arg Gly Ser Ser Gly Ser Val Asp Glu Thr Leu Phe Ala Leu
            180                 185                 190
Pro Ala Ala Ser Glu Pro Val Ile Arg Ser Ser Ala Glu Asn Met Asp
            195                 200                 205
Leu Lys Glu Gln Pro Gly Asn Thr Ile Ser Ala Gly Gln Glu Asp Phe
210                 215                 220
Pro Ser Val Leu Leu Glu Thr Ala Ala Ser Leu Pro Ser Leu Ser Pro
225                 230                 235                 240
Leu Ser Ala Ala Ser Phe Lys Glu His Glu Tyr Leu Gly Asn Leu Ser
            245                 250                 255
Thr Val Leu Pro Thr Glu Gly Thr Leu Gln Glu Asn Val Ser Glu Ala
            260                 265                 270
Ser Lys Glu Val Ser Glu Lys Ala Lys Thr Leu Leu Ile Asp Arg Asp
            275                 280                 285
Leu Thr Glu Phe Ser Glu Leu Glu Tyr Ser Glu Met Gly Ser Ser Phe
            290                 295                 300
Ser Val Ser Pro Lys Ala Glu Ser Ala Val Ile Val Ala Asn Pro Arg
305                 310                 315                 320
Glu Glu Ile Ile Val Lys Asn Lys Asp Glu Glu Lys Leu Val Ser
            325                 330                 335
Asn Asn Ile Leu His Asn Gln Gln Glu Leu Pro Thr Ala Leu Thr Lys
            340                 345                 350
Leu Val Lys Glu Asp Glu Val Val Ser Glu Lys Ala Lys Asp Ser
            355                 360                 365
Phe Asn Glu Lys Arg Val Ala Val Glu Ala Pro Met Arg Glu Glu Tyr
            370                 375                 380
Ala Asp Phe Lys Pro Phe Glu Arg Val Trp Glu Val Lys Asp Ser Lys
385                 390                 395                 400
Glu Asp Ser Asp Met Leu Ala Ala Gly Gly Lys Ile Glu Ser Asn Leu
            405                 410                 415
Glu Ser Lys Val Asp Lys Lys Cys Phe Ala Asp Ser Leu Glu Gln Thr
            420                 425                 430
Asn His Glu Lys Asp Ser Glu Ser Ser Asn Asp Thr Ser Phe Pro
            435                 440                 445
Ser Thr Pro Glu Gly Ile Lys Asp Arg Pro Gly Ala Tyr Ile Thr Cys
            450                 455                 460
Ala Pro Phe Asn Pro Ala Ala Thr Glu Ser Ile Ala Thr Asn Ile Phe
465                 470                 475                 480
Pro Leu Leu Gly Asp Pro Thr Ser Glu Asn Lys Thr Asp Glu Lys Lys
            485                 490                 495
```

-continued

```
Ile Glu Glu Lys Lys Ala Gln Ile Val Thr Glu Lys Asn Thr Ser Thr
            500                 505                 510

Lys Thr Ser Asn Pro Phe Leu Val Ala Ala Gln Asp Ser Glu Thr Asp
        515                 520                 525

Tyr Val Thr Thr Asp Asn Leu Thr Lys Val Thr Glu Glu Val Val Ala
        530                 535                 540

Asn Met Pro Glu Gly Leu Thr Pro Asp Leu Val Gln Glu Ala Cys Glu
545                 550                 555                 560

Ser Glu Leu Asn Glu Val Thr Gly Thr Lys Ile Ala Tyr Glu Thr Lys
                565                 570                 575

Met Asp Leu Val Gln Thr Ser Glu Val Met Gln Glu Ser Leu Tyr Pro
            580                 585                 590

Ala Ala Gln Leu Cys Pro Ser Phe Glu Glu Ser Glu Ala Thr Pro Ser
        595                 600                 605

Pro Val Leu Pro Asp Ile Val Met Glu Ala Pro Leu Asn Ser Ala Val
        610                 615                 620

Pro Ser Ala Gly Ala Ser Val Ile Gln Pro Ser Ser Pro Leu Glu
625                 630                 635                 640

Ala Ser Ser Val Asn Tyr Glu Ser Ile Lys His Glu Pro Glu Asn Pro
                645                 650                 655

Pro Pro Tyr Glu Glu Ala Met Ser Val Ser Leu Lys Lys Val Ser Gly
            660                 665                 670

Ile Lys Glu Glu Ile Lys Glu Pro Glu Asn Ile Asn Ala Ala Leu Gln
        675                 680                 685

Glu Thr Glu Ala Pro Tyr Ile Ser Ile Ala Cys Asp Leu Ile Lys Glu
        690                 695                 700

Thr Lys Leu Ser Ala Glu Pro Ala Pro Asp Phe Ser Asp Tyr Ser Glu
705                 710                 715                 720

Met Ala Lys Val Glu Gln Pro Val Pro Asp His Ser Glu Leu Val Glu
                725                 730                 735

Asp Ser Ser Pro Asp Ser Glu Pro Val Asp Leu Phe Ser Asp Asp Ser
            740                 745                 750

Ile Pro Asp Val Pro Gln Lys Gln Asp Glu Thr Val Met Leu Val Lys
        755                 760                 765

Glu Ser Leu Thr Glu Thr Ser Phe Glu Ser Met Ile Glu Tyr Glu Asn
        770                 775                 780

Lys Glu Lys Leu Ser Ala Leu Pro Pro Glu Gly Gly Lys Pro Tyr Leu
785                 790                 795                 800

Glu Ser Phe Lys Leu Ser Leu Asp Asn Thr Lys Asp Thr Leu Leu Pro
                805                 810                 815

Asp Glu Val Ser Thr Leu Ser Lys Lys Glu Lys Ile Pro Leu Gln Met
            820                 825                 830

Glu Glu Leu Ser Thr Ala Val Tyr Ser Asn Asp Asp Leu Phe Ile Ser
        835                 840                 845

Lys Glu Ala Gln Ile Arg Glu Thr Glu Thr Phe Ser Asp Ser Ser Pro
        850                 855                 860

Ile Glu Ile Ile Asp Glu Phe Pro Thr Leu Ile Ser Ser Lys Thr Asp
865                 870                 875                 880

Ser Phe Ser Lys Leu Ala Arg Glu Tyr Thr Asp Leu Glu Val Ser His
                885                 890                 895

Lys Ser Glu Ile Ala Asn Ala Pro Asp Gly Ala Gly Ser Leu Pro Cys
            900                 905                 910

Thr Glu Leu Pro His Asp Leu Ser Leu Lys Asn Ile Gln Pro Lys Val
```

```
                915                 920                 925
Glu Glu Lys Ile Ser Phe Ser Asp Asp Phe Ser Lys Asn Gly Ser Ala
    930                 935                 940

Thr Ser Lys Val Leu Leu Leu Pro Pro Asp Val Ser Ala Leu Ala Thr
945                 950                 955                 960

Gln Ala Glu Ile Glu Ser Ile Val Lys Pro Lys Val Leu Val Lys Glu
                965                 970                 975

Ala Glu Lys Lys Leu Pro Ser Asp Thr Glu Lys Glu Asp Arg Ser Pro
            980                 985                 990

Ser Ala Ile Phe Ser Ala Glu Leu Ser Lys Thr Ser Val Val Asp Leu
        995                 1000                1005

Leu Tyr Trp Arg Asp Ile Lys Lys Thr Gly Val Val Phe Gly Ala
    1010                1015                1020

Ser Leu Phe Leu Leu Leu Ser Leu Thr Val Phe Ser Ile Val Ser
    1025                1030                1035

Val Thr Ala Tyr Ile Ala Leu Ala Leu Leu Ser Val Thr Ile Ser
    1040                1045                1050

Phe Arg Ile Tyr Lys Gly Val Ile Gln Ala Ile Gln Lys Ser Asp
    1055                1060                1065

Glu Gly His Pro Phe Arg Ala Tyr Leu Glu Ser Glu Val Ala Ile
    1070                1075                1080

Ser Glu Glu Leu Val Gln Lys Tyr Ser Asn Ser Ala Leu Gly His
    1085                1090                1095

Val Asn Cys Thr Ile Lys Glu Leu Arg Arg Leu Phe Leu Val Asp
    1100                1105                1110

Asp Leu Val Asp Ser Leu Lys Phe Ala Val Leu Met Trp Val Phe
    1115                1120                1125

Thr Tyr Val Gly Ala Leu Phe Asn Gly Leu Thr Leu Leu Ile Leu
    1130                1135                1140

Ala Leu Ile Ser Leu Phe Ser Val Pro Val Ile Tyr Glu Arg His
    1145                1150                1155

Gln Ala Gln Ile Asp His Tyr Leu Gly Leu Ala Asn Lys Asn Val
    1160                1165                1170

Lys Asp Ala Met Ala Lys Ile Gln Ala Lys Ile Pro Gly Leu Lys
    1175                1180                1185

Arg Lys Ala Glu
    1190

<210> SEQ ID NO 24
<211> LENGTH: 373
<212> TYPE: PRT
<213> ORGANISM: Homo sapiens

<400> SEQUENCE: 24

Met Glu Asp Leu Asp Gln Ser Pro Leu Val Ser Ser Asp Ser Pro
1               5                   10                  15

Pro Arg Pro Gln Pro Ala Phe Lys Tyr Gln Phe Val Arg Glu Pro Glu
            20                  25                  30

Asp Glu Glu Glu Glu Glu Glu Glu Glu Glu Asp Glu Asp Glu Asp
        35                  40                  45

Leu Glu Glu Leu Glu Val Leu Glu Arg Lys Pro Ala Ala Gly Leu Ser
    50                  55                  60

Ala Ala Pro Val Pro Thr Ala Pro Ala Ala Gly Ala Pro Leu Met Asp
65                  70                  75                  80
```

-continued

Phe Gly Asn Asp Phe Val Pro Pro Ala Pro Arg Gly Pro Leu Pro Ala
                85                  90                  95

Ala Pro Pro Val Ala Pro Glu Arg Gln Pro Ser Trp Asp Pro Ser Pro
            100                 105                 110

Val Ser Ser Thr Val Pro Ala Pro Ser Pro Leu Ser Ala Ala Ala Val
            115                 120                 125

Ser Pro Ser Lys Leu Pro Glu Asp Asp Glu Pro Pro Ala Arg Pro Pro
        130                 135                 140

Pro Pro Pro Pro Ala Ser Val Ser Pro Gln Ala Glu Pro Val Trp Thr
145                 150                 155                 160

Pro Pro Ala Pro Ala Pro Ala Ala Pro Pro Ser Thr Pro Ala Ala Pro
                165                 170                 175

Lys Arg Arg Gly Ser Ser Gly Ser Val Val Asp Leu Leu Tyr Trp
                180                 185                 190

Arg Asp Ile Lys Lys Thr Gly Val Val Phe Gly Ala Ser Leu Phe Leu
            195                 200                 205

Leu Leu Ser Leu Thr Val Phe Ser Ile Val Ser Val Thr Ala Tyr Ile
        210                 215                 220

Ala Leu Ala Leu Leu Ser Val Thr Ile Ser Phe Arg Ile Tyr Lys Gly
225                 230                 235                 240

Val Ile Gln Ala Ile Gln Lys Ser Asp Glu Gly His Pro Phe Arg Ala
                245                 250                 255

Tyr Leu Glu Ser Glu Val Ala Ile Ser Glu Glu Leu Val Gln Lys Tyr
            260                 265                 270

Ser Asn Ser Ala Leu Gly His Val Asn Cys Thr Ile Lys Glu Leu Arg
        275                 280                 285

Arg Leu Phe Leu Val Asp Asp Leu Val Asp Ser Leu Lys Phe Ala Val
290                 295                 300

Leu Met Trp Val Phe Thr Tyr Val Gly Ala Leu Phe Asn Gly Leu Thr
305                 310                 315                 320

Leu Leu Ile Leu Ala Leu Ile Ser Leu Phe Ser Val Pro Val Ile Tyr
                325                 330                 335

Glu Arg His Gln Ala Gln Ile Asp His Tyr Leu Gly Leu Ala Asn Lys
            340                 345                 350

Asn Val Lys Asp Ala Met Ala Lys Ile Gln Ala Lys Ile Pro Gly Leu
        355                 360                 365

Lys Arg Lys Ala Glu
        370

<210> SEQ ID NO 25
<211> LENGTH: 199
<212> TYPE: PRT
<213> ORGANISM: Homo sapiens

<400> SEQUENCE: 25

Met Asp Gly Gln Lys Lys Asn Trp Lys Asp Lys Val Val Asp Leu Leu
1               5                   10                  15

Tyr Trp Arg Asp Ile Lys Lys Thr Gly Val Val Phe Gly Ala Ser Leu
            20                  25                  30

Phe Leu Leu Leu Ser Leu Thr Val Phe Ser Ile Val Ser Val Thr Ala
        35                  40                  45

Tyr Ile Ala Leu Ala Leu Leu Ser Val Thr Ile Ser Phe Arg Ile Tyr
    50                  55                  60

Lys Gly Val Ile Gln Ala Ile Gln Lys Ser Asp Glu Gly His Pro Phe
65                  70                  75                  80

```
Arg Ala Tyr Leu Glu Ser Glu Val Ala Ile Ser Glu Glu Leu Val Gln
                85                  90                  95

Lys Tyr Ser Asn Ser Ala Leu Gly His Val Asn Cys Thr Ile Lys Glu
            100                 105                 110

Leu Arg Arg Leu Phe Leu Val Asp Asp Leu Val Asp Ser Leu Lys Phe
        115                 120                 125

Ala Val Leu Met Trp Val Phe Thr Tyr Val Gly Ala Leu Phe Asn Gly
    130                 135                 140

Leu Thr Leu Leu Ile Leu Ala Leu Ile Ser Leu Phe Ser Val Pro Val
145                 150                 155                 160

Ile Tyr Glu Arg His Gln Ala Gln Ile Asp His Tyr Leu Gly Leu Ala
                165                 170                 175

Asn Lys Asn Val Lys Asp Ala Met Ala Lys Ile Gln Ala Lys Ile Pro
            180                 185                 190

Gly Leu Lys Arg Lys Ala Glu
        195

<210> SEQ ID NO 26
<211> LENGTH: 473
<212> TYPE: PRT
<213> ORGANISM: Homo sapiens

<400> SEQUENCE: 26

Met Lys Arg Ala Ser Ala Gly Gly Ser Arg Leu Leu Ala Trp Val Leu
1               5                   10                  15

Trp Leu Gln Ala Trp Gln Val Ala Ala Pro Cys Pro Gly Ala Cys Val
            20                  25                  30

Cys Tyr Asn Glu Pro Lys Val Thr Thr Ser Cys Pro Gln Gln Gly Leu
        35                  40                  45

Gln Ala Val Pro Val Gly Ile Pro Ala Ala Ser Gln Arg Ile Phe Leu
    50                  55                  60

His Gly Asn Arg Ile Ser His Val Pro Ala Ala Ser Phe Arg Ala Cys
65                  70                  75                  80

Arg Asn Leu Thr Ile Leu Trp Leu His Ser Asn Val Leu Ala Arg Ile
                85                  90                  95

Asp Ala Ala Ala Phe Thr Gly Leu Ala Leu Leu Glu Gln Leu Asp Leu
            100                 105                 110

Ser Asp Asn Ala Gln Leu Arg Ser Val Asp Pro Ala Thr Phe His Gly
        115                 120                 125

Leu Gly Arg Leu His Thr Leu His Leu Asp Arg Cys Gly Leu Gln Glu
    130                 135                 140

Leu Gly Pro Gly Leu Phe Arg Gly Leu Ala Ala Leu Gln Tyr Leu Tyr
145                 150                 155                 160

Leu Gln Asp Asn Ala Leu Gln Ala Leu Pro Asp Asp Thr Phe Arg Asp
                165                 170                 175

Leu Gly Asn Leu Thr His Leu Phe Leu His Gly Asn Arg Ile Ser Ser
            180                 185                 190

Val Pro Glu Arg Ala Phe Arg Gly Leu His Ser Leu Asp Arg Leu Leu
        195                 200                 205

Leu His Gln Asn Arg Val Ala His Val His Pro His Ala Phe Arg Asp
    210                 215                 220

Leu Gly Arg Leu Met Thr Leu Tyr Leu Phe Ala Asn Asn Leu Ser Ala
225                 230                 235                 240

Leu Pro Thr Glu Ala Leu Ala Pro Leu Arg Ala Leu Gln Tyr Leu Arg
```

-continued

```
                245                 250                 255
Leu Asn Asp Asn Pro Trp Val Cys Asp Cys Arg Ala Arg Pro Leu Trp
                260                 265                 270

Ala Trp Leu Gln Lys Phe Arg Gly Ser Ser Glu Val Pro Cys Ser
            275                 280                 285

Leu Pro Gln Arg Leu Ala Gly Arg Asp Leu Lys Arg Leu Ala Ala Asn
        290                 295                 300

Asp Leu Gln Gly Cys Ala Val Ala Thr Gly Pro Tyr His Pro Ile Trp
305                 310                 315                 320

Thr Gly Arg Ala Thr Asp Glu Glu Pro Leu Gly Leu Pro Lys Cys Cys
                325                 330                 335

Gln Pro Asp Ala Ala Asp Lys Ala Ser Val Leu Glu Pro Gly Arg Pro
            340                 345                 350

Ala Ser Ala Gly Asn Ala Leu Lys Gly Arg Val Pro Pro Gly Asp Ser
        355                 360                 365

Pro Pro Gly Asn Gly Ser Gly Pro Arg His Ile Asn Asp Ser Pro Phe
    370                 375                 380

Gly Thr Leu Pro Gly Ser Ala Glu Pro Pro Leu Thr Ala Val Arg Pro
385                 390                 395                 400

Glu Gly Ser Glu Pro Pro Gly Phe Pro Thr Ser Gly Pro Arg Arg Arg
                405                 410                 415

Pro Gly Cys Ser Arg Lys Asn Arg Thr Arg Ser His Cys Arg Leu Gly
            420                 425                 430

Gln Ala Gly Ser Gly Gly Gly Thr Gly Asp Ser Glu Gly Ser Gly
        435                 440                 445

Ala Leu Pro Ser Leu Thr Cys Ser Leu Thr Pro Leu Gly Leu Ala Leu
    450                 455                 460

Val Leu Trp Thr Val Leu Gly Pro Cys
465                 470

<210> SEQ ID NO 27
<211> LENGTH: 473
<212> TYPE: PRT
<213> ORGANISM: Mus musculus

<400> SEQUENCE: 27

Met Lys Arg Ala Ser Ser Gly Gly Ser Arg Leu Leu Ala Trp Val Leu
1               5                   10                  15

Trp Leu Gln Ala Trp Arg Val Ala Thr Pro Cys Pro Gly Ala Cys Val
            20                  25                  30

Cys Tyr Asn Glu Pro Lys Val Thr Thr Ser Cys Pro Gln Gln Gly Leu
        35                  40                  45

Gln Ala Val Pro Thr Gly Ile Pro Ala Ser Ser Gln Arg Ile Phe Leu
    50                  55                  60

His Gly Asn Arg Ile Ser His Val Pro Ala Ala Ser Phe Gln Ser Cys
65                  70                  75                  80

Arg Asn Leu Thr Ile Leu Trp Leu His Ser Asn Ala Leu Ala Arg Ile
                85                  90                  95

Asp Ala Ala Ala Phe Thr Gly Leu Thr Leu Leu Glu Gln Leu Asp Leu
            100                 105                 110

Ser Asp Asn Ala Gln Leu His Val Val Asp Pro Thr Thr Phe His Gly
        115                 120                 125

Leu Gly His Leu His Thr Leu His Leu Asp Arg Cys Gly Leu Arg Glu
    130                 135                 140
```

Leu Gly Pro Gly Leu Phe Arg Gly Leu Ala Ala Leu Gln Tyr Leu Tyr
145                 150                 155                 160

Leu Gln Asp Asn Asn Leu Gln Ala Leu Pro Asp Asn Thr Phe Arg Asp
            165                 170                 175

Leu Gly Asn Leu Thr His Leu Phe Leu His Gly Asn Arg Ile Pro Ser
        180                 185                 190

Val Pro Glu His Ala Phe Arg Gly Leu His Ser Leu Asp Arg Leu Leu
        195                 200                 205

Leu His Gln Asn His Val Ala Arg Val His Pro His Ala Phe Arg Asp
    210                 215                 220

Leu Gly Arg Leu Met Thr Leu Tyr Leu Phe Ala Asn Asn Leu Ser Met
225                 230                 235                 240

Leu Pro Ala Glu Val Leu Met Pro Leu Arg Ser Leu Gln Tyr Leu Arg
                245                 250                 255

Leu Asn Asp Asn Pro Trp Val Cys Asp Cys Arg Ala Arg Pro Leu Trp
            260                 265                 270

Ala Trp Leu Gln Lys Phe Arg Gly Ser Ser Ser Glu Val Pro Cys Asn
        275                 280                 285

Leu Pro Gln Arg Leu Ala Asp Arg Asp Leu Lys Arg Leu Ala Ala Ser
    290                 295                 300

Asp Leu Glu Gly Cys Ala Val Ala Ser Gly Pro Phe Arg Pro Ile Gln
305                 310                 315                 320

Thr Ser Gln Leu Thr Asp Glu Glu Leu Leu Ser Leu Pro Lys Cys Cys
                325                 330                 335

Gln Pro Asp Ala Ala Asp Lys Ala Ser Val Leu Glu Pro Gly Arg Pro
            340                 345                 350

Ala Ser Ala Gly Asn Ala Leu Lys Gly Arg Val Pro Pro Gly Asp Thr
        355                 360                 365

Pro Pro Gly Asn Gly Ser Gly Pro Arg His Ile Asn Asp Ser Pro Phe
    370                 375                 380

Gly Thr Leu Pro Ser Ser Ala Glu Pro Pro Leu Thr Ala Leu Arg Pro
385                 390                 395                 400

Gly Gly Ser Glu Pro Pro Gly Leu Pro Thr Thr Gly Pro Arg Arg Arg
                405                 410                 415

Pro Gly Cys Ser Arg Lys Asn Arg Thr Arg Ser His Cys Arg Leu Gly
            420                 425                 430

Gln Ala Gly Ser Gly Ala Ser Gly Thr Gly Asp Ala Glu Gly Ser Gly
        435                 440                 445

Ala Leu Pro Ala Leu Ala Cys Ser Leu Ala Pro Leu Gly Leu Ala Leu
    450                 455                 460

Val Leu Trp Thr Val Leu Gly Pro Cys
465                 470

<210> SEQ ID NO 28
<211> LENGTH: 15
<212> TYPE: PRT
<213> ORGANISM: Artificial Sequence
<220> FEATURE:
<223> OTHER INFORMATION: synthetic

<400> SEQUENCE: 28

Ser Gly Val Pro Ser Asn Leu Pro Gln Arg Leu Ala Gly Arg Asp
1               5                   10                  15

<210> SEQ ID NO 29
<211> LENGTH: 15

```
-continued

<212> TYPE: PRT
<213> ORGANISM: Artificial Sequence
<220> FEATURE:
<223> OTHER INFORMATION: synthetic

<400> SEQUENCE: 29

Thr Arg Ser His Cys Arg Leu Gly Gln Ala Gly Ser Gly Ser Ser
1               5                   10                  15
```

METHOD FOR REDUCING NEURONAL DEGENERATION SO AS TO AMELIORATE THE EFFECTS OF INJURY OR DISEASE

CROSS-REFERENCE TO RELATED APPLICATIONS

The present application is a continuation of application Ser. No. 09/893,348 filed Jun. 28, 2001, now abandoned, itself a continuation-in-part of application Ser. No. 09/314,161, filed May 19, 1999, which is a continuation-in-part of application No. PCT/US98/14715, filed Jul. 21, 1998, and is a continuation-in-part of application Ser. No. 09/218,277, filed Dec. 22, 1998, now abandoned, the entire contents of each of which are hereby incorporated herein by reference.

FIELD OF THE INVENTION

The present invention relates to compositions and methods for the promotion of nerve regeneration or prevention or inhibition of neuronal degeneration to ameliorate the effects of injury or disease of the nervous system (NS). In the certain embodiments, activated T cells, an NS-specific antigen or peptide derived therefrom or a nucleotide sequence encoding an NS-specific antigen can be used to promote nerve regeneration or to confer neuroprotection and prevent or inhibit neuronal degeneration caused by injury or disease of nerves within the central nervous system or peripheral nervous system of a human subject. The compositions of the present invention may be administered alone or may be optionally administered in any desired combination.

Abbreviations: APC: antigen-presenting cell; BSA: bovine serum albumin; CAP: compound action potential; CFA: complete Freund's adjuvant; CNS: central nervous system; 4-Di-10-Asp: 4-(4-didecylamino)styryl)-N-methylpyridinium iodide; EAE: experimental autoimmune encephalomyelitis; FCS: fetal calf serum; IFA: incomplete Freund's adjuvant MAG: myelin-associated glycoprotein; MBP: myelin basic protein; MOG: myelin oligodendrocyte glycoprotein; NS: nervous system; OVA: ovalbumin; PBS: phosphate-buffered saline; PLP: proteolipid protein; PNS: peripheral nervous system; RGC: retinal ganglion cells; TCR: T-cell receptor.

BACKGROUND OF THE INVENTION

The nervous system comprises the central (CNS) and the peripheral (PNS) nervous system. The CNS is composed of the brain, the spinal cord and the visual system; the PNS consists of all of the other neural elements, namely the nerves and ganglia outside of the brain and spinal cord.

Damage to the nervous system may result from a traumatic injury, such as penetrating trauma or blunt trauma, or a disease or disorder including, but not limited to Alzheimer's disease, Parkinson's disease, multiple sclerosis, Huntington's disease, amyotrophic lateral sclerosis (ALS), diabetic neuropathy, senile dementia, stroke and ischemia.

Maintenance of CNS integrity is a complex balancing act in which compromises are struck with the immune system. In most tissues, the immune system plays an essential part in protection, repair, and healing. In the CNS, because of its unique immune privilege, immunological reactions are relatively limited (Streilein, 1993). A growing body of evidence indicates that the failure of the mammalian CNS to achieve functional recovery after injury is a reflection of an ineffective dialog between the damaged tissue and the immune system. For example, the restricted communication between the CNS and blood-borne macrophages affects the capacity of axotomized axons to regrow; transplants of activated macrophages can promote CNS regrowth (Lazarov-Spiegler et al, 1996; Rapalino et al, 1998).

Activated T cells have been shown to enter the CNS parenchyma, irrespective of their antigen specificity, but only T cells capable of reacting with a CNS antigen seem to persist there (Hickey et al, 1991; Werkele, 1993; Kramer et al, 1995). T cells reactive to antigens of CNS white matter, such as myelin basic protein (MBP), can induce the paralytic disease experimental autoimmune encephalomyelitis (EAE) within several days of their inoculation into naive recipient rats (Ben-Nun et al, 1981a). Anti-MPB T cells may also be involved in the human disease multiple sclerosis (Ota et al, 1990; Martin, 1997). However, despite their pathogenic potential, anti-MBP T cell clones are present in the immune systems of healthy subjects (Burns et al, 1983; Pette et al, 1990; Martin et al, 1990; Schluesener et al, 1985). Activated T cells, which normally patrol the intact CNS, transiently accumulate at sites of CNS white matter lesions (Hirschberg et al, 1998).

A catastrophic consequence of CNS injury is that the primary damage is often compounded by the gradual secondary loss of adjacent neurons that apparently were undamaged, or only marginally damaged, by the initial injury (Faden et al, 1992; Faden, 1993; McIntosh, 1993). The primary lesion causes changes in extracellular ion concentrations, elevation of amounts of free radicals, release of neurotransmitters, depletion of growth factors, and local inflammation. These changes trigger a cascade of destructive events in the adjacent neurons that initially escaped the primary injury (Lynch et al, 1994; Bazan et al, 1995; Wu et al, 1994). This secondary damage is mediated by activation of voltage-dependent or agonist-gated channels, ion leaks, activation of calcium-dependent enzymes such as proteases, lipases and nucleases, mitochondrial dysfunction and energy depletion, culminating in neuronal cell death (Yoshina et al, 1991; Hovda et al, 1991; Zivin et al, 1991; Yoles et al, 1992). The widespread loss of neurons beyond the loss caused directly by the primary injury has been called "secondary degeneration."

Another tragic consequence of CNS injury is that neurons in the mammalian CNS do not undergo spontaneous regeneration following an injury. Thus, a CNS injury causes permanent impairment of motor and sensory functions.

Spinal cord lesions, regardless of the severity of the injury, initially result in a complete functional paralysis known as spinal shock. Some spontaneous recovery from spinal shock may be observed, starting a few days after the injury and tapering off within three to four weeks. The less severe the insult, the better the functional outcome. The extent of recovery is a function of the amount of undamaged tissue minus the loss due to secondary degeneration. Recovery from injury would be improved by neuroprotective treatment that could reduce secondary degeneration.

The parent applications, application nos. 09/218,277 and 09/314,161 and PCT Publication WO 99/60021, describe the discovery made in the laboratory of the present inventors that activated T cells that recognize an antigen of the NS of the patient confer neuroprotection. More specifically, T cells reactive to MBP were shown to be neuroprotective in rat models of partially crushed optic nerve (see also Moalem et al, 1999a, the entire contents of which being hereby incorporated herein by reference) and of spinal cord injury (see also Hauben et al, 2000, the entire contents of which being hereby incorporated herein by reference). Until recently, it had been thought that immune cells do not participate in NS repair. Furthermore, any immune activity in the context of CNS damage was traditionally considered detrimental for recovery. It was quite surprising to discover that NS-specific activated T cells could be used to protect nervous system tissue from secondary degeneration which may follow damage caused by injury or disease of the CNS or PNS. The mechanism of action of such NS-specific T cells has yet to be discovered, but the massive accumulation of exogenously administered T cells at the site of CNS injury suggests that the presence of T cells at the site of injury plays a prominent role in neuroprotection. It appears, however, that the accumulation, though a necessary condition, is not sufficient for the purpose, as T cells specific to the non-self antigen ovalbumin also accumulate at the site, but have no neuroprotective effect (Hirschberg et al, 1998).

In addition to the NS-specific activated T cells, the above-referenced U.S. applications and PCT publication WO 99/60021 disclose that therapy for amelioration of effects of injury or disease of NS can be carried out also with a natural or synthetic NS-specific antigen such as MAG, S-100, β-amyloid, Thy-1, P0, P2, a neurotransmitter receptor, and preferably human MBP, human proteolipid protein (PLP), and human oligodendrocyte glycoprotein (MOG), or with a peptide derived from an NS-specific antigen such as a peptide comprising amino acids 51-70 of MBP or amino acids 35-55 of MOG.

Citation or identification of any reference in this section or any other part of this application shall not be construed as an admission that such reference is available as prior art to the invention.

SUMMARY OF THE INVENTION

The present invention is directed to methods and compositions for promotion of nerve regeneration or for neuroprotection and prevention or inhibition of neuronal degeneration to ameliorate the effects of injury to, or disease of, the nervous system (NS).

The present invention is based in part on the inventors' unexpected discovery that activated T cells that recognize an antigen of the NS of the patient promote nerve regeneration or confer neuroprotection. As used herein, "neuroprotection" refers to the prevention or inhibition of degenerative effects of injury or disease in the NS. Since it was thought until recently that immune cells do not participate in nervous system repair, it was quite surprising to discover that NS-specific activated T cells and also the NS-specific antigens themselves and peptides derived therefrom can be used to promote nerve regeneration or to protect nervous system tissue from secondary degeneration which may follow damage caused by injury or disease of the CNS or PNS.

Thus, in one aspect, the invention relates to a method for promoting nerve regeneration or for conferring neuroprotection and preventing or inhibiting neuronal degeneration in the central nervous system or peripheral nervous system for ameliorating the effects of injury or disease, comprising administering to an individual in need thereof at least one ingredient selected from the group consisting of:
 (a) NS-specific activated T cells;
 (b) a NS-specific antigen or an analog thereof;
 (c) a peptide derived from an NS-specific antigen or from an analog thereof, or an analog or derivative of said peptide;
 (d) a nucleotide sequence encoding an NS-specific antigen or an analog thereof;
 (e) a nucleotide sequence encoding a peptide derived from an NS-specific antigen or from an analog thereof, or an analog of said peptide; or
 (f) any combination of (a)-(e).

In another aspect, the invention relates to a pharmaceutical composition for promoting nerve regeneration or for neuroprotection and prevention or inhibition of neuronal degeneration in the CNS or PNS for ameliorating the effects of injury or disease in the NS, comprising a therapeutically effective amount of at least one ingredient selected from the group consisting of (a) to (e) above or any combination of (a)-(e).

The term "NS-specific antigen" as used herein refers to an antigen of the NS that specifically activates T cells such that following activation the activated T cells accumulate at a site of injury or disease in the NS of the patient. Examples of NS-specific antigens according to the invention include, but are not limited to, myelin basic protein (MBP), myelin oligodendrocyte glycoprotein (MOG), proteolipid protein (PLP), myelin-associated glycoprotein (MAG), S-100, β-amyloid, Thy-1, P0, P2, neurotransmitter receptors, the protein Nogo (Nogo-A, Nogo-B and Nogo-C) and the Nogo receptor (NgR). This definition also includes analogs of said NS-specific antigens as described in the section on NS-specific antigens, analogs thereof, peptides derived therefrom and analogs and derivatives thereof of said peptides hereinafter.

BRIEF DESCRIPTION OF THE FIGURES

FIGS. 3 (A-C) present photomicrographs of retrogradely labeled retinas of injured optic nerves of rats. Immediately after unilateral crush injury of their optic nerves, rats were injected with PBS (FIG. 3A) or with activated anti-p277 T cells (FIG. 3B) or activated anti-MBP T cells (FIG. 3C). Two weeks later, the neurotracer dye 4-Di-10-Asp was applied to the optic nerves, distal to the site of injury. After 5 days, the retinas were excised and flat-mounted. Labeled (surviving) RGCs, located at approximately the same distance from the optic disk in each retina, were photographed.

FIGS. 7(A-B) are graphs showing recovery of voluntary motor activity as a function of time after contusion, with and without injection of autoimmune anti-MBP T cells.

FIGS. 12(A-F) show expression of B7 co-stimulatory molecules in intact and injured rat optic nerve. Optic nerves were excised from adult Lewis rats before (12A, 12B) and three days after injury (12C, 12D, 12E) and analyzed immunohistochemically for expression of the B7 co-stimulatory molecule. The site of injury was delineated by GFAP staining. Using calibrated cross-action forceps, the right optic nerve was subjected to a mild crush injury 1-2 mm from the eye. The uninjured cointralateral nerve was left undisturbed. Immunohistochemical analysis of optic nerve antigens was performed as follows. Briefly, longitudinal cryosections of the excised nerves (20 μm thick) were picked up onto gelatin-coated glass and fixed with ethanol for ten minutes at room temperature. The sections were washed and incubated for one hour at room temperature with mouse monoclonal antibody to rat GFAP (BioMakor, Israel), diluted 1:100, and with antibodies to B7.2 co-stimulatory molecule and the B7.1 co-stimulatory molecule (Pharmingen, San Diego, Calif.), diluted 1:25. The sections were washed again and incubated with rhodamine isothiocyanate-conjugated goat anti-mouse IgG (with minimal cross-reaction to rat, human, bovine and horse serum protein) (Jackson ImmunoResearch, West Grove, Pa.), for one hour at room temperature. All washing solutions contained PBS and 0.05% Tween-20. All diluting solutions contained PBS containing 3% fetal calf serum and 2% bovine serum albumin. The sections were treated with glycerol containing 1,4-diazobicyclo-(2,2,2)-octane and were then viewed with a Zeiss microscope. Note the morphological changes of the B7.2 positive cells after injury, from a rounded (12A, 12B) to a star-like shape (12C, 12D). The B7.2 positive cells were present at a higher density closer to the injury site (12E). Expression of B7.1 was detectable only from day seven and only at the injured site (12F).

FIGS. 13A-C show immunohistochemical analysis of T cells, macrophages or microglia, and B7.2 co-stimulatory molecules in the injured optic nerves of rats fed MBP. Lewis rats aged 6-8 weeks were fed 1 mg of bovine MBP (Sigma, Israel) (2 mg MBP/ml PBS) or 0.5 ml PBS only every other day by gastric intubation using a stainless steel feeding needle (Thomas Scientific, Swedesboro, N.J.) (Chen et al, 1994). Ten days after starting MBP, the right optic nerves were subjected to calibrated crush injury, as described for FIG. 12. Three days later, the nerves were excised and prepared for immunohistochemical analysis of T cells using mouse monoclonal antibodies to T cell receptor 11, diluted 1:25, macrophages or microglia using anti-ED1 antibodies (Serotek, Oxford, U.K) diluted 1:250, astrocytes using anti-GFAP antibodies and B7.2 co-stimulatory molecules as described for FIG. 12. There were no significant quantitative differences in T cells or in ED-1 positive cells between injured optic nerves of PBS-fed (13A) and MBP-fed (13B) rats. The number of B7.2 positive cells at the site of injury of MBP-fed rats (13C) should be noted, as compared with injured controls (see FIG. 12E above).

FIG. 15 shows the nucleotide sequence of rat MBP gene, SEQ ID NO:1, Genbank accession number M25889 (Schaich et al, 1986).

FIG. 16 shows the nucleotide sequence of human MBP gene, SEQ ID NO:2, Genbank accession number M13577 (Kamholz et al, 1986).

FIGS. 17(A-F) show the nucleotide sequences of human PLP gene exons 1-7, SEQ ID NOs:3-8, respectively, Genbank accession numbers M15026-M15032, respectively (Diehl et al, 1986).

FIG. 18(A-B) shows the nucleotide sequence of human MOG gene, SEQ ID NO:9, Genbank accession number Z48051 (Roth et al, submitted (17-Jan-1995) Roth, CNRS UPR 8291, CIGH, CHU Purpan, Toulouse, France, 31300; Gonzalez et al, 1996).

FIG. 19 shows the nucleotide sequence of rat PLP gene and variant, SEQ ID NO:10, Genbank accession number M16471 (Nave et al, 1987).

FIG. 20 shows the nucleotide sequence of rat MAG gene, SEQ ID NO:11, Genbank accession number M14871 (Arquint et al, 1987).

FIG. 21 shows the amino acid sequence of human MBP, SEQ ID NO:12, Genbank accession number 307160 (Kamholz et al, 1986).

FIG. 22 shows the amino acid sequence of human PLP, SEQ ID NO:13, Genbank accession number 387028.

FIG. 23 shows the amino acid sequence of human MOG, SEQ ID NO:14, Genbank accession number 793839 (Roth et al, 1995; Roth Submitted (17-JAN-1995) Roth CNRS UPR 8291, CIGH, CHU Purpan, Toulouse, France, 31300; Gonzalez et al, 1996).

DETAILED DESCRIPTION OF THE INVENTION

Figure 1:
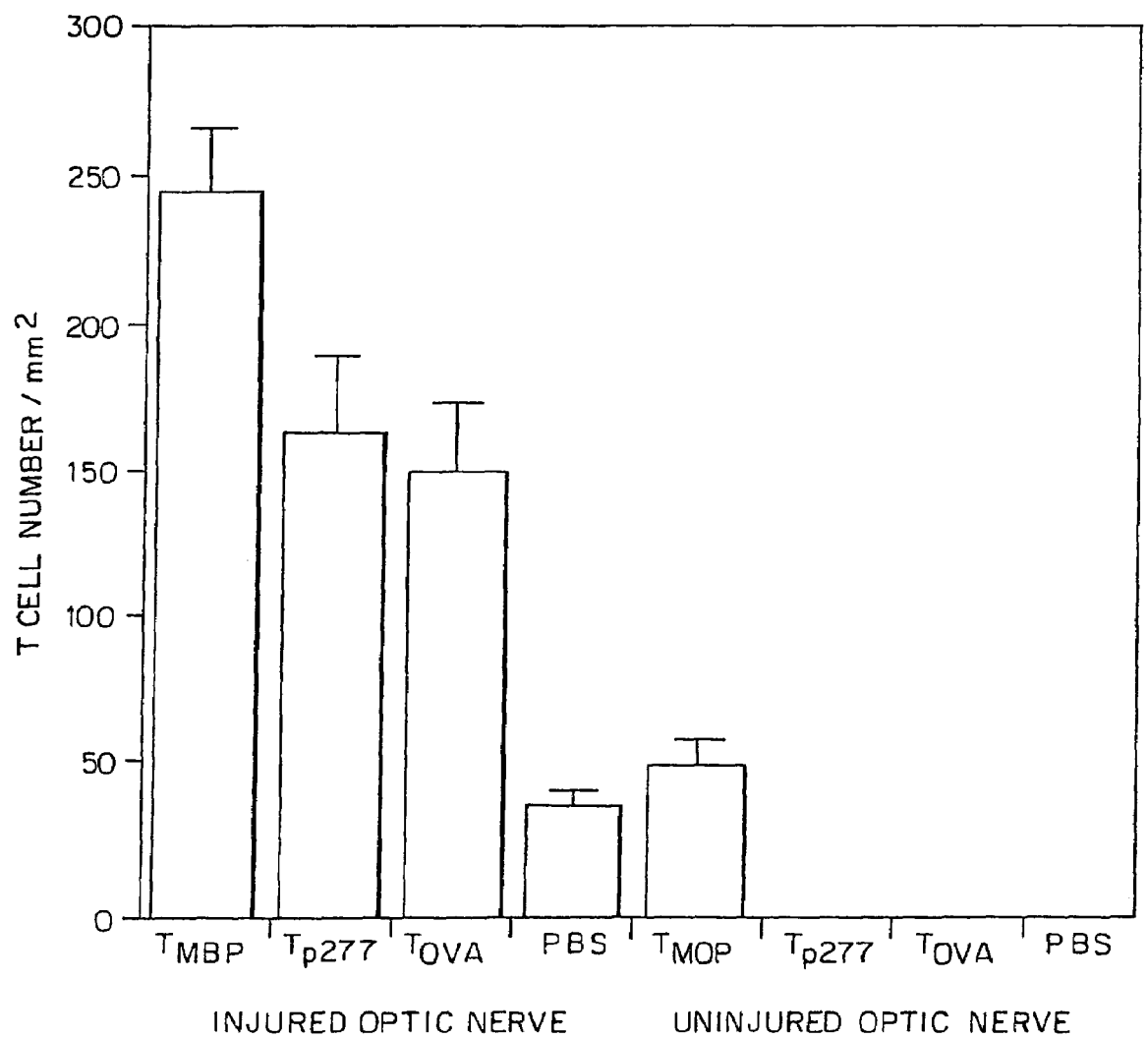
FIG. 1 is a bar graph showing the presence of T cells in uninjured optic nerve or in injured optic nerve one week after injury. Adult Lewis rats were injected with activated T cells of the anti-MBP ($T_{MBP}$), anti-OVA ($T_{OVA}$), anti-p277 (a peptide of the human hsp60) ($Tp_{277}$) lines, or with PBS, immediately after unilateral crush injury of the optic nerve. Seven days later, both the injured and uninjured optic nerves were removed, cryosectioned and analyzed immunohistochemically for the presence of immunolabeled T cells. T cells were counted at the site of injury and at randomly selected areas in the uninjured optic nerves. The histogram shows the mean number of T cells per $mm^2 \pm s.e.m.$, counted in two to three sections of each nerve. Each group contained three to four rats. The number of T cells was considerably higher in injured nerves of rats injected with anti-MBP, anti-OVA or anti-p277 T cells; statistical analysis (one-way ANOVA) showed significant differences between T cell numbers in injured optic nerves of rats injected with anti-MBP, anti-OVA, or anti-p277 T cells and the T cell numbers in injured optic nerves of rats injected with PBS ($P<0.001$); and between injured optic nerves and uninjured optic nerves of rats injected with anti-MBP, anti-OVA, or anti-p277 T cells ($P<0.001$).

As exposed above, the present invention relates to compositions and methods for promoting nerve regeneration or for conferring neuroprotection and preventing or inhibiting neuronal degeneration in the CNS or PNS for ameliorating the effects of injury or disease, comprising administering to an individual in need thereof at least one ingredient selected from the group consisting of:

(a) NS-specific activated T cells;
(b) a NS-specific antigen or an analog thereof;
(c) a peptide derived from an NS-specific antigen or from an analog thereof, or an analog or derivative of said peptide;
(d) a nucleotide sequence encoding an NS-specific antigen or an analog thereof;
(e) a nucleotide sequence encoding a peptide derived from an NS-specific antigen or from an analog thereof, or an analog of said peptide; or
(f) any combination of (a)-(e).

Merely for ease of explanation, the detailed description of the present invention is divided into the following sections: NS-specific activated T cells and T-cell banks; NS-specific antigens, analogs thereof, peptides derived therefrom and analogs and derivatives thereof of said peptides; nucleotide sequences encoding NS-specific antigens, analogs thereof, peptides derived therefrom and analogs thereof; therapeutic uses; and formulations and modes of administration.

NS-Specific Activated T Cells and T-Cell Banks

In one embodiment of the invention, NS-specific activated T cells can be used in an amount which is effective to confer neuroprotection for ameliorating or inhibiting the effects of injury or disease of the CNS or PNS that result in NS degeneration or for promoting regeneration in the NS, in particular the CNS, as described in the section on therapeutic uses hereinafter.

In the practice of the invention, administration of NS-specific activated T cells may optionally be in combination with an NS-specific antigen or an analog thereof or a peptide derived therefrom or an analog or derivative of said peptide. Additionally, oral administration of NS-specific antigen or an analog thereof or a peptide derived therefrom or an analog or derivative thereof, can be combined with active immunization to build up a critical T-cell response immediately after injury.

Activation of T cells is initiated by interaction of a TCR complex with a processed antigenic peptide bound to a MHC molecule on the surface of an antigen-presenting cell (APC). As used herein, the term "activated T cells" includes both (i) T cells that have been activated by exposure to a cognate antigen or peptide derived therefrom or derivative thereof; and (ii) progeny of such activated T cells. As used herein, a "cognate antigen" is an antigen that is specifically recognized by the TCR of a T cell that has been previously exposed to the antigen. Alternatively, the T cell which has been previously exposed to the antigen may be activated by a mitogen, such as phytohemagglutinin (PHA) or concanavalin A (Con A).

The term "NS-specific activated T cell" as used herein refers to an activated T cell having specificity for an antigen of the NS, said NS-specific antigen being an antigen of the NS that specifically activates T cells such that these activated T cells will accumulate at a site of injury or disease in the NS of the patient. The NS-specific antigen used to confer the specificity to the T cells may be a self NS-antigen of the patient or a non-self NS-antigen of another individual or even of another species, or an analog of said NS-antigen, or a peptide derived from said NS-antigen or from said analog thereof, or an analog or derivative of said peptide, all as described in the section on NS-specific antigens, analogs thereof, peptides derived therefrom and analogs and derivatives thereof of said peptides hereinafter, as long as the activated T cell recognizes an antigen in the NS of the patient.

If the disease being treated by the NS-specific activated T cells of the invention is an autoimmune disease, in which the autoimmune antigen is an NS antigen, the T cells which are used in accordance with the present invention for the treatment of neural damage or degeneration caused by such disease are preferably not activated against the same autoimmune antigen involved in the disease. While the prior art has described methods of treating autoimmune diseases by administering activated T cells to create a tolerance to the autoimmune antigen, the T cells of the present invention are not administered in such a way as to create tolerance, but are administered in such a way as to create accumulation of the T cells at the site of injury or disease so as to facilitate neural regeneration or to inhibit neural degeneration.

The prior art also discloses uses of immunotherapy against tumors, including brain tumors, by administering T cells specific to an NS antigen in the tumor so that such T cells may induce an immune system attack against the tumors. The present invention is not intended to comprehend such prior art techniques. However, the present invention is intended to comprehend the inhibition of neural degeneration or the enhancement of neural regeneration in patients with brain tumors by means other than the prior art immunotherapy of brain tumors. Thus, for example, NS-specific activated T cells, which are activated to an NS-antigen of the patient other than an antigen which is involved in the tumor, would be expected to be useful for the purpose of the present invention and would not have been suggested by known immunotherapy techniques.

The NS-specific activated T cells are preferably autologous, most preferably of the CD4 and/or CD8 phenotypes, but they may also be semi-allogeneic T cells or allogeneic T cells from related donors, e.g., siblings, parents, children, or from donors with the same HLA type (HLA-matched) or a very similar HLA type (HLA-partially matched), or even from unrelated donors.

Thus, in addition to the use of autologous T cells isolated from the subject, the present invention also comprehends the use of semi-allogeneic T cells for neuroprotection. The T cells may be prepared as short- or long-term lines and stored by conventional cryopreservation methods for thawing and administration, either immediately or after culturing for 1-3 days, to a subject suffering from injury to the CNS and in need of T-cell neuroprotection.

The use of semi-allogeneic T cells is based on the fact that T cells can recognize a specific antigen epitope presented by foreign APC, provided that the APC expresses the MHC molecule, class I or class II, to which the specific responding T-cell population is restricted, along with the antigen epitope recognized by the T cells. Thus, a semi-allogeneic population of T cells that can recognize at least one allelic product of the subject's MHC molecules, preferably a class II HLA-DR or HLA-DQ or other HLA molecule, and that is specific for a NS-associated antigen epitope, will be able to recognize the NS antigen in the subject's area of NS damage and produce the needed neuroprotective effect. There is little or no polymorphism in the adhesion molecules, leukocyte migration molecules, and accessory molecules needed for the T cells to migrate to the area of damage, accumulate there, and undergo activation. Thus, the semi-allogeneic T cells will be able to migrate and accumulate at the CNS site in need of neuroprotection and will be activated to produce the desired effect.

It is known that semi-allogeneic T cells will be rejected by the subject's immune system, but that rejection requires about two weeks to develop. Hence, the semi-allogeneic T cells will have the two-week window of opportunity needed to exert neuroprotection. After two weeks, the semi-allogeneic T cells will be rejected from the body of the subject, but that rejection is advantageous to the subject because it will rid the subject of the foreign T cells and prevent any untoward consequences of the activated T cells. The semi-allogeneic T cells thus provide an important safety factor and are a preferred embodiment.

It is known that a relatively small number of HLA class II molecules are shared by most individuals in a population. For example, about 50% of the Jewish population express the HLA-DR5 gene. Thus, a bank of specific T cells reactive to NS-antigen epitopes that are restricted to HLA-DR5 would be useful in 50% of that population. The entire population can be covered essentially by a small number of additional T cell lines restricted to a few other prevalent HLA molecules, such as DR1, DR4, DR2, etc. Thus, a functional bank of uniform T cell lines can be prepared and stored for immediate use in almost any individual in a given population. Such a bank of T cells would overcome any technical problems in obtaining a sufficient number of specific T cells from the subject in need of neuroprotection during the open window of treatment opportunity. The semi-allogeneic T cells will be safely rejected after accomplishing their role of neuroprotection. This aspect of the invention does not contradict, and is in addition to the use of autologous T cells as described herein.

The NS-specific activated T cells are preferably non-attenuated, although attenuated NS-specific activated T cells may be used. T cells may be attenuated using methods well-known in the art including, but not limited to, by gamma-irradiation, e.g., 1.5-10.0 Rads (Ben-Nun et al, 1981; Ben-Nun and Cohen, 1982); and/or by pressure treatment, for example as described in U.S. Pat. No. 4,996,194 (Cohen et al); and/or by chemical cross-linking with an agent such as formaldehyde, glutaraldehyde and the like, for example as described in U.S. Pat. No. 4,996,194 (Cohen et al); and/or by cross-linking and photoactivation with light with a photoactivatable psoralen compound, for example as described in U.S. Pat. No. 5,114,721 (Cohen et al); and/or by a cytoskeletal disrupting agent such as cytochalsin and colchicine, for example as described in U.S. Pat. No. 4,996,194 (Cohen et al). In a preferred embodiment the NS-specific activated T cells are isolated as described below. T cells can be isolated and purified according to methods known in the art (Mor and Cohen, 1995). For an illustrative example, see Example 1, Materials and Methods.

Circulating T cells of a subject which recognize an NS-antigen are isolated and expanded using known procedures (Burns et al, 1983; Pette et al, 1990; Martin et al, 1990; Schluesener et al, 1985; Suruhan-Dires Keneli et al, 1993, which are incorporated herein by reference in their entirety). In order to obtain NS-specific activated T cells, T cells are isolated and the NS-specific activated T cells are then expanded.

The isolated T cells may be activated by exposure of the cells to one or more of a variety of natural or synthetic NS-specific antigens or epitopes as described in section on NS-specific antigens, analogs thereof, peptides derived therefrom and analogs and derivatives thereof of said peptides hereinafter. During ex vivo activation of the T cells, the T cells may be activated by culturing in medium to which at least one suitable growth promoting factor has been added, such as cytokines, e.g., TNF-$\alpha$, IL-2 and/or IL-4.

In one embodiment, the NS-specific activated T cells endogenously produce a substance that ameliorates the effects of injury or disease in the NS.

In another embodiment, the NS-specific activated T cells endogenously produce a substance that stimulates other cells, including, but not limited to, transforming growth factor-$\beta$ (TGF-$\beta$), nerve growth factor (NGF), neurotrophic factor 3(NT-3), neurotrophic factor 4/5 (NT-4/5), brain derived neurotrophic factor (BDNF); IFN-$\gamma$ and IL-6, wherein the other cells, directly or indirectly, ameliorate the effects of injury or disease.

Following their proliferation in vitro, the T cells are administered to a mammalian, preferably a human, subject. T cell expansion is preferably performed using peptides corresponding to sequences in a non-pathogenic, NS-specific, self-protein.

A subject can initially be immunized with an NS-specific antigen using a non-pathogenic peptide of the self-protein. A T-cell preparation can be prepared from the blood of such immunized subjects, preferably from T cells selected for their specificity towards the NS-specific antigen. The selected T cells can then be stimulated to produce a T cell line specific to the self-antigen (Ben-Nun and Cohen, 1982).

NS-specific antigen activated T cells, obtained as described above, can be used immediately or may be preserved for later use, e.g., by cryopreservation as described below. NS-specific activated T cells may also be obtained using previously cryopreserved T cells, i.e., after thawing the cells, the T cells may be incubated with NS-specific antigen, optimally together with thymocytes, to obtain a preparation of NS-specific activated T cells.

As will be evident to those skilled in the art, the T cells can be preserved, e.g., by cryopreservation, either before or after culture.

Cryopreservation agents which can be used include, but are not limited to, dimethyl sulfoxide (DMSO) (Lovelock and Bishop, 1959; Ashwood-Smith, 1961), polyvinylpyrrolidone (Rinfret, 1960), glycerol, polyethylene glycol (Sloviter and Ravdin, 1962), albumin, dextran, sucrose, ethylene glycol, i-erythritol, D-ribitol, D-mannitol (Rowe et al, 1962), D-sorbitol, i-inositol, D-lactose, choline chloride (Bender et al, 1960), amino acids (Phan The Tran and Bender, 1960), methanol, acetamide, glycerol monoacetate (Lovelock, 1954), inorganic salts (Phan The Tran and Bender, 1960 and 1961) and DMSO combined with hydroxyethyl starch and human serum albumin (Zaroulis and Leiderman, 1980).

A controlled cooling rate is critical. Different cryoprotective agents (Rapatz et al, 1968) and different cell types have different optimal cooling rates. See, e.g., Rowe and Rinfret, 1962; Rowe, 1966; Lewis et al, 1967; Mazur, 1970) for effects of cooling velocity on survival of cells and on their transplantation potential. The heat of fusion phase where water turns to ice should be minimal. The cooling procedure can be carried out by use of, e.g., a programmable freezing device or a methanol bath procedure.

Programmable freezing apparatuses allow determination of optimal cooling rates and facilitate standard reproducible cooling. Programmable controlled-rate freezers such as Cryomed or Planar permit tuning of the freezing regimen to the desired cooling rate curve.

After thorough freezing, cells can be rapidly transferred to a long-term cryogenic storage vessel. In one embodiment, samples can be cryogenically stored in mechanical freezers, such as freezers that maintain a temperature of about $-80°$ C. or about $-20°$ C. In a preferred embodiment, samples can be cryogenically stored in liquid nitrogen ($-196°$ C.) or its vapor. Such storage is greatly facilitated by the availability of highly efficient liquid nitrogen refrigerators, which resemble large Thermos containers with an extremely low vacuum and internal super insulation, such that heat leakage and nitrogen losses are kept to an absolute minimum.

Considerations and procedures for the manipulation, cryopreservation, and long term storage of T cells can be found, for example, in the following references, incorporated by reference herein: Gorin, 1986; *Bone-Marrow Conservation, Culture and Transplantation*, 1968.

Other methods of cryopreservation of viable cells, or modifications thereof, are available and envisioned for use, e.g., cold metal-mirror techniques. See Livesey and Linner, 1987; Linner et al, 1986; see also U.S. Pat. No. 4,199,022 by Senken et al, U.S. Pat. No. 3,753,357 by Schwartz, U.S. Pat. No. 4,559,298 by Fahy.

Frozen cells are preferably thawed quickly (e.g., in a water bath maintained at 37-47° C.) and chilled immediately upon thawing. It may be desirable to treat the cells in order to prevent cellular clumping upon thawing. To prevent clumping, various procedures can be used, including but not limited to the addition before or after freezing of DNAse (Spitzer et al, 1980), low molecular weight dextran and citrate, citrate, hydroxyethyl starch (Stiff et al, 1983), or acid citrate dextrose (Zaroulis and Leiderman, 1980), etc.

The cryoprotective agent, if toxic in humans, should be removed prior to therapeutic use of the thawed T cells. One way in which to remove the cryoprotective agent is by dilution to an insignificant concentration.

Once frozen T cells have been thawed and recovered, they are used to promote neuroprotection as described herein with respect to non-frozen T cells. Once thawed, the T cells may be used immediately, assuming that they were activated prior to freezing. Preferably, however, the thawed cells are cultured before injection to the patient in order to eliminate non-viable cells. Furthermore, in the course of this culturing over a period of about one to three days, an appropriate activating agent can be added so as to activate the cells, if the frozen cells were resting T cells, or to help the cells achieve a higher rate of activation if they were activated prior to freezing. Usually, time is available to allow such a culturing step prior to administration as the T cells may be administered as long as a week after injury, and possibly longer, and still maintain their neuro-regenerative and neuroprotective effect.

To minimize secondary damage after nerve injury, patients can be treated by administering autologous or semi-allogeneic T lymphocytes sensitized to at least one appropriate NS-antigen. As the window of opportunity has not yet been precisely defined, therapy should be administered as soon as possible after the primary injury to maximize the chances of success, preferably within about one week.

To bridge the gap between the time required for activation and the time needed for treatment, a bank with autologous, semi-allogeneic or allogeneic T cells can be established for future use.

Thus, in another embodiment, the invention provides cell banks that can be established to store NS-sensitized T cells for neuroprotective treatment of individuals at a later time, as needed.

In one embodiment, autologous T cells may be obtained from an individual and the cell bank will contain personal vaults of autologous T lymphocytes prepared for future use for neuroprotective therapy against secondary degeneration in case of NS injury. T lymphocytes are isolated from the blood, sensitized to a NS-antigen, and the cells are then frozen and suitably stored under the person's name, identity number, and blood group, in a cell bank until needed.

Additionally, autologous stem cells of the CNS can be processed and stored for potential use by an individual patient in the event of traumatic disorders of the NS such as ischemia or mechanical injury, as well as for treating neurodegenerative conditions such as Alzheimer's disease or Parkinson's disease.

Alternatively, allogeneic or semi-allogeneic T cells may be stored such that a bank of T cells of each of the most common MHC-class II types are present. The semi-allogeneic or allogeneic T cells are stored frozen for use by any individual who shares one MHC type II molecule with the source of the T cells.

In case an individual is to be treated for an injury, preferably autologous stored T cells are used, but, if autologous T cells are not available, then cells should be used which share an MHC type II molecule with the patient, and these would be expected to be operable in that individual.

The cells are preferably stored in an activated state after exposure to an NS-antigen or peptide derived therefrom. However, the cells may also be stored in a resting state and activated once they are thawed and prepared for use. The cell lines of the bank are preferably cryopreserved. The cell lines are prepared in any way which is well known in the art. Once the cells are thawed, they are preferably cultured prior to injection in order to eliminate non-viable cells. During this culturing, the cells can be activated or reactivated using the same NS-antigen or peptide as used in the original activation. Alternatively, activation may be achieved by culturing in the presence of a mitogen, such as phytohemagglutinin (PHA) or concanavalin A (preferably the former). This will place the cells into an even higher state of activation. The few days that it takes to culture the cells should not be detrimental to the patient as the treatment in accordance with the present invention may occuo still be effective. Alternatively, if time is of the essencer any time up to a week or more after the injury in order t, the stored cells may be administered immediately after thawing.

NS-Specific Antigens, Analogs therof, Peptides Derived Therefrom, and Analogs and Derivatives Thereof The term "NS-specific antigen" as used herein refers to an antigen of the NS that specifically activates T cells such that following activation the activated T cells accumulate at a site of injury or disease in the NS of the patient.

The NS-specific antigen used according to the present invention may be an antigen obtained from NS tissue, preferably from tissue at a site of CNS injury or disease. It may be a crude NS-tissue preparation, e.g., derived from NS tissue obtained from mammalian NS that may include cells, both living or dead cells, membrane fractions of such cells or tissue, etc., and may be obtained by an NS biopsy or necropsy from a mammal, preferably human, tissue including, but not limited to, from a site of CNS injury; from cadavers; and from cell lines grown in culture.

In one embodiment, the NS-specific antigen is an isolated or purified antigen. The NS-specific antigen may be isolated and purified by standard methods including chromatography (e.g., ion exchange, affinity, and sizing column chromatography), centrifugation, differential solubility, or by any other standard technique for the purification of antigens. The functional properties may be evaluated using any suitable assay. Additionally, an NS-specific antigen may be a protein obtained by genetic engineering, chemically synthesized, etc.

In the practice of the invention, natural or synthetic NS-specific antigens are preferred and include, without being limited to, myelin basic protein (MBP), proteolipid protein (PLP), myelin oligodendrocyte glycoprotein (MOG), myelin-associated glycoprotein (MAG), S-100, β-amyloid, Thy-1, P0, P2, neurotransmitter receptors, Nogo and Nogo receptor (NgR).

Specific illustrative examples of useful NS-specific antigens include but are not limited to, human MBP, depicted in FIG. 21 (SEQ ID NO:12); human PLP, depicted in FIG. 22 (SEQ ID NO:13); human MOG, depicted in FIG. 23 (SEQ ID NO:14), rat Nogo A, B and C (Chen et al, 2000; WO 00/31235) (SEQ ID NOs:18, 20 and 21), peptide p472 (SEQ ID NO:19), human Nogo A, B and C (Prinjha et al, 2000) (SEQ ID NOs:23-25), and human or mouse Nogo receptor (NgR) (Fournier et al, 2001) (SEQ ID NOs:26 and 27, respectively).

Also encompassed by the present invention are analogs of NS-specific antigens including, but not being limited to, those molecules comprising regions that are substantially homologous to the full-length NS-specific antigen, or fragments thereof. In various embodiments, these analogs will have at least 60% or 70% or 80% or 90% or 95% identity over an amino acid sequence of identical size or when compared to an aligned sequence in which the alignment is done by a computer homology program known in the art or whose encoding nucleic acid is capable of hybridizing to a coding nucleotide sequence of the full-length NS-specific antigen, under high stringency, moderate stringency, or low stringency conditions. Computer programs for determining homology may include, but are not limited to, TBLASTN, BLASTP, FASTA, TFASTA, and CLUSTALW (Pearson and Lipman, 1988; Altschul et al, 1990; Thompson, et al, 1994; Higgins, et al, 1996).

The NS-specific antigen analogs of the invention can be produced by various methods known in the art. The manipulations which result in their production can occur at the gene or protein level. For example, a cloned gene sequence can be modified by any of numerous strategies known in the art (Maniatis, 1990). The sequence can be cleaved at appropriate sites with restriction endonuclease(s), followed by further enzymatic modification if desired, isolated, and ligated in vitro.

Additionally, the coding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, chemical mutagenesis, in vitro site-directed mutagenesis (Hutchinson, et al, 1978), etc.

Manipulations may also be made at the protein level. Included within the scope of the invention are NS-specific antigen derivatives which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, NaBH$_4$; acetylation, formylation, oxidation, reduction; metabolic synthesis in the presence of tunicamycin; etc.

In a preferred embodiment, the invention relates to peptides derived from NS-specific antigens or from analogs thereof and to analogs or derivatives of said peptides, which are functionally active, i.e., they are capable of displaying one or more known functional activities associated with a full-length NS-specific antigen. Such functional activities include, but are not limited to, antigenicity (ability to bind, or compete with an NS-antigen for binding, to an anti-NS-specific antibody), immunogenicity (ability to generate antibody which binds to an NS-specific protein), and ability to interact with T cells, resulting in activation comparable to that obtained using the corresponding full-length NS-specific antigen. The crucial test is that the antigen which is used for activating the T cells causes the T cells to be capable of recognizing an antigen in the NS of the mammal (patient) being treated.

The NS-antigen derived peptide may be either: (1) an immunogenic peptide, i.e., a peptide that can elicit a human T-cell response detected by a T-cell proliferation assay or by cytokine, e.g., IFN-γ, IL-2, IL-4 or IL-10, production, or (2) a "cryptic epitope" (also designated herein as "immunosilent" or "non-immunodominant" epitope), i.e., a peptide that by itself can induce a T-cell immune response that is not induced by the whole antigen protein (see Moalem et al, 1999).

A peptide derived from a NS-specific antigen preferably has a sequence comprised within the NS-specific antigen sequence and has at least 10, 13, 15, 18, 20 or 50 contiguous amino acids of the NS-specific antigen sequence. In one embodiment, the peptide derived from an NS-specific antigen is a "cryptic epitope" of the antigen. A cryptic epitope activates specific T cells after an animal is immunized with the particular peptide, but not with the whole antigen. Cryptic epitopes for use in the present invention include, but are not limited to, peptides of the MBP sequence: peptides p11-30, p51-70, p87-99, p91-110, p131-150, and p151-170. Such cryptic epitopes are particularly preferred as T cells activated thereby will accumulate at the injury site, but are particularly weak in autoimmunity. Thus, they would be expected to have fewer side effects.

In another embodiment, the peptide derived from an NS-specific antigen is an immunogenic epitope of the antigen.

Examples of further peptides according to the invention are immunogenic peptides derived from the Nogo protein sequence such as, but not being limited to, the 18-mer p472 Nogo peptide (SEQ ID NO:19) and peptides derived from the Nogo receptor (Fournier et al, 2001) such as the 15-mer peptides of the sequences:

```
S G V P S N L P Q R L A G R D    (SEQ ID NO:28)

T R S H C R L G Q A G S G S S    (SEQ ID NO:29)
```

In still another embodiment of the invention, the peptide is an analog of a peptide derived from an NS-specific antigen that is immunogenic but not encephalitogenic. The most suitable peptides for this purpose are those in which an encephalitogenic self-peptide is modified at the T-cell receptor (TCR)

binding site and not at the MHC binding site(s), so that the immune response is activated but not anergized (Karin et al, 1998; Vergelli et al, 1996).

These analogs, also referred herein as modified peptides or altered peptides, may be produced by replacement of one or more amino acid residues of the peptide by other amino acid residues, preferably in their TCR binding site. Suitable replacements are those in which charged amino residues like lysine, proline or arginine are replaced by glycine or alanine residues. For example, altered peptides can be produced from peptides p11-30, p51-70, p87-99, p91-110, p131-150, and p151-170 of human MBP, for example from the p87-99 peptide in which the lysine 91 is replaced by glycine and/or the proline 96 is replaced by an alanine residue, thus converting an encephalitogenic peptide in immunogenic but non-encephalitogenic peptide that still recognizes the TCR. In the same way, altered peptides can be produced from the encephalitogenic p472 Nogo peptide (Nogo p623-640) by replacement of the lys 628 residue and from the Nogo receptor peptides above by replacement of the arg (R) residue by Val or Ala or another similar residue.

In addition, the analogs also comprise replacement of one or more amino acid residues of the peptide or addition to the peptide of non-natural amino acids including, but not limited to, the D-isomers of the common amino acids, α-aminoisobutyric acid; 4-aminobutyric acid (Abu); 2-Abu (γ-Abu); 6-amino hexanoic acid (ε-Ahx); 2-aminoisobutyric acid (Aib); 3-aminopropionic acid; ornithine; norleucine (Nle); norvaline (Nva); hydroxyproline; sarcosine; citrulline; cysteic acid; t-butylglycine; t-butylalanine; phenylglycine; cyclohexylalanine; β-alanine; fluoro-amino acids; designer amino acids such as β-methyl amino acids, Cα-methyl amino acids, Nα-methyl amino acids, and amino acid analogs in general. Furthermore, the amino acid can be D (dextrorotary) or L (levoratory).

Furthermore, the invention also comprises chemical derivatives of the peptides of the invention including, but not being limited to, esters of both carboxylic and hydroxy groups, amides, and the like.

The NS-specific antigen peptides of the invention can be chemically synthesized. For example, a peptide corresponding to a portion of an antigen which comprises the desired domain or which mediates the desired activity can be synthesized by use of a peptide synthesizer.

The functional activity of NS-specific antigens and peptides derived therefrom and analogs and derivatives thereof can be assayed by various methods known in the art, including, but not limited to, T-cell proliferation assays (Mor and Cohen, 1995) and cytokine production assays.

An NS-specific antigen or peptide derived therefrom or derivative thereof may be kept in solution or may be provided in a dry form, e.g., as a powder or lyophilizate, to be mixed with appropriate solution prior to use. They may be used both as ingredients of pharmaceutical compositions for neuroprotection and preventing or inhibiting the effects of injury or disease that result in NS degeneration or for promoting nerve regeneration in the NS, particularly in the CNS as well as for in vivo or in vitro activation of T cells.

Nucleotide Sequences Encoding NS-Antigens and Peptides Derived Therefrom

The present invention further provides pharmaceutical compositions comprising a therapeutically effective amount of a nucleotide sequence encoding an NS-specific antigen or a peptide derived therefrom or an analog thereof and methods of use of such compositions to promote nerve regeneration or for neuroprotection and prevention or inhibition of neuronal degeneration in the CNS or PNS in which the amount is effective to ameliorate the effects of an injury or disease of the NS.

Specific illustrative examples of useful nucleotide sequences encoding NS-specific antigens or peptides derived from an NS-specific antigen include, but are not limited to, nucleotide sequences encoding rat MBP, depicted in FIG. 15 (SEQ ID NO:1); human MBP, depicted in FIG. 16 (SEQ ID NO:2); human PLP, depicted in FIG. 17(A-F) (SEQ ID NOs: 3-8); human MOG, depicted in FIG. 18 (SEQ ID NO:9); rat PLP and variant, depicted in FIG. 19 (SEQ ID NO:10); rat MAG, depicted in FIG. 20 (SEQ ID NO:11); rat Nogo (SEQ ID NO:17); and human Nogo (SEQ ID NO:22). Other illustrative examples are the nucleotide sequences disclosed in Chen et al (2000), Prinjha et al (2000) and Fournier et al (2001) (the contents of each of which being hereby incorporated herein by reference) encoding rat and human Noga A, B and C and mouse and human NgR.

Therapeutic Uses

The T cells, NS-specific antigens, analogs thereof, peptides derived therefrom and analogs and derivatives thereof, and nucleotide sequences described in the previous sections and compositions comprising them may be used to promote nerve regeneration or to confer neuroprotection and prevent or inhibit secondary degeneration which may otherwise follow primary NS injury, e.g., spinal cord injury, blunt trauma, penetrating trauma, hemorrhagic stroke, ischemic stroke or damages caused by surgery such as tumor excision.

In addition, such compositions may be used to ameliorate the effects of disease that result in a degenerative process, e.g., degeneration occurring in either gray or white matter (or both) as a result of various diseases or disorders, including, without limitation: diabetic neuropathy, senile dementias, Alzheimer's disease, Parkinson's disease, facial nerve (Bell's) palsy, glaucoma, Huntington's chorea, amyotrophic lateral sclerosis (ALS), non-arteritic optic neuropathy, intervertebral disc herniation, vitamin deficiency, prion diseases such as Creutzfeldt-Jakob disease, carpal tunnel syndrome, peripheral neuropathies associated with various diseases, including but not limited to, uremia, porphyria, hypoglycemia, Sjorgren Larsson syndrome, acute sensory neuropathy, chronic ataxic neuropathy, biliary cirrhosis, primary amyloidosis, obstructive lung diseases, acromegaly, malabsorption syndromes, polycythemia vera, IgA- and IgG gamma-pathies, complications of various drugs (e.g., metronidazole) and toxins (e.g., alcohol or organophosphates), Charcot-Marie-Tooth disease, ataxia telangectasia, Friedreich's ataxia, amyloid polyneuropathies, adrenomyeloneuropathy, Giant axonal neuropathy, Refsum's disease, Fabry's disease, lipoproteinemia, etc.

In a preferred embodiment, the NS-specific activated T cells, the NS-specific antigens, peptides derived therefrom, analogs and derivatives thereof or the nucleotides encoding said antigens, or peptides or any combination thereof of the present invention are used to treat diseases or disorders where promotion of nerve regeneration or prevention or inhibition of secondary neural degeneration is indicated, which are not autoimmune diseases or neoplasias. In a preferred embodiment, the compositions of the present invention are administered to a human subject.

While activated NS-specific T cells may have been used in the prior art in the course of treatment to develop tolerance to autoimmune antigens in the treatment of autoimmune diseases, or in the course of immunotherapy in the treatment of NS neoplasms, the present invention can also be used to ameliorate the degenerative process caused by autoimmune diseases or neoplasms as long as it is used in a manner not suggested by such prior art methods. Thus, for example, T cells activated by an autoimmune antigen have been suggested for use to create tolerance to the autoimmune antigen and, thus, ameliorate the autoimmune disease. Such treatment, however, would not have suggested the use of T cells directed to other NS antigens or NS antigens which will not induce tolerance to the autoimmune antigen or T cells which are administered in such a way as to avoid creation of tolerance. Similarly, for neoplasms, the effects of the present invention can be obtained without using immunotherapy processes suggested in the prior art by, for example, using an NS antigen which does not appear in the neoplasm. T cells activated with such an antigen will still accumulate at the site of neural degeneration and facilitate inhibition of this degeneration, even though it will not serve as immunotherapy for the tumor per se.

Nogo protein or a fragment thereof which are active in inhibiting cell proliferation have been disclosed as useful for treatment of a neoplastic disease of the CNS such as glioma, glioblastoma, medulloblastoma, craniopharyngioma, ependyoma, neuroblastoma and retinoblastoma. The present invention does not encompass the use of Nogo or a peptide derived therefrom for treatment of neoplasias in general, and for treatment of a neoplastic disease of the CNS, in particular.

Formulations and Administration

The present invention also provides pharmaceutical compositions useful in methods to promote nerve regeneration or to confer neuroprotection and prevent or inhibit neuronal degeneration in the CNS or PNS, comprising a therapeutically effective amount of at least one ingredient selected from the group consisting of:

(a) NS-specific activated T cells;
(b) a NS-specific antigen or an analog thereof;
(c) a peptide derived from an NS-specific antigen or from an analog thereof, or an analog or derivative of said peptide;
(d) a nucleotide sequence encoding an NS-specific antigen or an analog thereof;
(e) a nucleotide sequence encoding a peptide derived from an NS-specific antigen or from an analog thereof, or an analog of said peptide; or
(f) any combination of (a)-(e).

The compositions comprising ingredients (b) and/or (c) above are also effective to activate T cells in vitro, wherein the activated T cells inhibit or ameliorate the effects of an injury or disease of the NS.

Pharmaceutical compositions for use in accordance with the present invention may be formulated in conventional manner using one or more physiologically acceptable carriers or excipients. The carrier(s) must be "acceptable" in the sense of being compatible with the other ingredients of the composition and not deleterious to the recipient thereof.

The term "carrier" refers to a diluent, adjuvant, excipient, or vehicle with which the therapeutic is administered. The carriers in the pharmaceutical composition may comprise a binder, such as microcrystalline cellulose, polyvinylpyrrolidone (polyvidone or povidone), gum tragacanth, gelatin, starch, lactose or lactose monohydrate; a disintegrating agent, such as alginic acid, maize starch and the like; a lubricant or surfactant, such as magnesium stearate or sodium lauryl sulphate; a glidant, such as colloidal silicon dioxide; a sweetening agent, such as sucrose or saccharin; and/or a flavoring agent, such as peppermint, methyl salicylate, or orange flavoring.

Methods of administration include, but are not limited to, parenteral, e.g., intravenous, intraperitoneal, intramuscular, subcutaneous, mucosal (e.g., oral, intranasal, buccal, vaginal, rectal,, intraocular), intrathecal, topical and intradermal routes. Administration can be systemic or local.

For oral administration, the pharmaceutical preparation may be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions may take the form of, for example, tablets, lozenges or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well-known in the art.

Preparations for oral administration may be also suitably formulated to give controlled release of the active compound.

The compositions may be formulated for parenteral administration by injection, e.g., by bolus injection or continuous infusion. Formulations for injection may be presented in unit dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compositions may also be formulated as rectal compositions such as suppositories or retention enemas, e.g., containing conventional suppository bases such as cocoa butter or other glycerides.

For administration by inhalation, the compositions for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin, for use in an inhaler or insufflator may be formulated containing a powder mix of the compound and a suitable powder base such as lactose or starch.

In one embodiment, compositions comprising NS-specific activated T cells, an NS-specific antigen or peptide derived therefrom, or derivative thereof, or a nucleotide sequence encoding such antigen or peptide, are formulated in accordance with routine procedures as pharmaceutical compositions adapted for intravenous or intraperitoneal administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together. Where the composition is to be administered by infusion, it can be dispensed with an infusion bottle containing sterile pharmaceutical grade water or saline. Where the composition is administered by injection, an ampoule of sterile water or saline for injection can be provided so that the ingredients may be mixed prior to administration.

Pharmaceutical compositions comprising NS-specific antigen or peptide derived therefrom or derivative thereof may optionally be administered with an adjuvant.

The invention also provides a pharmaceutical pack or kit comprising one or more containers filled with one or more of the ingredients of the pharmaceutical compositions of the invention.

In a preferred embodiment, the pharmaceutical compositions of the invention are administered to a mammal, preferably a human, shortly after injury or detection of a degenerative lesion in the NS. The therapeutic methods of the invention may comprise administration of an NS-specific activated T cell or an NS-specific antigen or peptide derived therefrom or derivative thereof, or a nucleotide sequence encoding such antigen or peptide, or any combination thereof. When using combination therapy, the NS-specific antigen may be administered before, concurrently or after administration of NS-specific activated T cells, a peptide derived from an NS-specific antigen or derivative thereof or a nucleotide sequence encoding such antigen or peptide.

In one embodiment, the compositions of the invention are administered in combination with one or more of the following: (a) mononuclear phagocytes, preferably cultured monocytes (as described in PCT publication No. WO 97/09985, which is incorporated herein by reference in its entirety), that have been stimulated to enhance their capacity to promote neuronal regeneration; (b) a neurotrophic factor such as acidic fibroblast growth factor; and (c) an anti-inflammatory therapeutic substance, e.g., an anti-inflammatory steroid, such as dexamethasone or methyl-prednisolone, or a non-steroidal anti-inflammatory peptide, such as Thr-Lys-Pro (TKP)).

In another embodiment, mononuclear phagocyte cells according to PCT Publication No. WO 97/09985 and U.S. Pat. No. 6,267,955, are injected into the site of injury or lesion within the CNS, either concurrently, prior to, or following parenteral administration of NS-specific activated T cells, an NS-specific antigen or peptide derived therefrom or derivative thereof, or a nucleotide sequence encoding such antigen or peptide In another embodiment, administration of NS-specific activated T cells, NS-specific antigen or peptide sequence encoding such antigen or peptide, may be administered as a single dose or may be repeated, preferably at 2-week intervals and then at successively longer intervals once a month, once a quarter, once every six months, etc. The course of treatment may last several months, several years or occasionally also through the lifetime of the individual, depending on the condition or disease which is being treated. In the case of a CNS injury, the treatment may range between several days to months or even years, until the condition has stabilized and there is no or only a limited risk of development of secondary degeneration. In chronic human disease or Parkinson's disease, the therapeutic treatment in accordance with the invention may be for life.

As will be evident to those skilled in the art, the therapeutic effect depends at times on the condition or disease to be treated, on the individual's age and health condition, on other physical parameters (e.g., gender, weight, etc.) of the individual, as well as on various other factors, e.g., whether the individual is taking other drugs, etc.

The optimal dose of the therapeutic compositions comprising NS-specific activated T cells of the invention is proportional to the number of nerve fibers affected by NS injury or disease at the site being treated. In a preferred embodiment, the dose ranges from about $5 \times 10^6$ to about $10^7$ for treating a lesion affecting about $10^5$ nerve fibers, such as a complete transection of a rat optic nerve, and ranges from about $10^7$ to about $10^8$ for treating a lesion affecting about $10^6$–$10^7$ nerve fibers, such as a complete transection of a human optic nerve. As will be evident to those skilled in the art, the dose of T cells can be scaled up or down in proportion to the number of nerve fibers thought to be affected at the lesion or site of injury being treated.

The following examples illustrate certain features of the present invention but are not intended to limit the scope of the present invention.

EXAMPLE 1

Accumulation of Activated T Cells in Injured Optic Nerve

Materials and Methods

Animals

Female Lewis rats were supplied by the Animal Breeding Center of the Weizmann Institute of Science (Rehovot, Israel), matched for age (8-12 weeks) and housed four to a cage in a light and temperature-controlled room.

Media

The T-cell proliferation medium contained the following: Dulbecco's modified Eagle's medium (DMEM, Biological Industries, Israel) supplemented with 2 mM L-glutamine (L-Glu, Sigma, USA), $5 \times 10^{-5}$ M 2-mercaptoethanol (2-ME, Sigma), penicillin (100 IU/ml; Biological Industries), streptomycin (100 µ/ml; Biological Industries), sodium pyruvate (1 mM; Biological Industries), non-essential amino acids (1 ml/100 ml; Biological Industries) and autologous rat serum 1% (vol/vol) (Mor et al, 1990). Propagation medium contained: DMEM, 2-ME, L-Glu, sodium pyruvate, non-essential amino acids and antibiotics in the same concentration as above with the addition of 10% fetal calf serum (FCS), and 10% T cell growth factor (TCGF) obtained from the supernatant of concanavalin A-stimulated spleen cells (Mor et al, 1990).

Antigens

MBP from the spinal cords of guinea pigs was prepared as described (Hirshfeld, et al, 1970). OVA was purchased from Sigma (St. Louis, Mo.). The p51-70 of the rat 18.5 kDa isoform of MBP (sequence: APKRGSGKDSHTRTTHYG) (SEQ ID NO:15) and the p277 peptide of the human hsp60 (sequence: VLGGGCALLRCPALDSLTPANED) (SEQ ID NO:16) (Elias et al, 1991) were synthesized using the 9-fluorenylmethoxycarbonyl (Fmoc) technique with an automatic multiple peptide synthesizer (AMS 422, ABIMED, Langenfeld, Germany). The purity of the peptides was analyzed by HPLC and amino acid composition.

T Cell Lines

T-cell lines were generated from draining lymph node cells obtained from Lewis rats immunized with an antigen (described above in Antigens). The antigen was dissolved in PBS (1 mg/ml) and emulsified with an equal volume of IFA (Difco Laboratories, Detroit, Mich.) supplemented with 4 mg/ml *Mycobacterium tuberculosis* (Difco 15 Laboratories, Detroit, Mich.). The emulsion (0.1 ml) was injected into hind foot pads of the rats. Ten days after the antigen was injected, the rats were killed and draining lymph nodes were surgically removed and dissociated. The cells were washed and activated with the antigen (10 µg/ml) in proliferation medium (described above in Media). After incubation for 72 h at 37° C., 90% relative humidity and 7% $CO_2$, the cells were transferred to propagation medium (described above in Media). Cells were grown in propagation medium for 4-10 days before being re-exposed to antigen (10 µg/ml) in the presence of irradiated (2000 rad) thymus cells ($10^7$ cells/ml) in proliferation medium. The T cell lines were expanded by repeated re-exposure and propagation.

Crush Injury of Rat Optic Nerve

Crush injury of the optic nerve was performed as previously described (Duvdevani et al, 1990). Briefly, rats were deeply anesthetized by i.p. injection of Rompum (xylazine, 10 mg/kg; Vitamed, Israel) and Vetaler (ketamine, 50 mg/kg; Fort Dodge Laboratories, Fort Dodge, Iowa). Using a binocular operating microscope, a lateral canthotomy was performed in the right eye and the conjunctiva was incised lateral to the cornea. After separation of the retractor bulbi muscles, the optic nerve was exposed intraorbitally by blunt dissection. Using calibrated cross-action forceps, a moderate crush injury was inflicted on the optic nerve, 2 mm form the eye (Duvdevani et al, 1990). The contralateral nerve was left undisturbed and was used as a control.

Immunocytochemistry of T Cells

Longitudinal cryostat nerve sections (20 µm thick) were picked up onto gelatin glass slides and frozen until preparation for fluorescent staining. Sections were thawed and fixed in ethanol for 10 minutes at room temperature, washed twice with double-distilled water ($ddH_2O$), and incubated for 3 minutes in PBS containing 0.05% polyoxyethylene-sorbitan monolaurate (Tween-20; Sigma, USA). Sections were then incubated for 1 hr at room temperature with a mouse monoclonal antibody directed against rat T cell receptor (TCR) (1:100, Hunig et al, 1989), in PBS containing 3% FCS and 2% BSA. After three washes with PBS containing 0.05% Tween-20, the sections were incubated with fluorescein isothiocyanate-conjugated goat anti-mouse IgG (with minimal cross-section to rat, human, bovine and horse serum proteins) (Jackson ImmunoResearcch, West Grove, Pa.) for one hour at room temperature. The sections were then washed with PBS containing Tween-20 and treated with glycerol containing 1,4-diazobicyclo-(2,2,2) octane (Sigma), to inhibit quenching of fluorescence. The sections were viewed with a Zeis microscope and cells were counted. Staining in the absence of first antibody was negative.

RESULTS

FIG. 1 shows accumulation of T cells measured immunohistochemically. The number of T cells was considerably higher in injured nerves rats injected with anti-MBP, anti-OVA or anti-p277 cells; statistical analysis (one-way ANOVA) showed significant differences between T cell numbers in injured optic nerves of rats injected with anti-MBP, anti-OVA, or anti-p277 T cells and in injured optic nerves of rats injected with PBS ($P<0.001$); and between injured optic nerves and uninjured optic nerves of rats injected with anti-MBP, anti-OVA, or anti-p277 T cells ($P<0.001$).

EXAMPLE 2

Neuroprotection by Autoimmune Anti-MBP T Cells
Material and Methods

Animals, media, antigens, crush injury of rat optic nerve, sectioning of nerves, T cell lines, and immunolabeling of nerve sections are described in Example 1, supra.

Retrograde Labeling and Measurement of Primary Damage and Secondary Degeneration Primary damage of the optic nerve axons and their attached RGCs were measured after the immediate post-injury application of the fluorescent lipophilic dye 4-Di-10-Asp) (Molecular Probes Europe BV, Netherlands) distal to the site of injury. Only axons that are intact are capable of transporting the dye back to their cell bodies; therefore, the number of labeled cell bodies is a measure of the number of axons that survived the primary damage. Secondary degeneration was also measured by application of the dye distal to the injury site, but two weeks after the primary lesion was inflicted. Application of the neurotracer dye distal to the site of the primary crush after two weeks ensures that only axons that survived both the primary damage and the secondary degeneration will be counted. This approach makes it possible to differentiate between neurons that are still functionally intact and neurons in which the axons are injured but the cell bodies are still viable, as only those neurons whose fibers are morphologically intact can take up dye applied distally to the site of injury and transport it to their cell bodies. Using this method, the number of labeled RGCs reliably reflects the number of still-functioning neurons. Labeling and measurement were done by exposing the right optic nerve for a second time, again without damaging the retinal blood supply. Complete axotomy was done 1-2 mm from the distal border of the injury site and solid crystals (0.2-0.4 mm in diameter) of 4-Di-10-Asp were deposited at the site of the newly formed axotomy. Uninjured optic nerves were similarly labeled at approximately the same distance from the globe. Five days after dye application, the rats were killed. The retina was detached from the eye, prepared as a flattened whole mount in 4% paraformaldehyde solution and examined for labeled RGCs by fluorescence microscopy. The percentage of RGCs surviving secondary degeneration was calculated using the following formula: (Number of spared neurons after secondary degeneration)/(Number of spared neurons after primary damage)×100.

Electrophysiological Recordings

Nerves were excised and their compound action potentials (CAPs) were recorded in vitro using a suction electrode experimental set-up (Yoles et al, 1996). At different times after injury and injection of T cells or PBS, rats were killed by intraperitoneal injection of pentobarbitone (170 mg/kg) (CTS Chemical Industries, Israel). Both optic nerves were removed while still attached to the optic chiasma, and were immediately transferred to a vial containing a fresh salt solution consisting of 126 mM NaCl, 3 mM KCl, 1.25 mM $NaH_2PO_2$ 26 mM $NaHCO_3$ 2 mM $MgSO_4$, 2 mM $CaCl_2$ and 10 mM D-glucose, aerated with 95% $O_2$ and 5% $CO_2$ at room temperature. After 1 hour, electrophysiological recordings were made. In the injured nerve, recordings were made in a segment distal to the injury site. This segment contains axons of viable RGCs that have escaped both primary and secondary damage, as well as the distal stumps of non-viable RGCs that have not yet undergone Wallerian degeneration. The nerve ends were connected to two suction Ag—AgCl electrodes immersed in the bathing solution at 37° C. A stimulating pulse was applied through the electrode, and the CAP was recorded by the distal electrode. A stimulator (SD9; Grass Medical Instruments, Quincy, Mass.) was used for supramaximal electrical stimulation at a rate of 1 pps to ensure stimulation of all propagating axons in the nerve. The measured signal was transmitted to a microelectrode AC amplifier (model 1800; A-M Systems, Everett, Wash.). The data were processed using the LabView 2.1.1 data acquisition and management system (National Instruments, Austin, Tex.). For each nerve, the difference between the peak amplitude and the mean plateau of eight CAPs was computed and was considered as proportional to the number of propagating axons in the optic nerve. The experiments were done by experimenters "blinded", to sample identity. In each experiment the data were normalized relative to the mean CAP of the uninjured nerves from PBS-injected rats.

Clinical Evaluation of Experimental Autoimmune Encephalomyelitis (EAE)

Clinical disease was scored every 1 to 2 days according to the following neurological scale: 0, no abnormality; 1, tail atony; 2, hind limb paralysis; 3, paralysis extending to thoracic spine; 4, front limb paralysis; 5, moribund state.

RESULTS

Neuroprotection BY Autoimmune Anti-MBP T Cells

Figure 2:
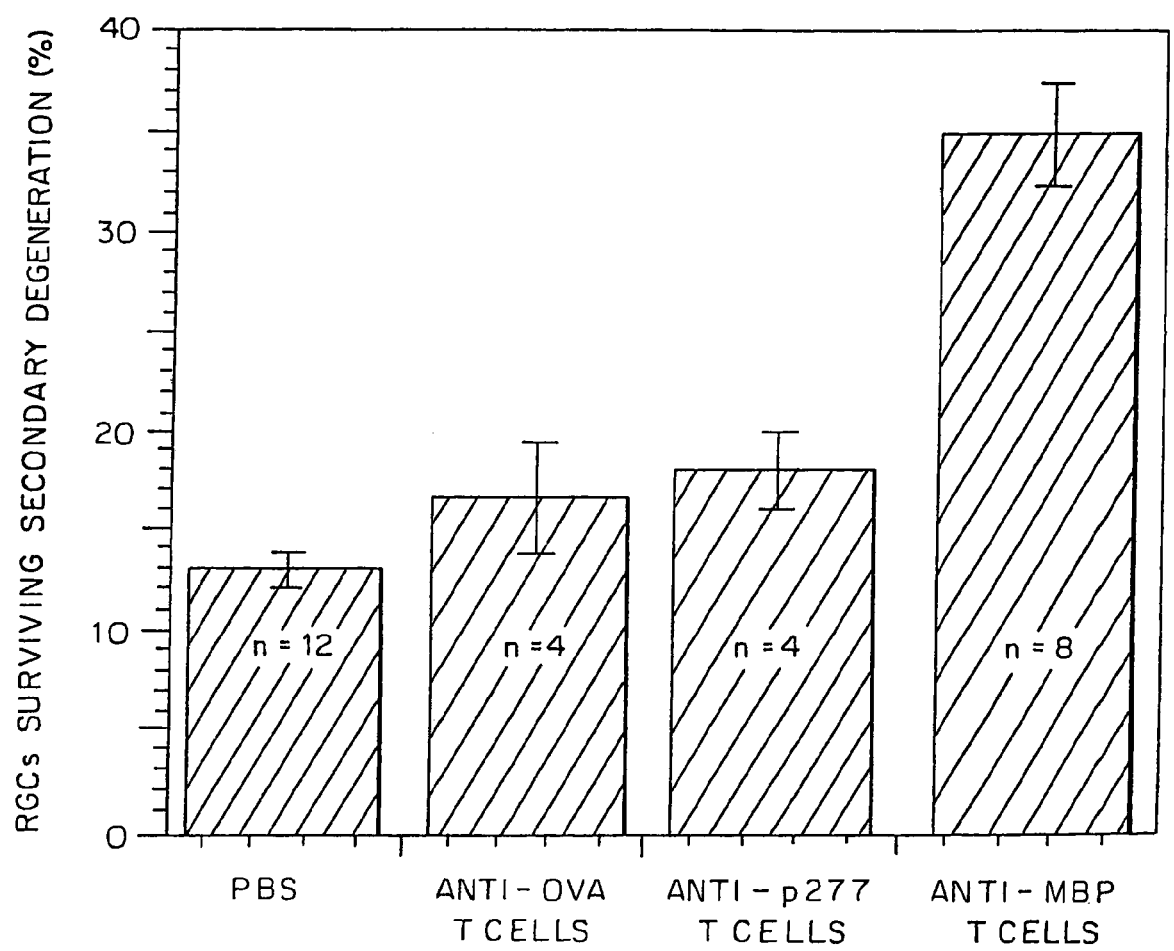
FIG. 2 is a bar graph illustrating that T cells specific to MBP, but not to OVA or p277, protect neurons from secondary degeneration. Immediately after optic nerve injury, rats were injected with anti-MBP, anti-OVA or anti-p277 T cells, or with PBS. The neurotracer dye 4-Di-10-Asp was applied to optic nerves distal to the site of the injury, immediately after injury (for assessment of primary damage) or two weeks later (for assessment of secondary degeneration). Five days after dye application, the retinas were excised and flat-mounted. Labeled retinal ganglion cells (RGCs) from three to five randomly selected fields in each retina (all located at approximately the same distance from the optic disk) were counted by fluorescence microscopy. RGC survival in each group of injured nerves was expressed as the percentage of the total number of neurons spared after the primary injury (42% of neurons remained undamaged after the primary injury). The neuroprotective effect of anti-MBP T cells compared with that of PBS was significant ($P<0.001$, one-way ANOVA). Anti-OVA T cells or anti-p277 T cells did not differ significantly from PBS in their effects on the protection of neurons that had escaped primary injury (P>0.05, one-way ANOVA). The results are a summary of five experiments. Each group contained five to ten rats.

Morphological analyses were done to assess the effect of the T cells on the response of the nerve to injury, and specifically on secondary degeneration. Rats were injected intraperitoneally immediately after optic nerve injury with PBS or with $1 \times 10^7$ activated T cells of the various cell lines. The degree of primary damage to the optic nerve axons and their attached RGCs was measured by injecting the dye 4-Di-10-Asp distal to the site of the lesion immediately after the injury. A time lapse of 2 weeks between a moderate crush injury and dye application is optimal for demonstrating the number of still viable labeled neurons as a measure of secondary degeneration, and as the response of secondary degeneration to treatment. Therefore, secondary degeneration was quantified by injecting the dye immediately or 2 weeks after the primary injury, and calculating the additional loss of RGCs between the first and the second injections of the dye. The percentage of RGCs that had survived secondary degeneration was then calculated. The percentage of labeled RGCs (reflecting still-viable neurons) was significantly greater in the retinas of the rats injected with anti-MBP T cells than in the retinas of the PBS-injected control rats (FIG. 2). In contrast, the percentage of labeled 30 RGCs in the retinas of the rats injected with anti-OVA or anti-p277 T cells was not significantly greater than that in the control retinas. Thus, although the three T cell lines accumulated at the site of injury, only the MBP-specific autoimmune T cells had a substantial effect in limiting the extend of secondary degeneration. Labeled RGCs of injured optic nerves of rats injected with PBS (FIG. 3A), with anti-p277 T cells (FIG. 3B) or with anti-MBP T cells (FIG. 3C) were compared morphologically using micrographs.

Clinical Severity Of EAE

Figure 4A:
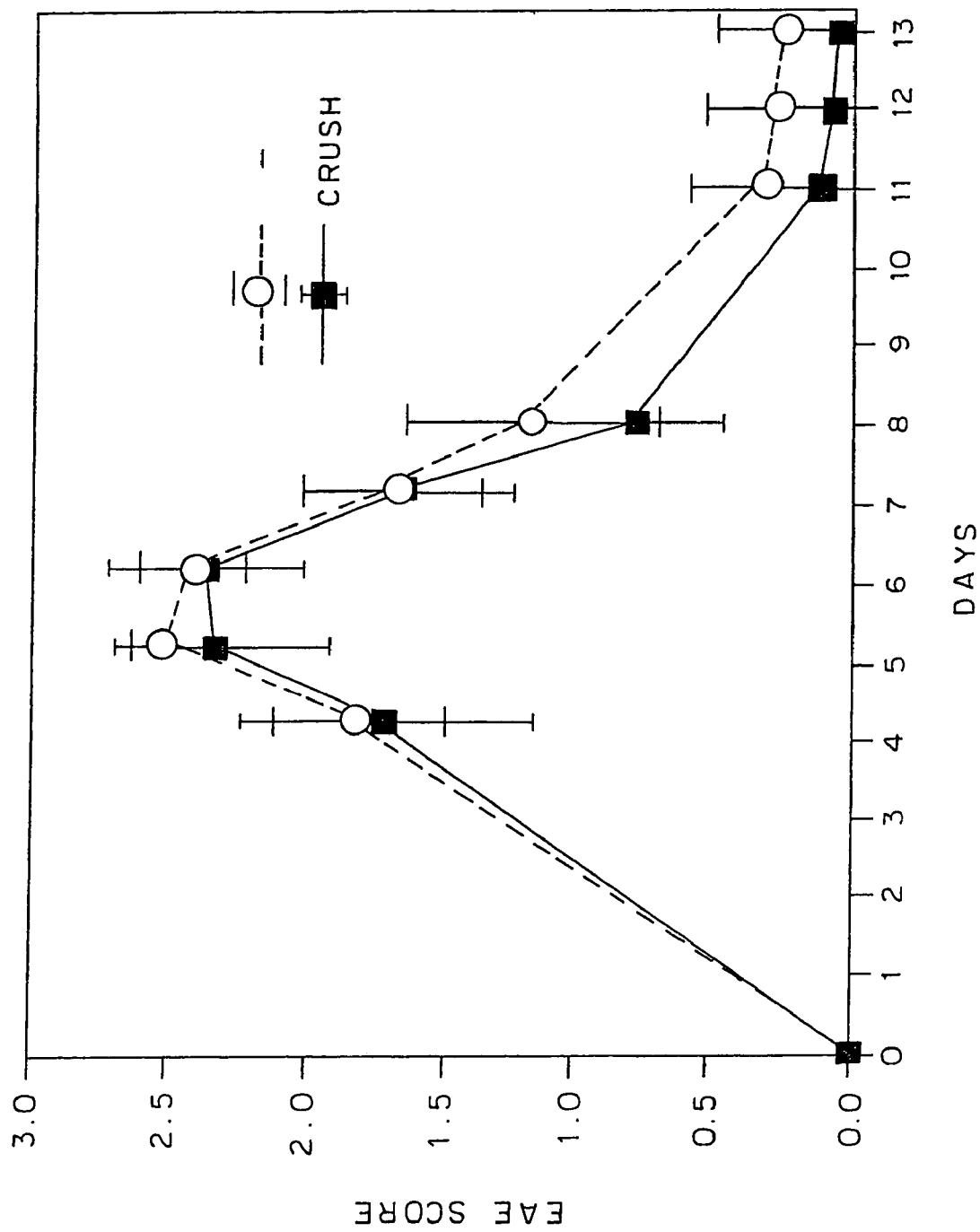
FIGS. 4(A-B) are graphs showing that clinical severity of EAE is not influenced by an optic nerve crush injury. For the results presented in FIG. 4A, Lewis rats, either uninjured (dash line) or immediately after optic nerve crush injury (solid line), were injected with activated anti-MBP T cells. EAE was evaluated according to a neurological paralysis scale. [Data points represent±s.e.m.] These results represent a summary of three experiments. Each group contained five to nine rats.
FIG. 4B shows that the number of RGCs in the uninjured optic nerve is not influenced by injection of anti-MBP T cells. Two weeks after the injection of anti-MBP T cells or PBS, 4-Di-10-Asp was applied to the optic nerves. After 5 days the retinas were excised and-flat-mounted. Labeled RGCs from five fields (located at approximately the same distance from the optic disk) in each retina were counted and the average number per mm$^2$ was calculated. There was no difference between the numbers of labeled RGCs in rats injected with anti-MBP T cells ($T_{MBP}$) and in PBS-injected control rats.

Animals were injected i.p. with $10^7$ $T_{MBP}$ cells with or without concurrent optic nerve crush injury. The clinical course of the rats injected with the TMBP cells was evaluated according to the neurological paralysis scale. Each group contained 5-9 rats. The functional autoimmunity of the injected anti-MBP T cells was demonstrated by the development of transient EAE in the recipients of these cells. As can be seen in FIG. 4A, the course and severity of the EAE was not affected by the presence of the optic nerve crush injury.

Survival of RGCS in Non-Injured Nerves

Animals were injected i.p. with $10^7$ TMBP cells or PBS. Two weeks later, 4-Di-10-Asp was applied to the optic nerves. After five days the retinas were excised and flat mounted. Labeled RGCs from five fields (located at approximately the same distance from the optic disk), in each retina were counted and their average number per are ($mm^2$) was calculated.

Figure 4B:
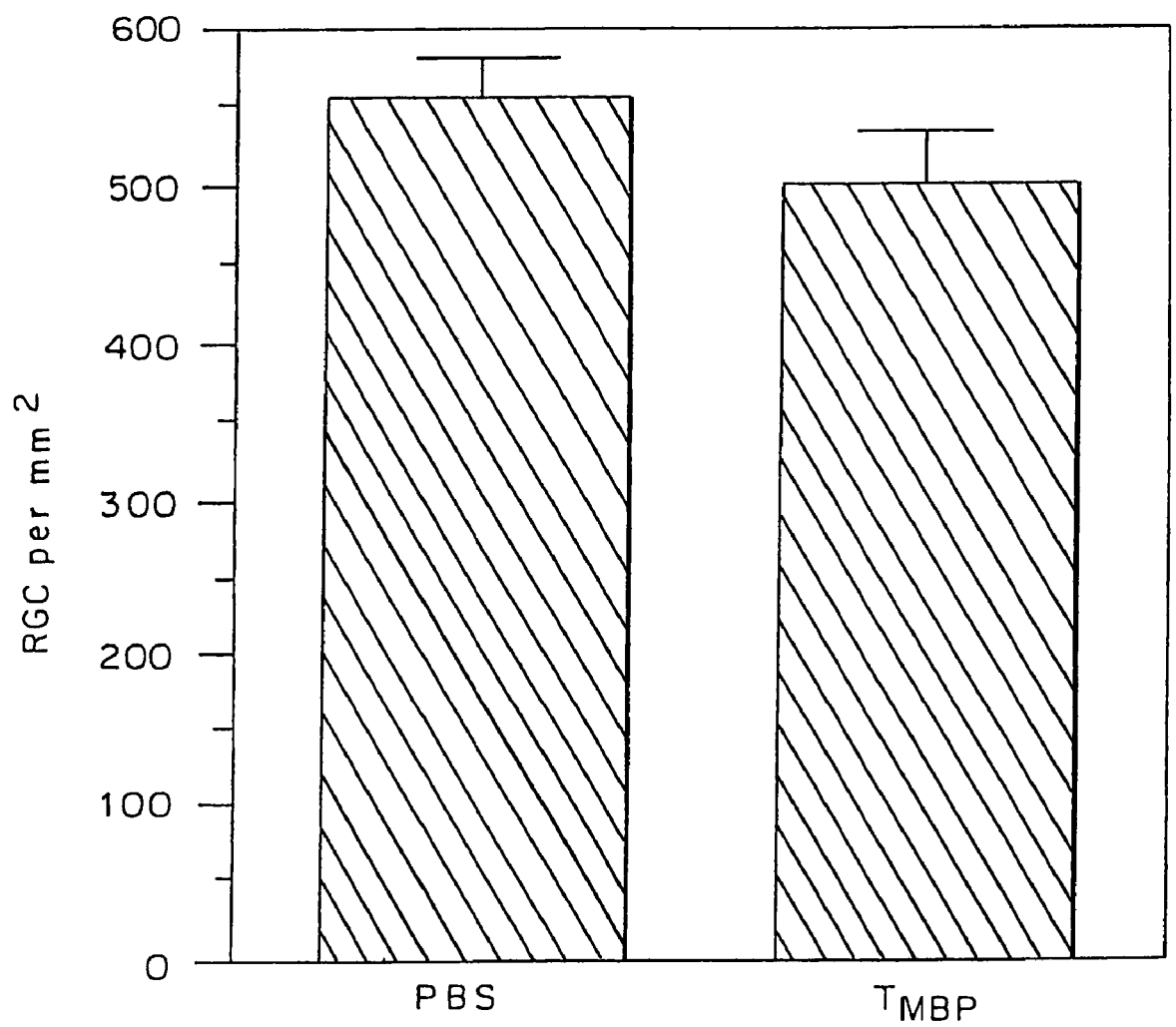

As can be seen in FIG. 4B, there is no difference in the number of surviving RGCs per area ($mm^2$) in non-injured optic nerves of rats injected with anti-MBP T cells compared to in rats injected with PBS.

Neuroprotection by T Cells Reactive to a Cryptic Epitope— (p51-70)MBP

Figure 5:
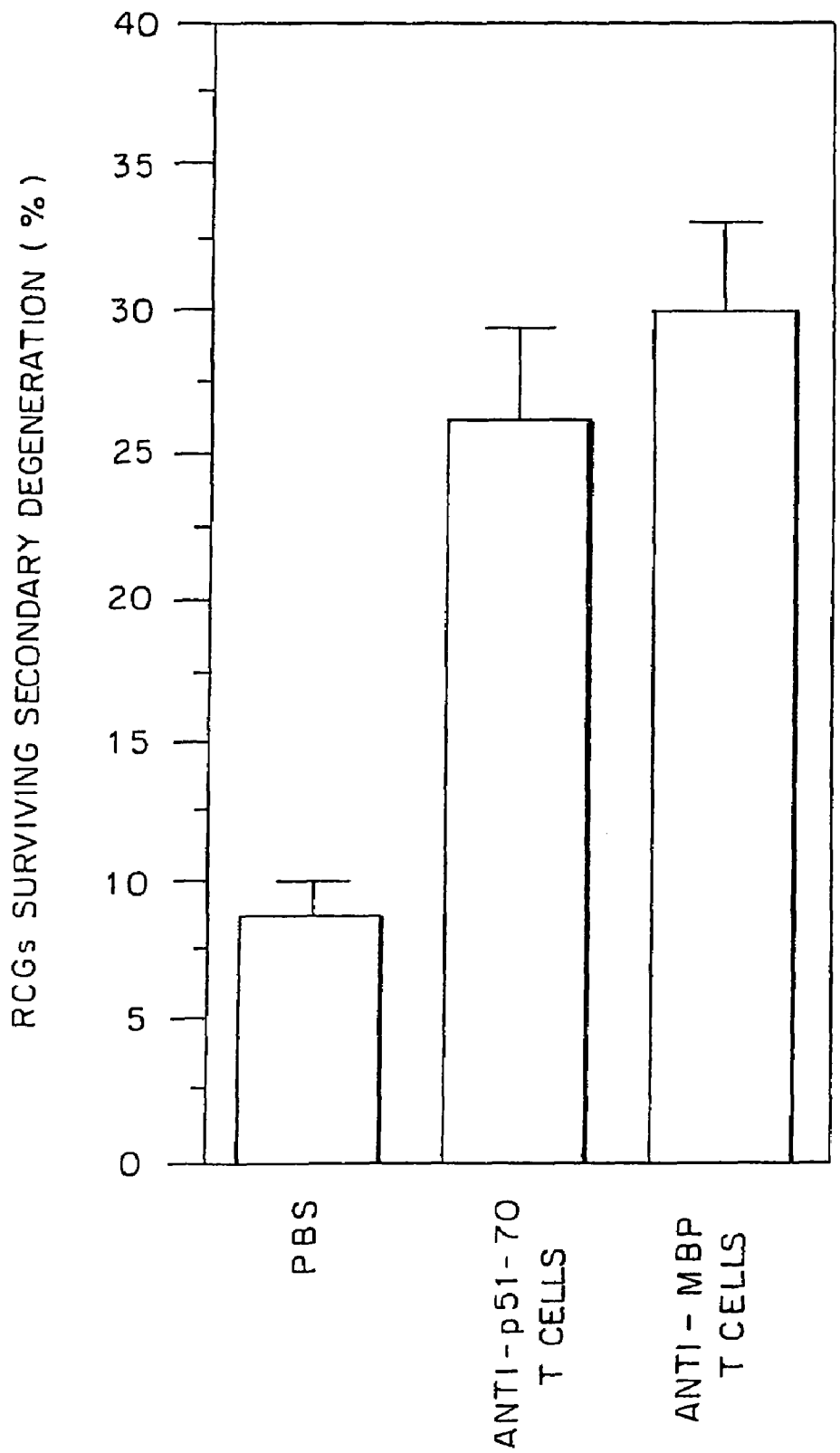
FIG. 5 is a bar graph showing that T cells specific to p51-70 of MBP protect neurons from secondary degeneration. Immediately after optic nerve injury, rats were injected with anti-MBP T cells, anti-p51-70 T cells, or PBS. 4-Di-10-Asp was applied to optic nerves distal to the site of the injury, immediately after injury (for assessment of primary damage) or two weeks later (for assessment of secondary degeneration). Five days after dye application, the retinas were excised and flat-mounted. Labeled RGCs from three to five randomly selected fields in each retina (all located at approximately the same distance from the optic disk) were counted by fluorescence microscopy. RGC survival in each group of injured nerves was expressed as the percentage of the total number of neurons spared after primary injury. Compared with that of PBS treatment, the neuroprotective effects of anti-MBP and of anti-p51-70 T cells were significant (P<0.001, one-way ANOVA).

To determine whether the neuroprotective effect of the anti-MBP T cells is correlated with their virulence, the effect of T cells reactive to a "cryptic" epitope of MBP, the peptide 51-70 (p51-70) was examined. "Cryptic" epitopes activate specific T cells after an animal is immunized with the particular peptide, but not with the whole antigen (Mor et al, 1995). The T cell line reactive to the whole MBP and the T cell line reactive to the cryptic epitope p51-70 were compared for the severity of the EAE they induced, and for their effects on secondary degeneration. In rats injected with the T cell line reactive to the cryptic epitope, disease severity (as manifested by the maximal EAE score) was significantly lower than that in rats injected with the T cell line reactive to the whole protein (Table 1). Whereas anti-MBP T cells caused clinical paralysis of the limbs, rats injected with the anti-p51-70 T cells developed only tail atony, not hind limb paralysis, and almost none showed weakness of the hind limbs. Despite this difference in EAE severity, the neuroprotective effect of the less virulent (anti-p51-70) T cells was similar to that of the more virulent (anti-MBP) T cells (FIG. 5). The percentage of RGCs surviving secondary degeneration in the retinas of rats injected with either of the lines was significantly higher than in the retinas of the PBS-injected rats. Thus, there was no correlation between the neuroprotective effect of the autoimmune T cells and their virulence. It is possible that the anti-p51-70 T cells encounter little antigen in the intact CNS, and therefore cause only mild EAE. Their target antigen may however become more available after injury, enabling these T cells to exert a neuroprotective effect.

TABLE 1

Anti-MBP and Anti-p501-70 T Cells Vary in Pathogenicity

| T Cell Line | Clinical EAE | Mean Max. Score |
| --- | --- | --- |
| Whole MBP | Moderate to Severe | 2.00 + 0.2 |
| p51-70 of MBP | Mild | 0.70 + 0.2 |

Immediately after optic nerve crush injury, Lewis rats were injected with activated anti-MBP T cells or anti-p51-70 T cells. The clinical course of EAE was evaluated according to the neurological paralysis scale. The mean maximal (max.) score ± s.e.m. was calculated as the average maximal score of all the diseased rats in each group. The table is a summary of nine experiments. Each group contains five to ten rats. Statistical analysis showed a significant difference between the mean maximal scoreof rats injected with anti-MBP T cells and that of rats injected with anti-p51-70 T cells (P = 0.039, Student's t-test)

Electrophysiological Activity

Figure 6A:
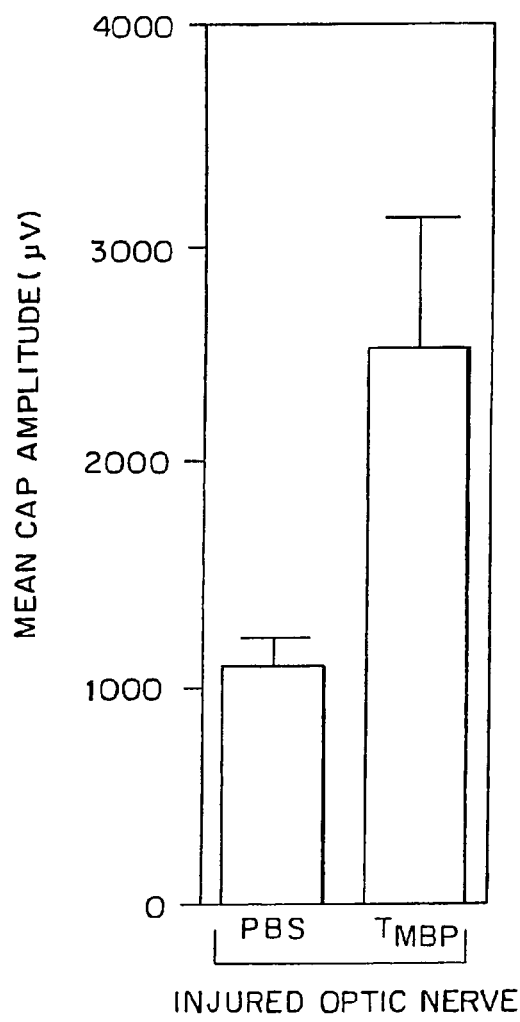
FIGS. 6(A-B) are graphs showing that anti-MBP T cells increase the compound action potential (CAP) amplitudes of injured optic nerves. Immediately after optic nerve injury, rats were injected with either PBS or activated anti-MBP T cells ($T_{MBP}$). Two weeks later, the CAPs of injured (FIG. 6A) and uninjured (FIG. 6B) nerves were recorded. There were no significant differences in mean CAP amplitudes between uninjured nerves obtained from PBS-injected and anti-MBP T cell-injected rats (n-8; p=0.8, Student's t-test). The neuroprotective effect of anti-MBP T cells (relative to PBS) on the injured nerve on day 14 after injury was significant (n=8, p=0.009, Student's t-test).
Figure 6B:
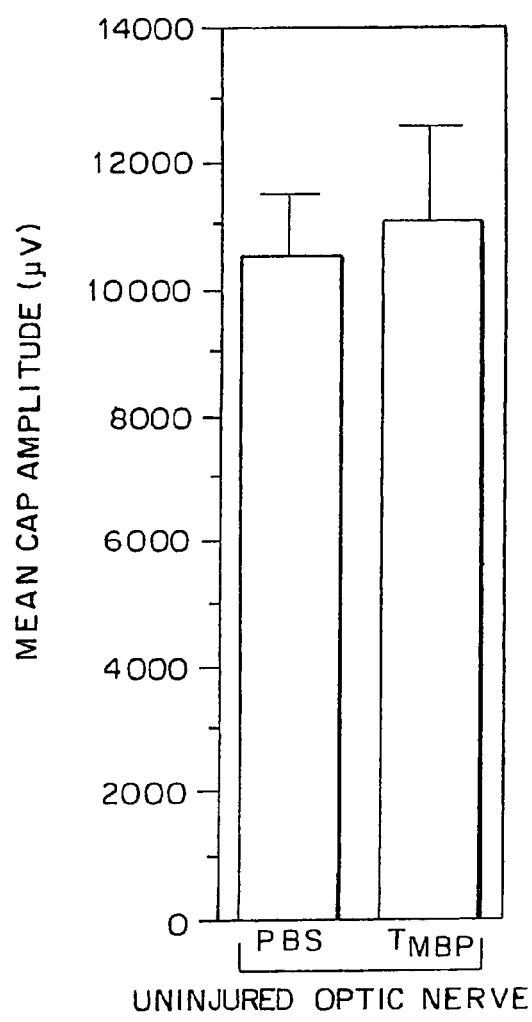

To confirm the neuroprotective effect of the anti-MBP T cells, electrophysiological studies were done. Immediately after optic nerve injury, the rats were injected intraperitoneally with PBS or with $1 \times 10^7$ activated anti-MBP or anti-OVA T cells. The optic nerves were excised 7, 11 or 14 days later and the CAPs, a measure of nerve conduction, were recorded from the injured nerves. On day 14, the mean CAP amplitudes of the distal segments recorded from the injured nerves obtained from the PBS-injected control rats were 33% to 50% of those recorded from the rats injected with the anti-MBP T cells (FIG. 6A, Table 2). As the distal segment of the injured nerve contains both neurons that escaped the primary insult and injured neurons that have not yet degenerated, the observed neuroprotective effect could reflect the rescue of spared neurons, or a delay of Wallerian degeneration of the injured neurons (which normally occurs in the distal stump), or both. No effect of the injection of anti-MBP T cells on the mean CAP amplitudes of uninjured nerves was observed (FIG. 6B, Table 2). It is unlikely that the neuroprotective effect observed on day 14 could have been due to the regrowth of nerve fibers, as the time period was too short for this.

The strong neuroprotective effect of the anti-MBP T cells seen on day 14 was associated with a significantly decreased CAP amplitude recorded on day 7 (Table 2). The anti-MBP T cells manifested no substantial effect on the uninjured nerve on day 7, indicating that the reduction in electrophysiological activity observed in the injured nerve on day 7 might reflect the larger number of T cells present at the injury site relative to the uninjured nerve (FIG. 1). The observed reduction in CAP amplitude in the injured nerve on day 7 reflected a transient resting state in the injured nerve. This transient effect has not only disappeared, but was even reversed by day 14 (Table 2). Early signs of the neuroprotective effect could already be detected on day 11 in the rats injected with anti-OVA T cells, no reduction in CAP amplitude on day 7 could be detected in either the injured or the uninjured nerves, and no neuroprotective effect was observed on day 14 (Table 2). Thus, it seems that the early reduction in CAP and the late neuroprotection shown specifically by the anti-MBP T cells are related.

TABLE 2

Transient Reduction in Electrophysiological Activity of the Injured Optic Nerve Induced by Anti-MBP T Cells, Followed by a Neuroprotective Effect

| | Uninjured Optic Nerve | | Injured Optic Nerve | |
| --- | --- | --- | --- | --- |
| | Day 7 | Day 14 | Day 7 | Day 14 |
| Ratio (&) | 89.9 + 9.4 | 101.2 + 22.7 | 63.8* + 14.9 | 243.1** + 70.8 |
| $T_{MPB}$/PBS | (n = 22) | (n = 10) | (n = 17) | (n = 8) |
| Ratio (%) | 109.7 + 13. | 92.5 + 12.6 | 125.5 + 24.4 | 107.3 + 38.9 |
| $T_{OVA}$/PBS | (n = 11) | (n = 3) | (n = 11) | (n = 4) |

Immediately after optic nerve injury, rats were injected with PBS or with activated anti-MBP or anti-OVA T cells. After 7 or 14 days, the CAPs of injured and uninjured nerves were recorded. Ratios were calculated for uninjured nerves as (mean CAP of uninjured nerves from T cell-injected rats/mean CAP of uninjured nerves from PBS-injected rats) × 100, or for injured nerves as (mean CAP of injured nerves from T cell-injected rats/mean CAP of injured nerves from PBS-injected rats) × 100.The P value was calculated by comparing the logarithms of the normalized CAP amplitudes of nerves from PBS-injected rats and rats injected with T cells, using the unpaired Student's test, *P < 0.05; **P < 0.001 n = sample size.

Neuroprotection in Spinal Cord Injury by Anti-MBP T Cells

Materials and Methods

Animals, antigens (MBP, OVA) and T cell lines were as described hereinbefore in Example 6 animals, antigens and T cell lines, respectively.

Contusion. Adult rats (300 to 350 g) were anesthetized and the spinal cord was exposed by laminectomy at the level of T7-T8. One hour after induction of anesthesia, a 10-gram rod was dropped onto the laminectomized cord from a height of 50 mm. The impactor device (designed by Prof. Wise Young) allowed, for each animal, measurement of the trajectory of the rod and its contact with the spinal cord to allow uniform lesion. Within an hour of the contusion, rats were injected i.p., on a random basis, with either $10^7$ cells (specific to either MBP or OVA, depending on the experimental design) or with PBS. Bladder expression was done at least twice a day (particularly during the first 48 h after injury, when it was done 3 times a day) until the end of the second week, by which time the rats had developed autonomous bladder voidance. Approximately twice a week, locomotor activity (of the trunk, tail and hind limbs) in an open field was evaluated by placing the rat for 4 min in the middle of a circular enclosure made of molded plastic with a smooth, non-slip floor (90 cm diameter, 7 cm wall height).

RESULTS

The present study of spinal cord neuroprotection was prompted by the previous example that partial injury to an optic nerve can be ameliorated administering T cells directed to a CNS self-antigen. The question was whether autoimmune T cells could have a beneficial effect on recovery from traumatic spinal cord injury with its greater mass of injured CNS tissue and the attendant spinal shock.

Adult Lewis rats were subjected to a calibrated spinal cord contusion produced by dropping a 10-gram weight from a height of 50 mm onto the laminectomized cord at the level of T7-T8 (see Basso et al, 1996). The rats were then injected intraperitoneally with autoimmune T cells specific to MBP. Control rats were similarly injured but received either no T cells or T cells specific to the non-self antigen ovalbumin (OVA). Recovery of the rats was assessed every 3 to 4 days in terms of their behavior in an open-field locomotion test, in which scores range from 0 (complete paraplegia) to 21 (normal mobility). The locomotor performance of the rats was judged by observers blinded to the identity of the treatment received by the rats. Included in the study was a group of uninjured, sham-operated (laminectomized but not contused) rats that were injected with anti-MBP T cells to verify the activity of the T cells. In all the sham-operated rats, the anti-MBP T cells induced clinical EAE, which developed by day 4, reached a peak at day 7 and resolved spontaneously by day 11. Note, therefore, that at the early post-traumatic stage, any effect of the autoimmune T cells on the injured spinal cord, whether positive or negative, would be transiently masked both by spinal shock and by the paralysis of EAE.

Figure 7A:
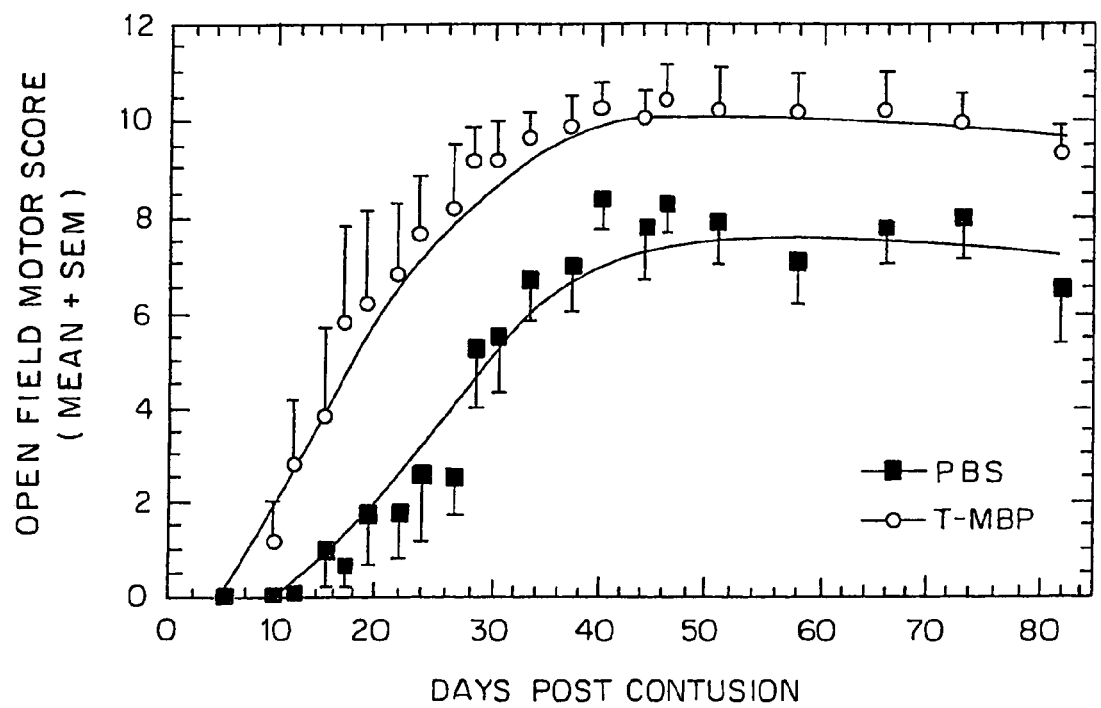
(FIG. 7A) Twelve rats were deeply anesthetized and laminectomized, and then subjected to a contusion insult produced by a 10 gram weight dropped from a height of 50 mm. Six of the rats, selected at random, were then inoculated i.p. with $10^7$ anti-MBP T cells and the other six were inoculated with PBS. At the indicated time points, locomotor behavior in an open field was scored by observers blinded to the treatment received by the rats. Results are expressed as the mean values for each group. The vertical bars indicate SEM. Differences tested by repeated ANOVA, including all time points, were significant (p<0.05).

Indeed, none of the rats with contused spinal cords showed any locomotor activity in the first few days after the contusion (FIG. 7A). Interestingly, however, the rats treated with anti-MBP T cells recovered earlier from spinal shock; on day 11, for example, when no recovery could be detected in any of the untreated control rats, significant improvement was noted in the T cell-treated rats (FIG. 7A). At all time points thereafter, the rats that had received the autoimmune T cells showed better locomotor recovery than did the untreated injured rats (FIG. 7A). Thus the autoimmune T cells, in spite of being encephalitogenic, did confer significant neuroprotection. Moreover, the phase of neuroprotective activity coincided with the phase of immune paralysis, supporting our suggestion that neuroprotection might be related to transient paralysis.

By one month after trauma the rats in both groups had reached a maximal behavioral score, which then remained at plateau for at least 3 months of follow-up. In the untreated rats, maximal recovery of locomotor behavior, as noted in previous reports of similarly severe contusion (Basso et al, 1996), was marked by some ineffectual movement of hindlimb joints, but the rats showed no ability to support their body weight and walk, and obtained a score of 7.3±0.8 (mean±SEM). In contrast, the average score of the rats that had been treated with the anti-MBP T cells was 10.2±0.8, and in some rats the value was as high as 13. All the rats in the treated group could support their body weight and some could frequently walk in a coordinated fashion. The difference between the two groups, based on 2-factor repeated ANOVA, was statistically significant (p<0.05). The recovery curve based on locomotor activity is nonlinear. The above-described increase in motor activity seen after treatment with the anti-MBP T cells could result from much higher percentage of spared tissue based on a linear regression curve on which the behavioral score is correlated with the amount of neural spinal cord tissue (for example, a difference between 11 and 7 on the locomotion score would be read as a difference between 30% and less than 10% of spared tissue).

Figure 7B:
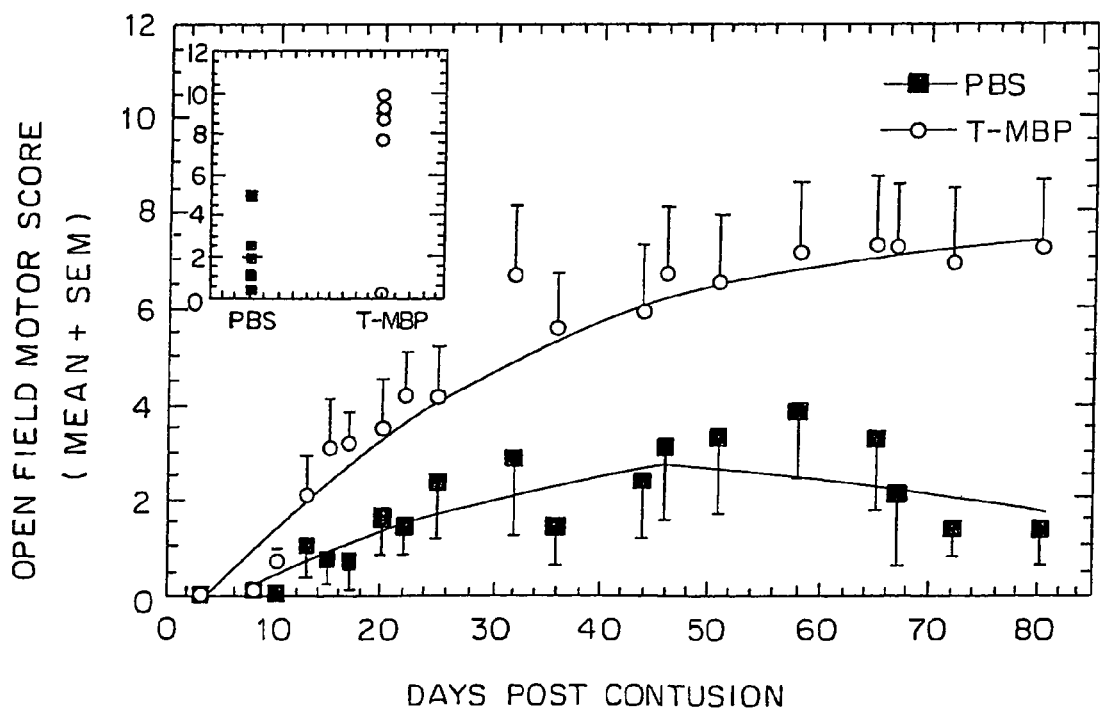
(FIG. 7B) A similar experiment using five PBS-treated animals and six animals treated with anti-MBP T cells were all subjected to a more severe contusion. At the indicated time points, locomotor behavior in an open field was scored. The results are expressed as the mean values for each group. The vertical bars indicate SEM. Rats in the treated group are represented by open circles and rats in the control group are represented by black circles. Horizontal bars show the median values. The inset shows the median plateau values of the two groups.

In another set of experiments the rats were subjected to a more severe insult, resulting in a functional score of 1.9±0.8 (mean±SEM) in the untreated group and 7.7±1.4 in the treated group (FIG. 7B). This difference of more than 3 fold in behavioral scores was manifested by the almost total lack of motor activity in the control rats as compared with the ability of the autoimmune T cell-treated rats to move all their joints. The beneficial effect was specific to treatment with anti-MBP T cells; no effect was observed after treatment with T cells specific to the non-self antigen OVA (data not shown). The positive effect of the autoimmune T cells seems to be expressed in the preservation of CNS tissue that escaped the initial lesion, i.e., in neuroprotection. Therefore, the magnitude of the effect would be inherently limited by the severity of the insult; the more severe the lesion, the less the amount of spared tissue amenable to neuroprotection.

Figure 8A:
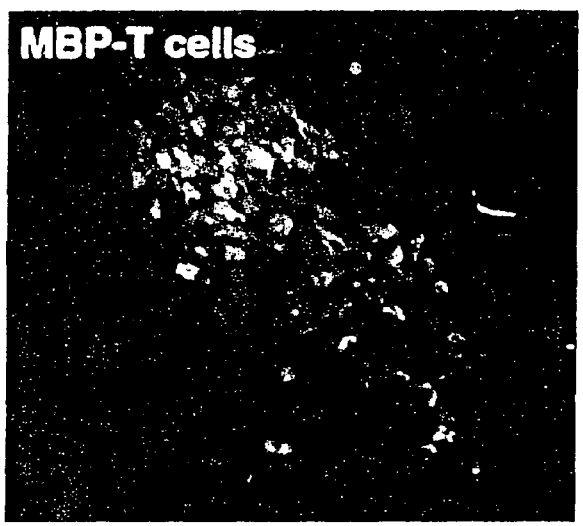
FIGS. 8(A-C) show retrograde labeling of cell bodies at the red nucleus in rats treated with autoimmune anti-MBP T cells (8A) and in control injured (8B) rats. Three months after contusion and treatment with anti-MBP T cells, some rats from both the treated and the control groups were re-anesthetized and a dye was applied below the site of the contusion. After five to seven days, the rats were again deeply anesthetized and their brains were excised, processed, and cryosectioned. Sections taken through the red nucleus were inspected and analyzed qualitatively and quantitatively under fluorescent and confocal microscopes. Significantly, more labeled nuclei were seen in the red nuclei of rats treated with anti-MBP T cells (8A) than in the red nuclei of PBS-treated rats (8B). The quantitative differences are shown in the bar graph (8C) and were obtained from animals with scores of 10 and 11 in the T-cell-treated group and scores of 6 in the control group. The bar graph shows mean±SD.
Figure 8B:
Figure 8C:
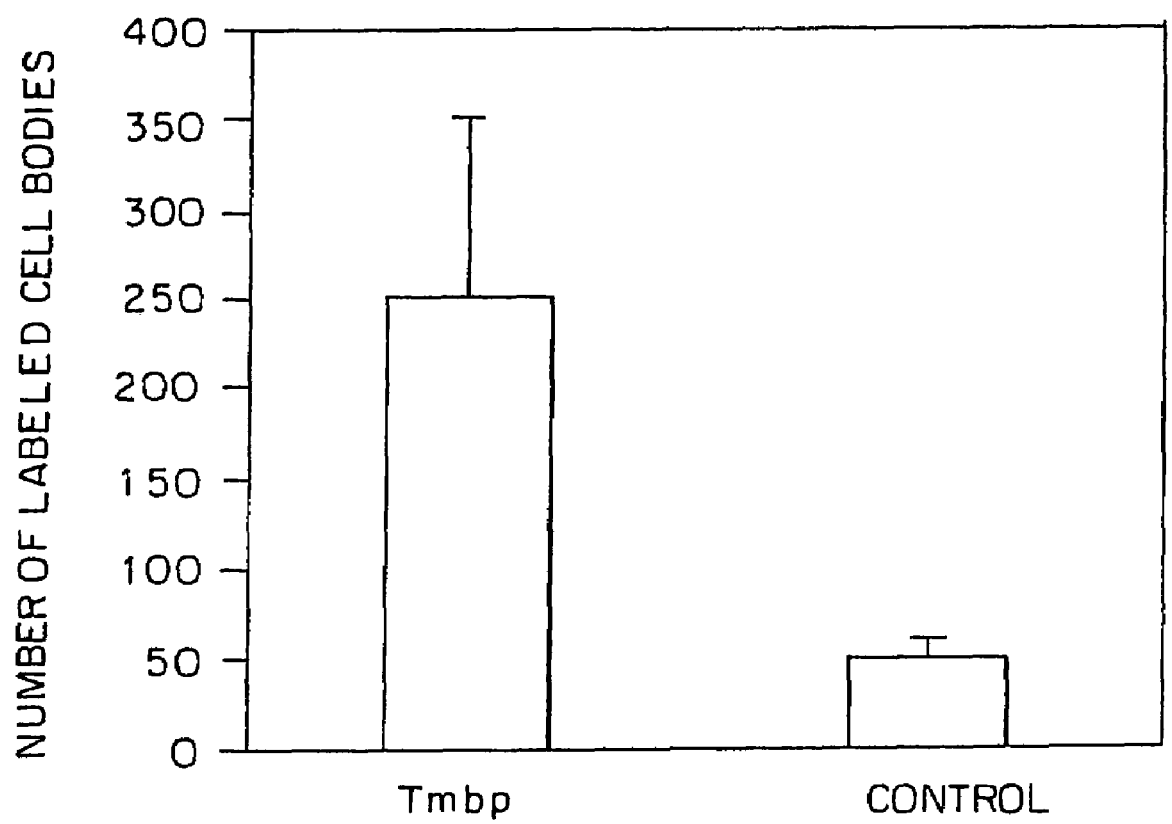

To determine whether clinical recovery could be explained in terms of preservation of spinal axons, we performed retrograde labeling of the descending spinal tracts by applying the dye rhodamine dextran amine (Brandt et al, 1992) at T12, below the site of damage. The number of dye-stained cells that could be counted in the red nucleus of the brain constituted a quantitative measure of the number of intact axons traversing the area of contusion. Sections of red nuclei from injured rats treated with anti-MBP T cells (FIG. 8) contained 5-fold more labeled cells than sections taken from the untreated injured rats. Photomicrographs of red nuclei taken from rats treated with anti-MBP T cells (with an open field score of 10) and from PBS-treated rats (with a score of 6) are shown in FIG. 8. These findings indicate that the reduction in injury-induced functional deficit observed in the T cell-treated rats can be attributed to the sparing of spinal tracts, resulting in a higher degree of neuron viability.

Figure 9:
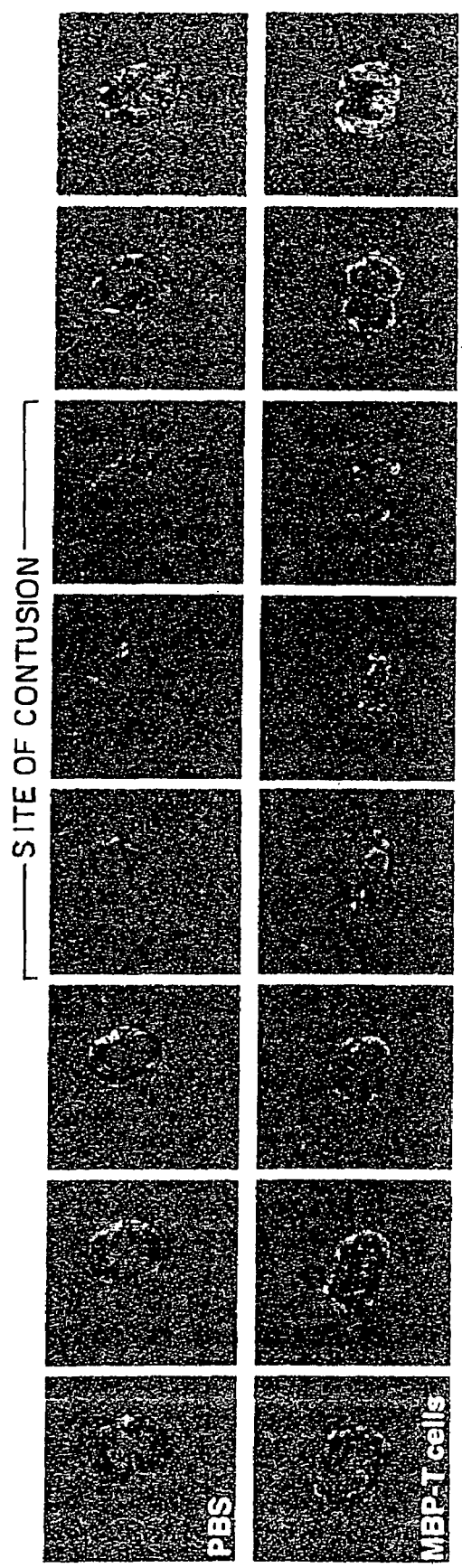
FIG. 9 is a series of photographs showing diffusion-weighted imaging of contused spinal cord treated with anti-MBP T cells. Spinal cords of MBP-T cell-treated and PBS-treated animals (with locomotion scores of 10 and 8, respectively) were excised under deep anesthesia, immediately fixed in 4% paraformaldehyde solution, and placed into 5 mm NMR tubes. Diffusion anisotropy was measured in a Bruker DMX 400 widebore spectrometer using a microscopy probe with a 5-mm Helmholtz coil and actively shielded magnetic field gradients. A multislice pulsed gradient spin echo experiment was performed with 9 axial slices, with the central slice positioned at the center of the spinal injury. Images were acquired with TE of 31 ms, TR of 2000 ms, a diffusion time of 15 ms, a diffusion gradient duration of 3 ms, field of view 0.6 mm, matrix size 128×128, slice thickness 0.5 mm, and slice separation of 1.18 mm. Four diffusion gradient values of 0, 28, 49, and 71 g/cm were applied along the read direction (transverse diffusion) or along the slice direction (longitudinal diffusion). Diffusion anisotropy is manifested by increased signal intensity in the images with the highest transverse diffusion gradient relative to the longitudinal diffusion gradient. The excised spinal cords of a PBS-treated rat and in the rat treated with MBP-T cells were subjected to diffusion-weighted MRI analysis. In the PBS-treated injured control, diffusion anisotropy was seen mainly in sections near the proximal and distal stumps of the cord, with low anisotropy in sections taken through the site of injury. In contrast, in the treated rat, higher levels of diffusion anisotropy can be seen in sections taken through the site of injury.

After a follow-up of more than 3 months, when the locomotor activity scores had reached a plateau, the site of injury of three of PBS-treated animals and three animals treated with anti-MBP T cells were analyzed by diffusion-weighted MRI. The cords were excised in one piece from top to bottom and were immediately placed in fixative (4% paraformaldehyde). Axial sections along the excised contused cord were analyzed. FIG. 9 shows the diffusion anisotropy in axial sections along the contused cord of a rat treated with autoimmune T cells, as compared with that of PBS-treated control rat. The images show anisotropy in the white matter surrounding the gray matter in the center of the cord. Sections taken from the lesion sites of PBS-treated control rats show limited areas of anisotropy, which were significantly smaller than those seen at comparable sites in the cords of the rats treated with the anti-MBP T cells. Quantitative analysis of the anisotropy, reflecting the number of spared fibers, is shown in FIG. 9. The imaging results show unequivocally that, as a result of the treatment with the autoimmune anti-MBP T cells, some spinal cord tracts had escaped the degeneration that would otherwise have occurred.

DISCUSSION OF RESULTS

No cure has yet been found for spinal cord lesions, one of the most common yet devastating traumatic injuries in industrial societies. It has been known for more that 40 years that CNS neurons, unlike neurons of the PNS, possess only a limited ability to regenerate after injury. During the last two decades, attempts to promote regeneration have yielded approaches that lead to partial recovery. In the last few years it has become apparent that, although most of the traumatic injuries sustained by the human spinal cord are partial, the resulting functional loss is nevertheless far worse than could be accounted for by the severity of the initial insult; the self-propagating process of secondary degeneration appears to be decisive.

A substantial research effort has recently been directed to arresting injury-induced secondary degeneration. All attempts up to now have been pharmacologically based, and some have resulted in improved recovery from spinal shock. The present study, in contrast, describes a cell therapy that augments what seems to be a natural mechanism of self-maintenance and leads, after a single treatment, to long-lasting recovery. The extent of this recovery appears to exceed that reported using pharmacological methods.

In most tissues, injury-induced damage triggers a cellular immune response that acts to protect the tissue and preserve its homeostasis. This response has been attributed to macrophages and other cells comprising the innate arm of the immune system. Lymphocytes, which are responsible for adaptive immunity, have not been thought to participate in tissue maintenance. Adaptive immunity, according to traditional teaching, is directed against foreign dangers. Our studies now show, however, that the adaptive T cell immune response can be protective even when there is no invasion by foreign pathogens. In the case of tissue maintenance, the specificity of the T cells is to tissue self-antigens.

Our observation of post-traumatic CNS maintenance by autoimmune T cells suggests that we might do well to reevaluate some basic concepts of autoimmunity. T cells that are specific to CNS self antigens in general, and to MBP in particular, have long been considered to be only detrimental to health. In the present study, however, the same T cell preparation that can produce EAE in the undamaged CNS was found to be neuroprotective in the damaged spinal cord, suggesting that the context of the tissue plays an important part in determining the outcome of its interaction with T cells. It would seem that the tissue deploys specific signals to elicit particular T cell behaviors. Among such signals are co-stimulatory molecules, particularly members of the B7 family (Lenchow et al, 1996). As shown hereinafter, the injured rat optic nerve transiently expresses elevated levels of the co-stimulatory molecule B7.2, which is constitutively expressed at low levels in the rat CNS white matter and which is thought to be associated with regulation of the cytokine profile of the responding T cells (Weiner, 1997). The early post-injury availability of the exogenous anti-MBP T cells, coinciding with the observed early post-injury increase in B7.2, would support the idea that signals expressed by the tissue might modulate the T cell response. It is thus conceivable that anti-MBP T cells which cause a monophasic autoimmune disease upon interacting with a healthy CNS nerve, might implement a maintenance program when they interact with damaged CNS tissue expressing increased amounts of B7.2 and probably other co-stimulatory molecules. The neuroprotective effects of the T cells may be mediated, at least in part, by antigen-dependent regulation of specific cytokines or neurotrophic factors (Kerschensteiner et al, 1999) produced locally at the site of injury.

Thus, the present invention is also directed to manipulating B7.2 co-stimulatory molecule to prevent or inhibit neuronal degeneration and ameliorate the effects of injury to or disease of the nervous system. B7.2 molecule can be up-regulated for this purpose, using drugs or by genetic manipulation, without undue experimentation.

In a recent study, it was reported that injury to the spinal cord triggers a transient autoimmune response to MBP (Popovich et al, 1996). However, whether that response is detrimental or beneficial remained an open question (Popovich et al, 1997). From our present data, it would appear that the activation of anti-MBP T cells could indeed be beneficial. However, a supplement of exogenous autoimmune T cells may be required to overcome the restrictions on immune reactivity imposed by the immune-privilege of the CNS (Streilein, 1995). The finding that autoimmune response can be advantageous suggests that natural autoimmune T cells may have undergone positive selection during ontogeny, as proposed by the theory of the immunological homunculus (Cohen, 1992), and are not merely a default resulting from the escape from negative selection of T cells that recognize self antigens (Janeway, 1992). Such a response could then be considered as a mechanism of potential physiological CNS self-maintenance, which is, however, not sufficient for the purpose because of the immune-privileged character of the CNS.

A single injection of autoimmune T cells lasted for at least 100 days. Thus, this procedure offers a form of self-maintenance. This specific autoimmune response, when properly controlled, is useful as part of a self-derived remedy for spinal cord injury.

EXAMPLE 3

Neuroprotective Effects of a NS-Specific Antigen Peptide—MOG p35-55

Materials and Methods

Animals, crush injury of rat optic nerve, and retrograde labeling are described above in Examples 3 and 4. A peptide based on amino acids 35-55 of MOG (MOG p35-55) was chemically synthesized at the Weizmann Institute, Israel.

Inhibition of Secondary Degeneration

Rats were injected intradermally in the footpads with MOG p35-55 (50 µg/animal) and IFA, or PBS, ten days prior to optic nerve crush injury. RGCs were assessed two weeks after injury using retrograde labeling as described above. The number of RGCs in rats injected with PBS or MOG p35-55 was expressed as a percentage of the total number of neurons in rats injected with MOG p35-55 in the absence of crush injury.

RESULTS

Figure 10:
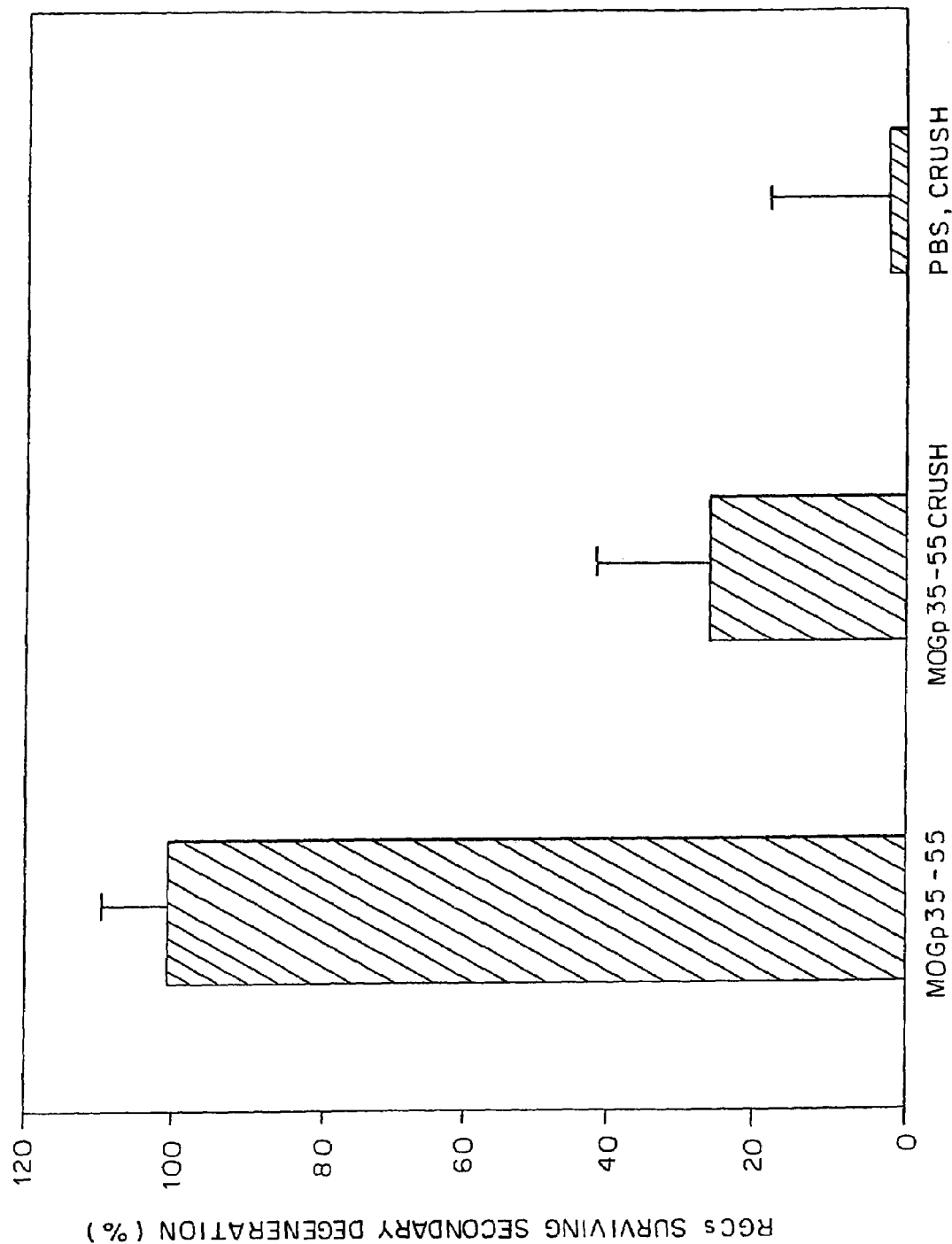
FIG. 10 is a graph illustrating inhibition of secondary degeneration after optic nerve crush injury in adult rats. See text, Example 3, for experimental details. Rats were injected intradermally through the footpads with a 21-mer peptide based on MOG amino acid residues 35-55 (MOG p35-55) ((50 μ/animal, chemically synthesized at the Weizmann Institute of Science, Rehovot, Israel) or PBS ten days prior to optic nerve crush injury or MOG p35-55 in the absence of crush injury. MOG p35-55 was administered with IFA. Surviving optic nerve fibers were monitored by retrograde labeling of RGCs. The number of RGCs in rats injected with PBS or MOG p35-55 was expressed as a percentage of the total number of neurons in rats injected with MOG p35-55 in the absence of crush injury.

As shown in FIG. 10, the number of labeled RGCs (indicating viable axons) was about 12.5-fold greater in animals injected with MOG p35-55 compared to animals receiving PBS.

EXAMPLE 4

Neuroprotective Effects of MBP Administered Orally

Materials and Methods

Animals, crush injury of rat optic nerve, and retrograde labeling of RGCs are described above in Examples 3 and 4.

Inhibition of Secondary Degeneration

Bovine MBP (Sigma, Israel) (1 mg/dose) was administered to rats by gavage using a blunt needle. MBP was administered 5 times, every third day, beginning 2 weeks prior to optic nerve crush injury. The number of RGCs in treated animals was expressed as a percentage of the total number of neurons in animals subjected to optic nerve crush injury but which did not receive MBP.

RESULTS

Figure 11:
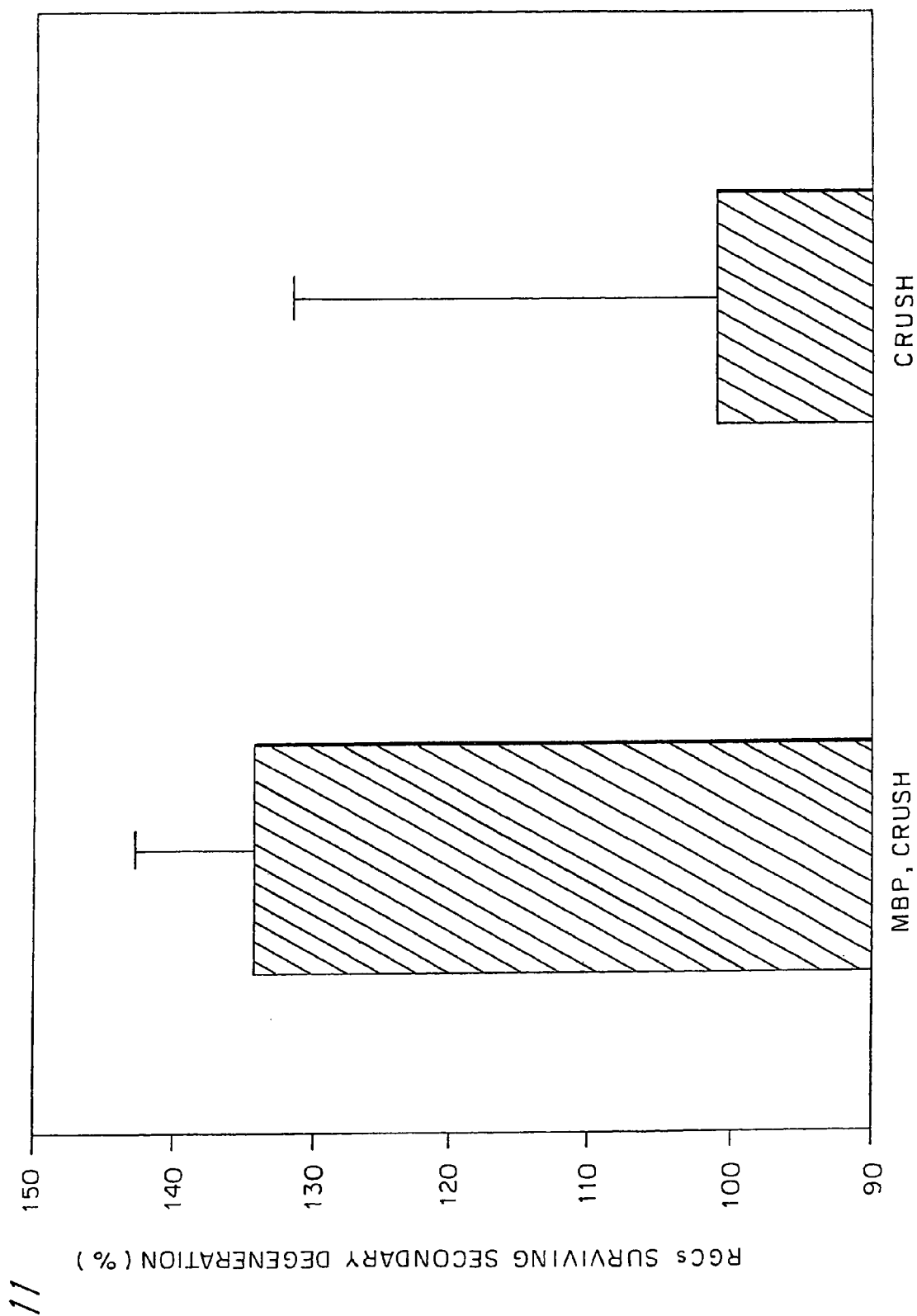
FIG. 11 is a graph illustrating inhibition in adult rats of secondary degeneration after optic nerve crush injury by MBP. See text, Example 4, for experimental details. MBP (Sigma, Israel) (1 mg in 0.5 ml saline) was administered orally to adult rats by gavage using a blunt needle. MBP was administered 5 times, i.e., every third day beginning two weeks prior to optic nerve crush injury. Surviving optic nerve fibers were monitored by retrograde labeling of RGCs. The number of RGCs in treated rats was expressed as a percentage of the total number of neurons in untreated rats following the injury.

As shown in FIG. 11, the number of labeled RGCs was about 1.3 fold greater in animals treated with MBP compared to untreated animals.

The B7.2 Co-Stimulatory Molecule is Associated with Post-Traumatic Maintenance of the Optic Nerve by Oral Administration of MBP Introduction Autoimmune T cells can under certain conditions be beneficial to traumatized CNS axons. The effect of such T cells on the damaged tissue might be influenced by the nature and amount of the co-stimulatory molecules it expresses. We show that the B7.2 co-stimulatory molecule is constitutively expressed in the intact rat optic nerve, and after injury is up-regulated at the margins of the injury site. Pre-injury induction of oral tolerance to MBP resulted in a further post-injury increase in B7.2 at the margins and at the injury site itself, as well as a better preservation of the traumatized nerve. Thus, B7.2 expression in the brain and its up-regulated after trauma seem to be directly related to post-traumatic maintenance displayed by autoimmune T cells.

Neuronal injury in the CNS causes degeneration of directly damaged fibers as well as of fibers that escaped the primary insult. It also triggers a systemic response of autoimmune T cells to MBP that might affect the course of degeneration of the injured nerve. Whether the effect of these T cells on the nerve is detrimental or beneficial may depend, in part, on the nature and level of the co-stimulatory molecules expressed by the damaged tissue.

Several co-stimulatory molecules have recently been identified, including the B7 and CD40 molecules (Caux et al, 1994; Lenschow et al, 1996). CD40 appears to be dominant during cell differentiation in the lymph nodes and B7 during activation of T cells in the target organ (Grewal et al, 1996).

The B7 co-stimulatory molecule is a member of the immunoglobulin superfamily that interacts with CD28 and CTLA-4 on $T_H$ cells. There are two related forms of B7 (B7.1 and B7.2). Both molecules have a similar organization of extracellular domains but markedly different cytosolic domains. Both B7 molecules are expressed on antigen-presenting cells (APCs) such as dendritic cells, activated macrophages and activated B cells as B7.1 or B7.2., which might preferentially support activation of the Th1 or the Th2 type of immune response, respectively (Kuchroo et al, 1995; Karandikar et al, 1998). We were therefore interested in determining the identity of B7 molecule subtype expressed in intact and injured CNS white matter, and its possible influence on the course of the response to the injury.

RESULTS

The co-stimulatory molecule expressed constitutively in the intact optic nerves of adult Lewis rats was identified as B7.2. (FIGS. 12A, 12B). To examine the effects of neurotrauma on the expression of B7 co-stimulatory molecules, we inflicted a mild crush injury on the optic nerves of Lewis rats and assessed the neural expression of B7 by immunohistochemical analysis. The most striking effect of the injury was seen on B7.2 expression manifested on post-injury day 3 by its elevation at the margins of the injury site (FIGS. 12C, D, E). In contrast, expression of B7.1 was not detected in the optic nerve either before or 3 days after injury. On day 7, however, B7.1 was detectable at the site of injury, having pattern reminiscent of that seen for macrophages or microglia (FIG. 12F).

Next, we attempted to determine whether the degenerative response to optic nerve injury could be modified by peripheral manipulation of the immune system. The manipulation chosen was induction of oral tolerance, known to cause a "bystander" T cell immunosuppressive effect (Weiner et al, 1997b). Ingestion of low doses of MBP results in the activation of T cells which, based on antigen recognition, secrete TGF as the dominant cytokine and thus favor an immune response of Th2/3 type (Chen et al, 1994).

Lewis rats were fed with food to which 1 mg of bovine MBP had been added five times daily every other day. Ten days after first receiving the supplement, the rats were subjected to mild unilateral optic nerve crush injury. This time, interval between initiation of oral tolerance and injury was chosen to allow adequate build-up of the systemic T cell response. As shown in FIGS. 13A and 13B, the numbers of macrophages or active microglia (indicated by ED-1 labeling) and T cells (indicated by immunolabeling for T cell receptor), assessed 3 days after injury, did not differ from those observed in control injured rats which did receive any treatment or were fed with PBS. In the rats with induced oral tolerance to MBP, however, the amounts of B7.2 were further increased at the margins of the site of injury (FIG. 13C) as compared with controls (FIG. 12E). In addition, in the rats with induced oral tolerance to MBP, B7.2 was also elevated at the site of injury relative to the control nerves (FIG. 13C). It seems reasonable to assume that the T cells exposed to MBP via intestinal absorption, upon invading the injured CNS, contributed to the increase in expression of B7.2 by the injured nerve.

Figure 14:
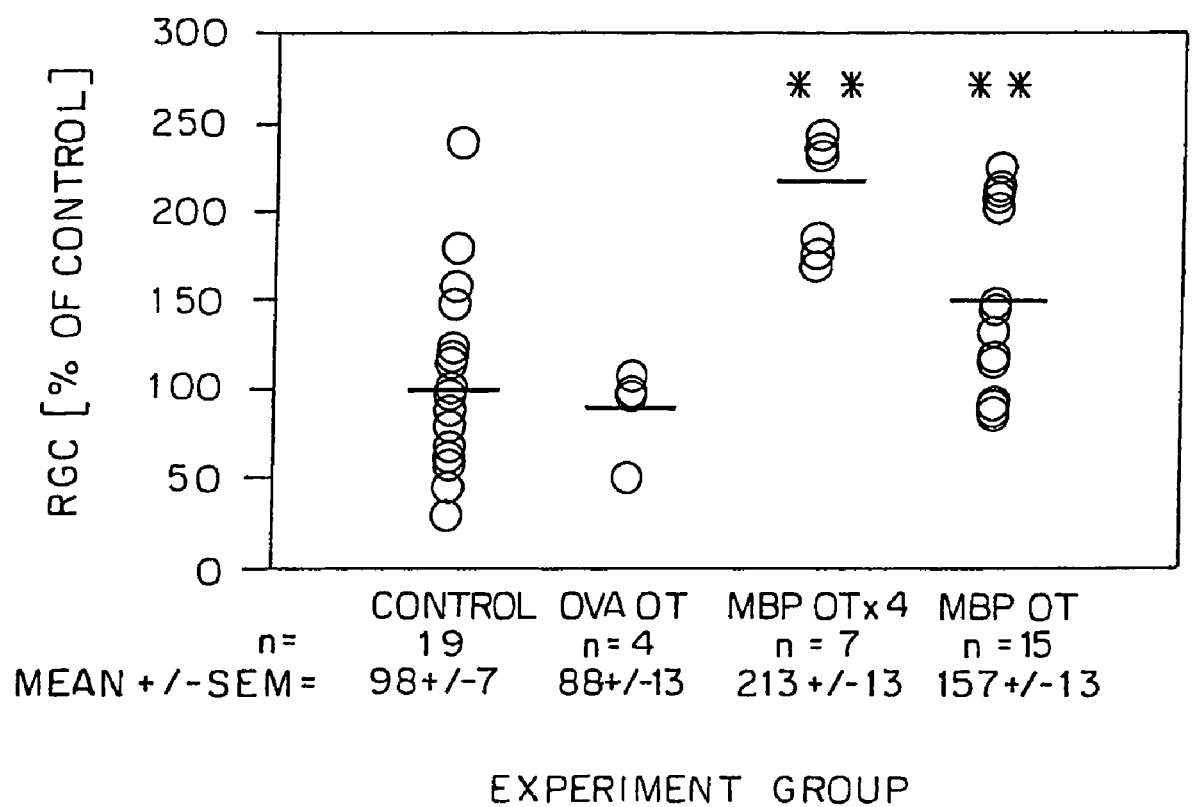
FIG. 14 is a graph showing the slowing of neuronal degeneration in rats with orally induced tolerance to MBP. Lewis rats were fed 1 mg MBP daily, or every other day, or 4 times a day at two-hour intervals for five consecutive days. Control animals were given PBS or the non-self antigen OVA Sigma, Israel). Ten days after the start of MBP ingestion, the right optic nerves were subjected to a calibrated mild crush injury. Two weeks later the RGCs were retrogradely labelled by application of the fluorescent lipophilic dye 4-Di-10-Asp (Molecular Probes Europe BV, Netherlands), distally to the site of injury, as described. Briefly, complete axotomy was performed 1-2 mm from the distal border to the injury site, and solid crystals (0.2-0.4 mm in diameter) of 4-Di-10-Asp were immediately deposited at the site of the lesion. Retrograde labeling of RGCs by the dye gives a reliable indication of the number of still-functioning neurons, as only intact axons can transport the dye to their cell bodies in the retina. Six days after dye application, the retina was detached from the eye, prepared as a flattened whole mount in 4% paraformaldehyde solution, and examined for labeled RGCs by fluorescence microscopy. RGCs were counted from three different regions in the retina. The results are expressed as normalized percentage of each retina to untreated injured animal mean of the same experiment. The median of each group is shown as a bar (Control vs. MBP OTx4  P<0.01; Control vs. MBP TO  P, 0.01; Control vs. OVA TO ns P>0.05.

We then attempted to determine whether the observed changes in B7.2 expression in the injured rats was correlated with the extent of neuronal degeneration. Acute injury of the rat optic nerve is followed by a process of nerve degeneration, which can be quantified by retrograde labeling of the surviving neurons and counting of the corresponding cell bodies. Two weeks after optic nerve injury, the number of surviving RGCs, representing still-viable neurons, in the group of MBP-fed rats, was significantly higher than that in the control group, or that in the group of rats with injured nerves that were fed with ovalbumin (OVA). Interestingly, the benefit of the induced oral tolerance to MBP was increased by feeding the rats with more intensive schedule (FIG. 14).

EXAMPLE 5

Posttraumatic Immunization with nogo P472 Peptide Promotes Function Recovery from Spinal Cord Contusion Materials and Methods Animals. Female and male SPD rats were supplied by the Animal Breeding Center of the Weizmann Institute of Science, Rehovot, Israel, matched for age (8-12 weeks) and housed in light- and temperature-controlled rooms.

Antigen. The Nogo p472 peptide (SEQ ID NO:19) was synthesized at the Weizmann Institute of Science, Rehovot, Israel.

Immunization. Rats were immunized with 100-150 μg of Nogo p472 peptide emulsified in CFA containing 1 mg/ml *Mycobacterium tuberculosis*. The emulsion was injected subcutaneously at one site in the upper back in the rats. The p472-immunized rats were boosted one week after injury with p472 (100 μg/rat) in IFA. Control rats were injected either with PBS or with PBS emulsified in CFA (Difco, Detroit, Mich., USA).

Contusion. Adult rats were anesthetized and their spinal cords were exposed by laminectomy at the level of T9. One hour after induction of anesthesia, a 10-g rod was dropped onto the laminectomized cord from a height of 25 mm or 50 mm, using the NYU impactor (Basso et al, 1995 and 1996).

INTRODUCTION

Regeneration of axons after injury in the CNS of higher vertebrates is extremely limited and almost absent. Growth inhibitors associated with CNS myelin play an important role in this aspect. A potent neurite growth inhibitory activity associated with adult CNS oligodendrocytes and myelin was reported by Caroni and Schwab, 1988, and found to be neutralized by a monoclonal antibody, IN-1, which was shown to promote axonal regeneration and to enhance compensatory plasticity following spinal cord or brain lesions in adult rats.

This activity was later related to a high molecular weight membrane protein, designated NI-250, with a smaller component, NI-35, in rat. The bovine homologue of rat NI-250, bNI-220, was recently purified (Chen et al, 2000; PCT Publication WO 00/31235). The cloning of nogo A, the rat cDNA encoding NI-220/250, was recently reported (see FIG. 1a of Chen et al, 2000; and PCT Publication WO 00/31235, the entire contents of both of which being hereby incorporated herein by reference). The rat nogo gene (SEQ ID NO: 17) encodes at least three major protein products: Nogo-A (SEQ ID NO:18) (1,163 amino acids; database accession number AJ242961), Nogo-B (SEQ ID NO:20) (360 amino acids; AJ242962) and Nogo-C (SEQ ID NO:21) (199 amino acids; AJ242963). The sequence of the amino acid p472 (SEQ ID NO:19) containing the residues 623-640 of rat Nogo-A, is shown in the box in FIG. 1a of Chen et al, 2000. The cloning of the corresponding human cDNA and protein is reported in Prinjha et al, 2000. See also WO 00/60083 and WO 01/36631.

PCT Publication WO 00/31235 describes methods for the production of recombinant Nogo proteins, fragments, derivatives and analogs thereof, and DNA molecules coding therefor. This publication further describes the use of a Nogo protein or fragment thereof for the treatment of neoplastic diseases of the CNS such as glioma, glioblastoma, retinoblastoma, and the like; and further describes the use of a ribozyme or an antisense Nogo nucleic acid for treatment of a subject with damage to the CNS and/or for inducing regeneration of neurons, wherein said ribozyme or antisense Nogo nucleic acid acts by inhibiting the production of Nogo in the subject. It is thus unexpected that immunization with Nogo or fragments thereof and/or administration of T cells activated therewith can promote nerve regeneration or prevent or inhibit neuronal degeneration in the NS, as shown according to the present invention.

PCT publication WO 00/31235, WO 00/60083 and WO 01/36631 are all hereby incorporated herein by reference. All CNS protein polypeptides and nucleotides disclosed herein can be used in the process of the present invention.

RESULTS

SPD male rats (n=5 per group) were subjected to severe spinal cord contusion as described in the Materials and Methods section of this example and a 10-g rod was dropped onto the laminectomized cord from a height of 50 mm (FIG. 24A) or 25 mm (FIG. 24B) using the NYU impactor. Soon thereafter the rats were immunized subcutaneoulsy with Nogo p472 peptide (100 µg/rat) emulsified in CFA containing 1 mg/ml Mycobacterium tuberculosis. Control male rats (n=5 per group) were injected with PBS emulsified in CFA.

Figure 25:
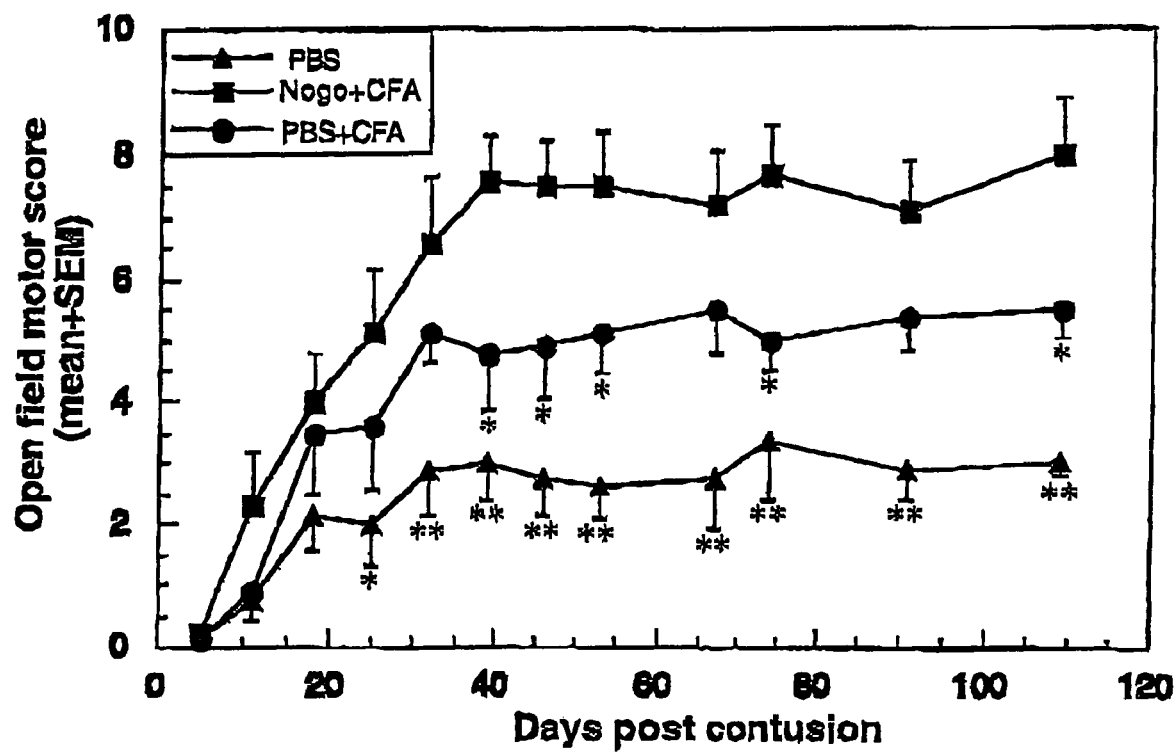
FIG. 25 show that post-traumatic immunization with Nogo peptide p472 emulsified in CFA promotes functional recovery from spinal cord contusion in comparison to PBS-treated or PBS+CFA-treated rats. Spinal cords of female SPD rats were laminectomized at the level of T9 and a 10-g rod was dropped onto the laminectomized cord from a height of 50 mm. See text, Example 5, for experimental details.

In another experiment, 5 female rats were subjected to severe spinal cord contusion as described in the Materials and Methods section of this example and a 10-g rod was dropped onto the laminectomized cord from a height of 50 mm (FIG. 25) using the NYU impactor. Soon thereafter the rats were immunized subcutaneoulsy with Nogo p472 peptide (100 µg/rat) emulsified in CFA containing 1 mg/ml *Mycobacterium tuberculosis*. Control female rats (n=5 per group) were injected with PBS emulsified in CFA or with PBS alone. P472-immunized rats were boosted one week after injury and immunization with p472 (100 µg/rat) in IFA.

Acute incomplete spinal cord injury at the low thoracic levels causes an immediate loss of hindlimb motor activity that spontaneously recovers within the first 12 days post-injury and stabilizes on deficient movement abilities. The amount of motor function restoration is the sum up effect of the positive recovery from spinal shock and the negative effect of longitudinal and ventral spread of damage. A therapeutic approach aiming at reducing the spread of damage through neuroprotection will result in a better recovery in terms of hindlimb motor activity. The hind limb motor skills of the animals were scored using the BBB scoring method developed by Basso et al, 1996, following the kinetics and amount of hindlimb motor activity in the two experimental groups.

Figure 24A:
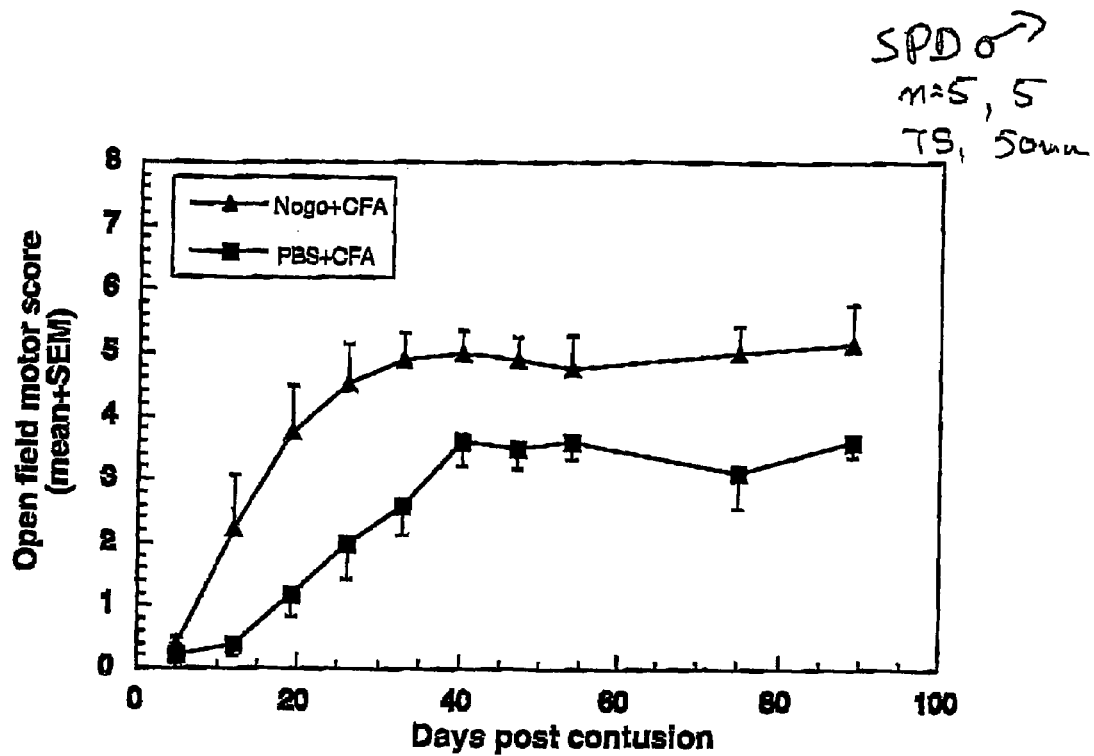
FIGS. 24(A-B) show that post-traumatic immunization with Nogo peptide p472 emulsified in CFA promotes functional recovery from spinal cord contusion in comparison to PBS+CFA-treated rats. Spinal cords of male SPD rats were laminectomized at the level of T9 and a 10-g rod was dropped onto the laminectomized cord from a height of 50 mm (FIG. 24A) or of 25 mm (FIG. 24B). See text, Example 5, for experimental details.
Figure 24B:
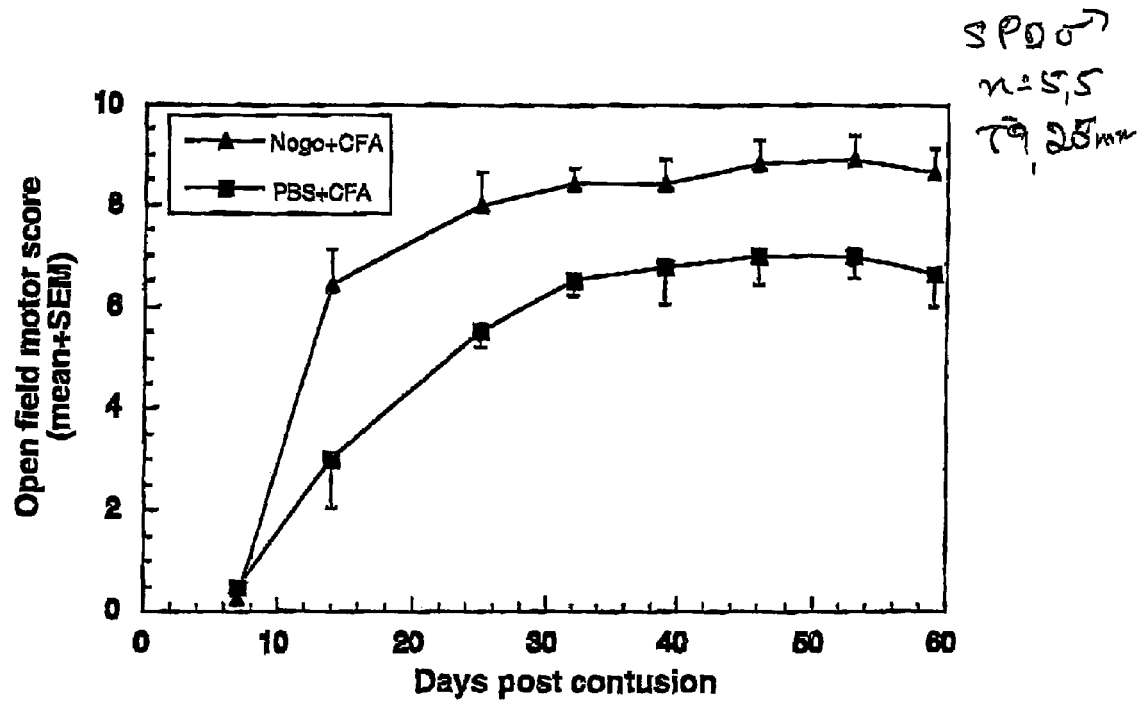

The results of the experiments above, depicted in FIGS. 24(A-B) and 25, show that both female (squares, FIG. 25) and male (triangles, FIGS. 24A-B) p472-immunized rats showed significantly improved overall functional recovery compared to the control rats injected with PBS in CFA (squares, FIGS. 24A-B and circles, FIG. 25) or PBS only (triangles, FIG. 25) ($P<0.01$, one way repeated measurements ANOVA). Males (FIGS. 24 A-B) showed significantly better locomotor performance than PBS+CFA-treated controls from day 11 after the injury and at all times points measured thereafter. Females (FIG. 25) showed significantly better hind limb locomotion than PBS-treated controls from day 25 and on ($P<0.05$, $P<0.01$, $*P<0.001$, two-tail Student T-test).

Discussion of Experimental Results

The results of the experiments described in Examples 1 and 2 show that activated T cells accumulate at a site of injury in the CNS. Furthermore, the results also demonstrate that the accumulation of T cells at the site of injury is a non-specific process, i.e., T cells which accumulated at the site of injury included both T cells which are activated by exposure to an antigen present at the site of injury as well as T cells which are activated by an antigen not normally present in the individual.

The results of experiments described in Example 3 demonstrate that the beneficial effects of T cells in ameliorating damage due to injury in the CNS are associated with an NS-specific self-antigen as illustrated by MBP. More specifically, the administration of non-recombinant T cells which were activated by exposure to an antigen which can cause autoimmune disease ($T_{MBP}$), rather than aggravating the injury, led to a significant degree of protection from secondary degeneration. Thus, activating T cells by exposure to a fragment of an NS-specific antigen was beneficial in limiting the spread of injury in the CNS. The present findings show that secondary degeneration can be inhibited by the transfer into the individual on non-recombinant T cells which recognize an NS-specific self antigen which is present at a site of injury. The T cells may recognize cryptic or non-pathogenic epitopes of NS-self antigens.

In addition, the experiments described in Examples 3, 4 and 5 show that activation of T cells by administering an immunogenic antigen (e.g., MBP) or immunogenic epitope of an antigen (e.g., MOG p35-55 or Nogo p472), may be used for preventing or inhibiting secondary CNS degeneration following injury.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation, and that other means or steps for carrying out the same function can be used; and it is intended that such expressions be given their broadest interpretation.

All publications cited herein are incorporated by reference in their entirety.

REFERENCES

Altschul, et al, 1990, *J. Mol. Biol.* 215(3):403-410.
Arquint et al, *Proc. Natl. Acad. Sci. USA* 84:600-604, 1987.
Ashwood-Smith, 1961, *Nature* 190:1204-1205.
Basso, D M, Beattie, M S and Bresnahan, J C, 1995, "A sensitive and reliable locomotor rating scale for open field testing in rats, *J. Neurotrauma* 12(1):1-21.
Basso D M, Beattie, M S and Bresnahan, J C, 1996, "Graded histological and locomotor outcomes after spinal cord contusion using the NYU weight-drop device versus transection, *Exp.Neurol.* 139(2): 244-256.
Bazan, N. G., Rodriguez de Turco, E. B., Allan, G., 1995, "Mediators of injury in neurotrauma: intracellular signal transduction and gene expression",*J. Neurotrauma* 12:791-814.
Bender et al, 1960, *J. Appl. Physiol.* 15:520.
Ben-Nun, A., et al, 1981a, "The rapid isolation of clonable antigen-specific T-lymphocyte lines capable of mediating autoimmune encephalomyelitis *Eur. J. Immunol.* 11:195-199.
Ben-Nun, A., Wekerle, H. and Cohen, I. R., 1981, "Vaccination against autoimmune encephalomyelitis with T-lymphocyte line cells reactive against myelin basic protein", *Nature* 292:60-61.

Ben-Nun, A. and Cohen, I. R., 1982, "Experimental autoimmune encephalomyelitis (EAE) mediated by T-cell lines: process of selection of lines and characterization of the cells", *J. Immunol.* 129:303-308.

*Bone-Marrow Conservation, Culture and Transplantation, Proceedings of a Panel, Moscow, Jul.* 22-26, 1968, International Atomic Energy Agency, Vienna, pp. 107-186.

Brandt et al, 1992, *J.Neurosci.Methods* 45:35-40.

Burns, J., Rosenzweig, A., Zweiman, B., Lisak, R. P., 1983, Isolation of myelin basic protein-reactive T-cell lines from normal human blood", *Cell Immunol.* 81:435-440.

Caroni, P. and Schwab, M. E., 1988, "Two membrane protein fractions from rat central myelin with inhibitory properties for neurite growth and fibroblast spreading" *J. Cell Biol.* 106: 1281-1288.

Caux et al, 1994, "Activation of Human Dendritic Cells through CD40 Cross-Linking", *J. Exp. Med.* 180:1263-1272.

Chen, Y., Kuchroo, V. K.,. Inobe, J. Hafler, D. A. & Weiner, H. L., 1994, "Regulatory T cell clones induced by oral tolerance: suppression of autoimmune encephalomyelitis" *Science* 265:1237-1240.

Chen, M. S., Huber, A. B., van der Haar, M. E., Schwab, M. E., 2000, "Nogo-A is a myelin-associated neurite outgrowth inhibitor and an antigen for monoclonal antibody IN-1", *Nature* 403:434-439.

Cohen, I. R., 1992, *Immunol. Today* 13, 490-494.

Diehl et al, *Proc. Natl. Acad Sci. U.S.A.* 83(24):9807-9811, 1986 (published erratum appears in *Proc Natl Acad Sci U.S.A.* 86(6):617-8, 1991).

Duvdevani et al, 1990, *Neurol. Neurosci.* 2:31-38.

Elias et al, 1991, *Proc. Natl. Acad. Sci. USA* 88:3088-3091.

Faden, A. I., et al, 1992, *Trends Pharmacol. Sci.* 13:29-35.

Faden, A. I., 1993, "Experimental neurobiology of central nervous system trauma", *Crit. Rev. Neurobiol.* 7:175-186.

Fournier, A. E., GrandPré, T., Strittmatter, S. M., 2001, "Identification of a receptor mediating Nogo-66 inhibition of axonal regeneration", *Nature* 409:341.

Gonzalez et al, *Mol. Phylogent. Evol.* 6:63-71, 1996.

Gorin, *Clinics in Haematology,* 1986, 15(1):19-48.

Grewal et al, 1996, "Requirement for CD40 Ligand in Co-stimulation Induction, T Cell Activation, and Experimental Allergic Encephalomyelitis", *Science* 273:1864-1867.

Hauben, E. et al, 2000, "Passive or active immunization with myelin basic protein promotes recovery from spinal cord contusion", *J. Neurosci.* 20:6421-6430.

Hickey, W. F. et al, 1991, "T-lymphocyte entry into the central nervous system", *J. Neurosci. Res.* 28:254-260.

Higgins, et al, 1996, *Methods Enzymol* 266:383-402.

Hirschberg, D. L., et al, 1998, "Accumulation of passively transferred primed T cells independently of their antigen specificity following central nervous system trauma", *J. Neuroimmunol.* 89:88-96.

Hirshfeld, et al, 1970, *FEBS Lett.* 7:317.

Hovda, D. A. et al, 1991, *Brain Res.* 567:1-10.

Hunig et al, 1989, "A monoclonal antibody to a constant determinant of the rat T cell antigen receptor that induces T cell activation. Differential reactivity with subsets of immature and mature T lymphocytes", *J. Exp. Med., 169:* 73-86.

Hutchinson, C., et al, 1978, *J. Biol. Chem* 253:6551.

Janeway, C. A. Jr., 1992, "The immune system evolved to discriminate infectious nonself from noninfectious self", *Immunol. Today* 13:11-16.

Kamholz et al, 1986, *Proc. Natl. Acad. Sci. U.S.A.* 83(13): 4962-4966.

Karandikar et al, 1998, "Targeting the B7/CD28:CTLA-4 co-stimulatory system in CNS autoimmune disease", *J. Neuroimmunol.* 89:10-18.

Kerschensteiner, M. et al, 1999, *J. Exp. Med.* 189:865-870.

Kramer, R. et al, 1995, *Nature Med.* 1(11):1162-1166

Kuchroo et al, 1995, "B7-1 and B7-2 co-stimulatory molecules activate differentially the Th1/Th2 developmental pathways: application to autoimmune disease therapy", *Cell* 80:707-718.

Lazarov Spiegler, O., et al, 1996, *FASEB J.* 19:1296-1302.

Lenschow et al, 1996, "CD28/B7 System of T Cell co-stimulation", *Annu. Rev. Immunol.* 14:233-258.

Lewis et al, 1967, Transfusion 7(1):17-32.

Linner et al, *J. Histochem. Cytochem.,* 1986, 34(9):1123-1135.

Livesey and Linner, *Nature,* 1987, 327:255.

Lovelock, *Biochem. J.* 56:265, 1954.

Lovelock and Bishop, *Nature* 183:1394-1395, 1959.

Lynch, D. R. et al, 1994, "Secondary mechanisms in neuronal trauma", *Curr. Opin. Neurol.* 7:510-516.

Maniatis, T., 1990, *Molecular Cloning, A Laboratory Manual,* 2d ed., Cold Spring Harbor Laboratory, Cold Spring Harbor, N.Y.

Martin, R. et al, 1990, *J. Immunol.* 145:540-548.

Martin, R. 1997, *J. Neural Transm. Suppl.* 49:53-67.

Mazur, *Science,* 1970, 168:939-949.

McIntosh, T. K., 1993, :Novel pharmacologic therapies in the treatment of experimental traumatic brain injury: a review", *J. Neurotrauma* 10:215-261.

Moalem, G. et al, 1999, "Autoimmune T cells protect neurons from secondary degeneration after central nervous system axotomy", *Nature Med.* 5: 49-55.

Mor et al, 1990, "Clinical modeling of T cell vaccination against autoimmune diseases in rats. Selection of antigen-specific T cells using a mitogen", *Clin. Invest.* 85:1594-1598.

Mor et al, 1995, "Pathogenicity of T cells responsive to diverse cryptic epitopes of myelin basic protein in the Lewis rat", *J. Immunol.* 155:3693-3699.

Nave et al, *Proc. Natl. Acad. Sci. U.S.A* 84:600-604, 1987.

Ota, K. et al, 1990, "T-cell recognition of an immunodominant myelin basic protein epitope in multiple sclerosis", *Nature* 346:183-187.

Pearson and Lipman, 1988, *Proc. Natl. Acad. Sci. USA* 85:2444-8.

Pette, M. et al, 1990, "Myelin basic protein-specific T lymphocytes lines from MS patients and healthy individuals", *Proc. Natl. Acad. Sci. USA* 87:7968-7972.

Phan The Tran and Bender, 1960, *Proc. Soc. Exp. Biol. Med.* 104:388.

Phan The Tran and Bender, *Exp. Cell Res.* 20:651, 1960.

Phan The Tran and Bender, 1961, in *Radiobiology, Proceedings of the Third Australian Conference on Radiobiology,* Ilbery, P.L.T., ed., Butterworth, London, p. 59.

Popovich, P. G., Stokes, B. T., Whitacre, D. C., 1996, "Concept of autoimmunity following spinal cord injury: possible roles for T lymphocytes in the traumatized central nervous system", *J. Neurosci. Res.* 45:349-63.

Popovich et al, 1997, *J. Comp. Neurol.* 377:443-464.

Prinja et al, "Inhibitor of neurite outgrowth in humans", *Nature* 403(6768):383-384 (2000)

Rapalino, O., Lazarov-Spiegler, O., Agranov, E., Schwartz, M., 1998, "Implantation of stimulated homologous macrophages results in partial recovery of paraplegic rats", *Nature Med.* 4:814-821.

Rapatz et al, *Cryobiology,* 1968, 5(1):18-25.

Rinfret, *Ann. N.Y. Acad. Sci.* 85:576, 1960.

Roth et al, *Genomics* 28(2):241-250, 1995.
Rowe, *Cryobiology*, 1966, 3(1):12-18.
Rowe and Rinfret, 1962, *Blood,* 20:636.
Rowe et al, *Fed. Proc.,* 1962, 21:157.
Schaich et al, 1986, *Biol. Chem.* 367:825-834.
Schluesener, H. J. and Wekerle, H., 1985, "Autoaggressive T lymphocyte lines recognizing the encephatoligenic region of myelin basic protein: in vitro selection from unprimed rat T lymphocyte populations", *J. Immunol.* 135:3128-3133.
Sloviter and Ravdin, *Nature* 196:548, 1962.
Spitzer et al, *Cancer,* 1980, 45:3075-3085.
Stiff et al, *Cryobiology,* 1983, 20:17-24.
Streilein, J. W., 1993, *Curr. Opin. Immunol.* 5:428-423.
Streilein, J. W., 1995, *Science* 270:1158-1159.
Suruhan-Dires Keneli et al, 1993 *Euro. J. Immunol.* 23:530.
Thompson, et al, 1994, *Nucleic Acids Res.* 22(22):4673-80.
Vergelli, M. et al, 1996, "Differential activation of human autoreactive T cell clones by altered peptide ligands derived from myelin basic protein peptide (87-99)", *Eur. J. Immunol.* 26: 2624-2634.
Weiner et al, 1997a, Annu. Rev. Med. 48:341-51.
Weiner et al, 1997b, "Tolerance Immune Mechanisms and Treatment of Autoimmune Diseases", *Immunol. Today* 18:335-343. Werkele, H., 1993, In *The Blood-Brain Barrier*, Pardridge, Ed., Raven Press, Ltd. New York, 67-85.
Wu, D. et al, 1994, *J.Neurochem.* 62:37-44.
Yoles, E. et al, 1992, *Invest. Ophthalmol. Vis. Sci.* 33:3586-3591).
Yoles et al, 1996, *J. Neurotrauma* 13:49-57.
Yoshina, A. et al, 1991 *Brain Res.* 561:106-119.
Zaroulis and Leiderman, *Cryobiology* 17:311-317, 1980.
Zivin, J. A., et al, 1991 *Sci. Am.* 265:56-63.

What is claimed is:

1. A method for reducing secondary neuronal degeneration that follows neuronal damage caused by an injury, disease, disorder or condition in the central or peripheral nervous system of an individual in need thereof, comprising:

causing T cells activated against a nervous system (NS)-specific antigen which, in its native state, is present at the site of secondary neuronal degeneration, to accumulate at the site of secondary neuronal degeneration in the individual in need, thereby reducing secondary neuronal degeneration at that site, wherein, when the individual in need has an autoimmune disease, the NS-specific antigen is not the autoimmune antigen of that disease, and when the individual in need has a neoplasm, the NS-specific antigen is one that does not appear in the neoplasm, wherein said causing step is accomplished by— administering an effective amount of said NS-specific antigen, or an immunogenic epitope thereof, in such a manner as to cause a T cell response thereto, such that T cells become activated against the NS-specific antigen which is present at the site of secondary neuronal degeneration, wherein said NS-specific antigen or immunogenic epitope thereof that is administered is myelin basic protein (MBP), the peptide p51-70 of MBP, or Nogo-A p472 peptide (SEQ ID NO:19); or administering an effective amount of T cells that are activated against said NS-specific antigen or said immunogenic epitope thereof, wherein said activated T-cells are T-cells activated against MBP or the peptide p51-70 of MBP.

2. A method in accordance with claim 1, wherein said activated T cells are caused to accumulate at the site of secondary neuronal degeneration by administering an effective amount of said NS-specific antigen, or said immunogenic epitope thereof, in such a manner as to cause a T cell response thereto, such that T cells become activated against the NS-specific antigen which is present at the site of secondary neuronal degeneration.

3. A method in accordance with claim 1, wherein said activated T cells are caused to accumulate at the site of secondary neuronal degeneration by administering an effective amount of T cells that are activated against said NS-specific antigen or said immunogenic epitope thereof.

4. A method in accordance with claim 1, wherein the individual in need is one suffering from an injury that has caused primary neuronal damage.

5. A method in accordance with claim 1, wherein the individual in need is one suffering from a disease, disorder or condition that has neurodegenerative effects.

6. The method according to claim 2, wherein the NS-specific antigen or immunogenic epitope thereof is myelin basic protein (MBP) or p51-70 of MBP.

7. The method according to claim 6, wherein the NS-specific antigen or immunogenic epitope thereof is MBP.

8. The method according to claim 7, wherein the MBP is administered orally.

9. The method according to claim 2, wherein said NS-specific antigen or immunogenic epitope thereof is p51-70 of MBP.

10. The method according to claim 2, wherein said NS-specific antigen or immunogenic epitope thereof is the Nogo-A p472 peptide (SEQ ID NO:19).

11. The method according to claim 2, wherein said NS-specific antigen or immunogenic epitope thereof, is administered intravenously, intrathecally, intramuscularly, intradermally, topically, subcutaneously, or mucosally.

12. The method according to claim 11, wherein said mucosal administration is selected from the group consisting of oral, intranasal, buccal, vaginal and rectal administration.

13. The method according to claim 12, wherein said NS-specific antigen, or immunogenic epitope thereof, is administered orally and the individual is actively immunized to build up a critical T cell response.

14. A method in accordance with claim 3, wherein said T cells are autologous.

15. The method according to claim 3, wherein said T cells are semi-allogeneic T cells.

16. The method according to claim 3, wherein said activated T cells have been sensitized to said NS-specific antigen or said immunogenic epitope thereof.

17. The method according to claim 3, wherein the NS-specific antigen or immunogenic epitope thereof is MBP.

18. The method according to claim 3, wherein said NS-specific antigen or immunogenic epitope thereof is p51-70 of MBP.

19. The method according to claim 4, wherein said autologous T cells have been stored for future use.

20. The method according to claim 4, wherein said injury is spinal cord injury.

21. A method for ameliorating the secondary neurodegenerative effects of an injury, disease, disorder or condition that causes secondary neuronal degeneration of the central or peripheral nervous system of an individual in need thereof, comprising:

causing T cells activated against a nervous system (NS)-specific antigen which, in its native state, is present at the site of secondary neuronal degeneration, to accumulate at the site of secondary neuronal degeneration in the individual in need, thereby ameliorating the effects of the injury, disease, condition or disorder at that site, wherein, when the individual in need has an autoimmune disease, the NS-specific antigen is not the autoimmune antigen of that disease, and when the individual in need has a neoplasm, the NS-specific antigen is one that does not appear in the neoplasm, wherein said causing step is accomplished by—
administering an effective amount of said NS-specific antigen, or an immunogenic epitope thereof, in such a manner as to cause a T cell response thereto, such that T cells become activated against the NS-specific antigen which is present at the site of secondary neuronal degeneration, wherein said NS-specific antigen or immunogenic epitope thereof that is administered is myelin basic protein (MBP), the peptide p51-70 of MBP, or Nogo-A p472 peptide (SEQ ID NO:19); or
administering an effective amount of T cells that are activated against said NS-specific antigen or said immunogenic epitope thereof, wherein said activated T-cells are T-cells activated against MBP or the peptide p51-70 of MBP.

22. A method in accordance with claim 21, wherein said activated T cells are caused to accumulate at the site of secondary neuronal degeneration by administering an effective amount of said NS-specific antigen, or said immunogenic epitope thereof, in such a manner as to cause a T cell response thereto, such that T cells become activated against the NS-specific antigen which is present at the site of secondary neuronal degeneration.

23. A method in accordance with claim 21, wherein said activated T cells are caused to accumulate at the site of secondary neuronal degeneration by administering an effective amount of T cells that are activated against said NS-specific antigen or said immunogenic epitope thereof.

24. A method in accordance with claim 23, wherein said T cells are autologous.

25. A method in accordance with claim 21, wherein the individual in need is one suffering from an injury that has caused primary neuronal damage.

26. The method according to claim 25, wherein said injury is spinal cord injury.

27. A method in accordance with claim 21, wherein the individual in need is one suffering from a disease, condition or disorder that has neurodegenerative effects.

* * * * *